US012644148B2

(12) United States Patent
Blake et al.

(10) Patent No.: US 12,644,148 B2
(45) Date of Patent: Jun. 2, 2026

(54) IN VITRO DETECTION OF NUCLEIC ACID

(71) Applicant: PRESIDENT AND FELLOWS OF HARVARD COLLEGE, Cambridge, MA (US)

(72) Inventors: William Jeremy Blake, Winchester, MA (US); Carl W. Brown, III, West Roxbury, MA (US); James J. Collins, Newton, MA (US); Frederic Vigneault, Ashland, MA (US)

(73) Assignee: PRESIDENT AND FELLOWS OF HARVARD COLLEGE

( * ) Notice: Subject to any disclaimer, the term of this patent is extended or adjusted under 35 U.S.C. 154(b) by 895 days.

(21) Appl. No.: 17/268,010

(22) PCT Filed: Aug. 14, 2019

(86) PCT No.: PCT/US2019/046497
§ 371 (c)(1),
(2) Date: Feb. 11, 2021

(87) PCT Pub. No.: WO2020/037038
PCT Pub. Date: Feb. 20, 2020

(65) Prior Publication Data
US 2021/0164025 A1 Jun. 3, 2021

Related U.S. Application Data

(60) Provisional application No. 62/718,427, filed on Aug. 14, 2018.

(51) Int. Cl.
*C12Q 1/6825* (2018.01)

(52) U.S. Cl.
CPC ..... *C12Q 1/6825* (2013.01); *C12Q 2600/158* (2013.01)

(58) Field of Classification Search
CPC .. C12Q 1/6825; C12Q 1/6897; C12Q 1/6816; C12Q 2600/158; C12P 19/34
See application file for complete search history.

(56) References Cited

U.S. PATENT DOCUMENTS

| | | | |
|---|---|---|---|
| 5,194,370 | A | 3/1993 | Berninger et al. |
| 5,652,107 | A | 7/1997 | Lizardi et al. |
| 5,792,614 | A | 8/1998 | Western et al. |
| 5,807,674 | A | 9/1998 | Tyagi |
| 6,110,677 | A | 8/2000 | Western et al. |
| 6,183,960 | B1 | 2/2001 | Lizardi |
| 6,197,508 | B1 | 3/2001 | Stanley |
| 6,316,229 | B1 | 11/2001 | Lizardi et al. |
| 6,955,901 | B2 | 10/2005 | Schouten |
| 7,164,992 | B1 | 1/2007 | Mulligan et al. |
| 8,148,065 | B1 | 4/2012 | Wallace |
| 9,758,780 | B2 | 9/2017 | Xiao et al. |
| 2002/0102568 | A1 | 8/2002 | Usman et al. |
| 2003/0008295 | A1 | 1/2003 | Usman et al. |

| | | | |
|---|---|---|---|
| 2003/0065155 | A1 | 4/2003 | Usman et al. |
| 2004/0171047 | A1* | 9/2004 | Dahl .................... C12Q 1/6865 |
| | | | 435/5 |
| 2005/0074804 | A1 | 4/2005 | Wang et al. |
| 2005/0186624 | A1* | 8/2005 | Dautel ................. C12Q 1/6897 |
| | | | 435/6.16 |
| 2005/0227235 | A1 | 10/2005 | Carr et al. |
| 2006/0211000 | A1 | 9/2006 | Sorge et al. |
| 2007/0003936 | A1 | 1/2007 | Gite et al. |
| 2007/0087417 | A1 | 4/2007 | Namsaraev |
| 2007/0099208 | A1 | 5/2007 | Drmanac et al. |
| 2008/0090238 | A1 | 4/2008 | Yang et al. |
| 2008/0194416 | A1 | 8/2008 | Chen |
| 2009/0215633 | A1 | 8/2009 | Van Eijk et al. |
| 2010/0003688 | A1 | 1/2010 | Jackson et al. |
| 2011/0003301 | A1 | 1/2011 | Raymond et al. |
| 2011/0039257 | A1 | 2/2011 | Binkowski et al. |
| 2014/0179539 | A1 | 6/2014 | Lohman et al. |
| 2015/0211002 | A1 | 7/2015 | Keefe et al. |
| 2016/0304943 | A1 | 10/2016 | Isgut |
| 2016/0340746 | A1 | 11/2016 | Makarov et al. |

(Continued)

FOREIGN PATENT DOCUMENTS

| | | |
|---|---|---|
| WO | 1999/024621 A3 | 8/1999 |
| WO | 2001/098538 A1 | 12/2001 |
| WO | 2002/044339 A2 | 6/2002 |

(Continued)

OTHER PUBLICATIONS

"The Basics: In Vitro Translation", available on May 25, 2017 as evidenced by the WayBack Machine, accessed Jun. 26, 2024 (Year: 2017).*
*Homo sapiens* hemoglobin subunit beta (HBB), RefSeqGene (LRG_1232) on chromosome 11, NCBI Reference Sequence: NG_059281. 1, accessed Jun. 25, 2024 (Year: 2024).*
Thein, 2013, "The Molecular Basis of b-Thalassemia" Cold Spring Harbor Perspectives in Medicine, 2013:3:a011700 (Year: 2013).*
*Homo sapiens* hemoglobin subunit beta (HBB), mRNA, NCBI Reference Sequence: NM_000518.4, available May 1, 2018, accessed Jun. 26, 2024 (Year: 2018).*
Cao et al., 2002, "Regulation of the Globin Genes", Pediatric Research, vol. 51, No. 4, p. 415-421 (Year: 2002).*
Angioletti et al., 2004, "b+45 G→C: a novel silent b-thalassaemia mutation, the first in the Kozak sequence", BJH, 124, p. 224-231 (Year: 2004).*

(Continued)

*Primary Examiner* — Soren Harward
*Assistant Examiner* — Jenna L Persons
(74) *Attorney, Agent, or Firm* — NIXON PEABODY LLP; David S. Resnick; Nicole D. Kling

(57) ABSTRACT

Described herein are compositions and methods for in vitro detection of nucleic acids. Nucleic acid sensors are activated for cell-free expression of an encoded reporter protein based on the presence of a target nucleic acid. The system is designed to function in low-cost cell extract without the need for instrumentation or stringent temperature control. These features are advantageous for point-of-use molecular diagnostics applications in consumer health, pet/animal health, food safety, and other areas where cost and portability are key factors.

14 Claims, 16 Drawing Sheets

Specification includes a Sequence Listing.

(56)                    References Cited

U.S. PATENT DOCUMENTS

2017/0349939 A1    12/2017  Metzker et al.

FOREIGN PATENT DOCUMENTS

| WO | 2004/044549 | A2 | 5/2004 |
| WO | 2010/094040 | A1 | 8/2010 |
| WO | 2012/004204 | A1 | 1/2012 |
| WO | 2014/074648 | A2 | 5/2014 |
| WO | 2017/019481 | A1 | 2/2017 |
| WO | 2017/191007 | A1 | 11/2017 |

OTHER PUBLICATIONS

*Homo sapiens* hemoglobin subunit beta (HBB), RefSeqGene (LRG_1232) on chromosome 11 NCBI Reference Sequence: NG_059281.1, version Oct. 10, 2024 (Year: 2024).*

UCSC Genome Browser, Assembly hg38, ENST00000335295.4, accessed Dec. 23, 2024, http://genome.ucsc.edu (Year: 2024).*

Wharam et al. "Specific detection of DNA and RNA targets using a novel isothermal nucleic acid amplification assay based on the formation of a three-way junction structure." Nucleic Acids Research 29(11): 1-8 (2001).

Han et al., "Single-stranded DNA and RNA origami", Science 358(6369): eaao2648 (2017).

Dixon et al. "NanoLuc Complementation Reporter Optimized for Accurate Measurement of Protein Interactions in Cells." ACS Chem Biol. 11(2):400-408 (2016).

Martell et al. "A split horseradish peroxidase for the detection of intercellular protein-protein interactions and sensitive visualization of synapses." Nat Biotechnol. 34(7): 774-780 (2016).

Milech et al. "GFP-complementation assay to detect functional CPP and protein delivery into living cells," Sci Rep 5: 18329 (2015).

* cited by examiner

FIG. 3

| T7 Promotor | RBS-ATG | Part A | STOP |
|---|---|---|---|

| T7 Promotor | RBS-ATG | Part B | STOP |
|---|---|---|---|

Luminescence of Split NanoLuciferase Proteins

IN VITRO DETECTION OF NUCLEIC ACID

CROSS-REFERENCE TO RELATED APPLICATIONS

This application is a 35 U.S.C. § 371 National Phase Entry Application of International Patent Application No. PCT/US2019/046497 filed on Aug. 14, 2019, which designated the U.S., which claims benefit under 35 U.S.C. § 119 (e) of U.S. Provisional Application No. 62/718,427 filed Aug. 14, 2018, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jul. 29, 2019, is named 002806-092060WOPT_SL.txt and is 15,781 bytes in size.

FIELD OF THE INVENTION

Described herein are systems and methods for detection of nucleic acids using cell-free expression system.

BACKGROUND

Traditional nucleic acid detection techniques require significant infrastructure and operational investment. In particular, labeling and amplification systems require thermal cycling platforms, and imaging technologies that are bulky and expensive. Such systems also limit opportunity for field deployment. In instances where protein expression is a detection readout, in vivo cell expression systems add a further layer of complexity, without feasible deployment for field use. Thus, there is a great need in the art for systems and methods of reduced complexity, providing flexible deployment with minimal infrastructure.

SUMMARY

Provided herein are methods and compositions which relate to sensor systems for detecting the presence of a target nucleic acid molecule. In the absence of the target, these sensors exist as non-functional parts. In the presence of the target, the parts of the sensor system that comprise the target nucleic acid binding sequence, bind specifically to the target and when bound to the target, are positioned in close proximity with each other, making it possible to form a functional sensor system. When functional, the sensor system can express a reporter protein. Thus, the sensors described herein have very low background signals and are readily adapted to use with existing technology for measuring protein outputs.

Described herein are compositions and methods for in vitro detection of nucleic acids. Nucleic acid sensors are activated for cell-free expression of an encoded reporter protein based on the presence of a target nucleic acid. The system is designed to function in low-cost cell extract without the need for instrumentation or stringent temperature control. These features are advantageous for point-of-use molecular diagnostics applications in consumer health, pet/animal health, food safety, and other areas where cost and portability are key factors.

Aspects of the invention described herein provides a nucleic acid sensor system comprising a first and second single stranded DNA sensor parts which, when ligated together generate a single strand of a DNA expression cassette that comprises i) a promoter; ii) a ribosome binding site (RBS); and iii) a coding sequence. In some embodiments, a target nucleic acid hybridization sequence is located within the first and second single stranded DNA sensor parts.

Aspects of the invention describe a nucleic acid sensor system comprising a first and second single stranded DNA sensor parts which, when ligated together generate a single strand of a DNA expression cassette that comprises i) a promoter; ii) a ribosome binding site (RBS); iii) a coding sequence, which single strand comprises a target nucleic acid hybridization sequence comprising a 3' and 5' hybridization regions, wherein the 3' hybridization region is included in the first sensor part and the 5' hybridization region is included in the second sensor part so that, when the sensor system is contacted with a sample that includes a target nucleic acid that hybridizes with the target nucleic acid sequence, hybridization with the target nucleic acid enables ligation of the first and second parts.

In some embodiments, the DNA expression cassette is a non-template DNA expression cassette. In some embodiments, the first and second sensor parts of the expression cassette are separated at any given position within the expression cassette. In some embodiments, the separation occurs within the target nucleic acid hybridization sequence. In some embodiments, the target nucleic acid hybridization sequence is located at any given position within the expression cassette.

In some embodiments, either the first or the second sensor part comprises the coding sequence and the remaining sensor part comprises the promoter. In some embodiments, either the first or the second sensor part comprises the promoter and the ribosome binding site and the remaining sensor part comprises the coding sequence. In some embodiments, either the first or the second sensor part comprises the promoter, the ribosome binding site, and a start codon of the coding sequence and the remaining sensor part comprises the remaining coding sequence. In some embodiments, the first sensor part comprises, from 5' to 3' i) the promoter, ii) the ribosome binding site (RBS), iii) the start codon for the coding sequence, and iv) the 3' hybridization region in the form of a reading frame in-frame with the start codon; and the second sensor part comprises from 5' to 3' i) the 5' hybridization region in the form of a reading frame in frame with the remaining coding sequence, and ii) a remaining coding sequence linked downstream of and in-frame with the 5' hybridization region.

In some embodiments, either the first or the second sensor part comprises the promoter and the remaining sensor part comprises the ribosome binding site and the coding sequence. In some embodiments, the first sensor part comprises, from 5' to 3' i) the promoter, and ii) the 3' hybridization region; and the second sensor part comprises, from 5' to 3' i) the 5' hybridization region, ii) the ribosome binding sequence, and iii) the coding sequence.

In some embodiments, either the first or the second sensor part comprises the promoter, the ribosome binding site, and a 5' portion of the coding sequence and the remaining sensor part comprises the remaining coding sequence. In some embodiments, the first sensor part comprises, from 5' to 3' i) the promoter, ii) the RBS, iii) a first portion of the coding sequence, comprising a start codon and at least one additional codon, iv) the 3' hybridization region in the form of a reading frame in-frame with the start codon; and the second sensor part comprises, from 5' to 3' i) the 5' hybridization region in the form of a reading frame in-frame with the first portion of the coding sequence and in-frame with the second portion of the coding sequence, and ii) a second portion of the coding sequence linked downstream of and in-frame with the 5' hybridization region.

In some embodiments, at least a portion of the 3' hybridization region is in the promoter, the ribosome binding site, or the coding sequence. In some embodiments, at least a portion of the 5' hybridization region is in the promoter, the ribosome binding site, or the coding sequence. In some embodiments, the 3' hybridization region is not within the promoter, the ribosome binding site, or the coding sequence. In some embodiments, the 3' hybridization region is 3' of any promoter, ribosome binding site, or coding sequence in the first sensor part. In some embodiments, the 5' hybridization region is not within the promoter, the ribosome binding site, or the coding sequence. In some embodiments, the 5' hybridization region is 5' of any promoter, ribosome binding site, or coding sequence in the second sensor part.

In some embodiments, the 3' hybridization region and the 5' hybridization region are collectively at least 12 nucleotides in length. In some embodiments, the 3' hybridization region and the 5' hybridization region are each at least 6 nucleotides in length.

In some embodiments, the first and second sensor parts are on the same molecule. In some embodiments, the 5' end of the first sensor part is linked to the 3' end of the second sensor part through intervening ssDNA sequences so that the first and second sensor part form a single molecule. In some embodiments, the system further comprises a primer complementary to a sequence within the non-template expression cassette or intervening ssDNA sequences. In some embodiments, the first and second sensor parts are on at least two separate molecules.

In some embodiments, the 5' end of the first sensor part further comprises a sequence that forms a terminal hairpin loop. In some embodiments, the system further comprises a primer complementary to a 3' region of the second sensor part. In some embodiments, the system further comprises a primer complementary to a sequence which is 3' of any promoter, ribosome binding site, or coding sequence in the second sensor part. In some embodiments, the system further comprises a primer complementary to a region 5' of any promoter, ribosome binding site, or coding sequence in the second sensor part. In some embodiments, the second sensor part further comprises a nucleotide sequence at its 3' end comprising the primer in a terminal hairpin loop.

In some embodiments, the coding sequence of the DNA expression cassette encodes a polypeptide. In some embodiments, the polypeptide is a reporter protein. In some embodiments, the 3' hybridization region and the 5' hybridization region are located in the coding sequence, within a region encoding for a solvent exposed loop of the reporter protein. In some embodiments, the 3' hybridization region and the 5' hybridization region are located in the coding sequence of the reporter protein and do not substantially impact reporter gene function. In some embodiments, the reporter protein comprises a luciferase, nanoluciferase, beta-lactamase, beta-galactosidase, horseradish peroxidase, alkaline phosphatase, catalase, carbonic anhydrase, green fluorescent protein, red fluorescent protein, cyan fluorescent protein, yellow fluorescent protein, trypsin, a protease, a peptide that complements and activates a truncated reporter protein, and a polypeptide that is detectable by an assay.

In some embodiments, the nucleic acid sensor system further comprises a cell free expression system. In some embodiments, the nucleic acid sensor system further comprises a ligase. In some embodiments, the nucleic acid sensor system further comprises a reverse transcriptase. In some embodiments, the nucleic acid sensor system further comprises a ribonuclease that hydrolyzes RNA which is hybridized to DNA. In some embodiments, the ribonuclease is RNAse H.

In some embodiments, the nucleic acid sensor system further comprises one or more of a ligase, a strand-displacing DNA polymerase, dNTPs, RNAse inhibitor, and a cell free expression system. In some embodiments, the cell free expression system is whole cell extract. In some embodiments, the nucleic acid sensor system further comprising a DNA polymerase. In some embodiments, the DNA polymerase is selected from the group consisting of a Klenow fragment with exonuclease portion, a Klenow fragment without the exonuclease portion, a phi29 polymerase, a modified T7 DNA polymerase, a polymerase from *Psychrobacillus*, a polymerase from *Psychrobacillus* with enhanced strand displacement, a polymerase from *B. subtilis*, Sequenase™ Version 2.0, a Bsu DNA Polymerase Large Fragment, a Bst 3.0 DNA Polymerase, a Phusion® High-Fidelity DNA Polymerase, a Vent® DNA Polymerase without the exonuclease portion, a VentR DNA Polymerase, a Q5® High-Fidelity DNA Polymerase, and a DNA Polymerase I Large (Klenow) Fragment.

In some embodiments, a polymorphism of the target nucleic acid hybridizes to a sequence 3' of the first sensor part hybridization region, and 5' of the second sensor part hybridization region. In some embodiments, the 3' hybridization region of the first sensor part or 5' hybridization region of the second sensor part is configured to hybridize to a polymorphism of the target nucleic acid. In some embodiments, the free end of the 3' hybridization region of the first sensor part or the free end of 5' hybridization region of the second sensor part is configured to hybridize to a polymorphism of the target nucleic acid. In some embodiments, the hybridization sequence of the polymorphism comprises one or both of the most 3' base of the first sensor part hybridization region and the 5' base of the second sensor part hybridization region. In some embodiments, the target nucleic acid hybridization region comprises one or more polymorphisms.

Aspects of the invention describe methods for detecting a target nucleic acid in a sample, comprising a) providing a sample comprising the target nucleic acid; b) contacting sample comprising the target nucleic acid with the nucleic acid sensor system as described herein, in the presence of a ligase under conditions favorable to the hybridization of the target nucleic acid to the 3' hybridization region of the first sensor part and to the 5' hybridization region of the second sensor part of the expression cassette, to thereby generate a reaction product comprising the target nucleic acid hybridized to the first sensor part and the second sensor part operably-linked to each other; c) contacting the reaction product produced in step b) with a cell-free expression system in the presence of a strand displacing DNA Polymerase and a primer, under conditions favorable to the production of a reporter protein; d) contacting reaction product produced in step c) with a reagent enabling the detection of the expression of the reporter protein; e) measuring the expression of the reporter protein produced in step d) to determine the presence and/or amount of the target nucleic acid in the sample. In some embodiments, the ligase is provided as a part of the cell free system.

Aspects of the invention describe methods for detecting a target nucleic acid in a sample, comprising a) providing a sample comprising the target nucleic acid; b) contacting sample comprising the target nucleic acid with the nucleic acid sensor system as described herein, in the presence of a ligase and optionally a primer under conditions favorable to the hybridization of the target nucleic acid sequence to the 3' hybridization region of the first sensor part and to the 5' hybridization region of the second sensor part of the expression cassette, to thereby generate a reaction product comprising the target nucleic acid hybridized to the first sensor part and the second sensor part operably-linked to each other; c) contacting the reaction product produced in step b) with a cell-free expression system in the presence of a strand displacing DNA Polymerase, under conditions favorable to the production of a reporter protein; d) contacting reaction product produced in step c) with a reagent enabling the detection of the expression of the reporter protein; e) measuring the expression of the reporter protein produced in step d) to determine the presence and/or amount of the target nucleic acid in the sample.

Aspects of the invention describe methods for detecting a target nucleic acid in a sample, comprising a) providing a sample comprising the target nucleic acid; b) contacting sample comprising the target nucleic acid with i) the nucleic acid sensor system as described herein, in the presence of a ligase, and ii) a cell-free expression system in the presence of a strand displacing DNA Polymerase and a primer, under conditions favorable to the hybridization of the target nucleic acid to the 3' hybridization region of the first sensor part and to the 5' hybridization region of the second sensor part of the expression cassette, and to the production of a reporter protein; c) contacting reaction product produced in step b) with a reagent enabling the detection of the expression of the reporter protein; d) measuring the expression of the reporter protein produced in step d) to determine the presence and/or amount of the target nucleic acid in the sample. In some embodiments, the ligase is provided as a part of the cell free system. In some embodiments, the ligase is provided as a part of the cell free system.

Aspects of the invention describe methods for detecting a target nucleic acid in a sample, comprising a) providing a sample comprising the target nucleic acid sequence; b) contacting sample comprising the target nucleic acid sequence with i) the nucleic acid sensor system as described herein, in the presence of a ligase, ii) a cell-free expression system in the presence of a strand displacing DNA Polymerase and a primer, and iii) a reagent enabling the detection of the expression of the reporter protein, under conditions favorable to the hybridization of the target nucleic acid to the 3' hybridization region of the first sensor part and to the 5' hybridization region of the second sensor part of the expression cassette, and to the production of a reporter protein; c) measuring the expression of the reporter protein produced in step b) to determine the presence and/or amount of the target nucleic acid in the sample. In some embodiments, the ligase is provided as a part of the cell free system.

Aspects of the invention describe a kit comprising a composition comprising a nucleic acid sensor system in a packaging material, a sample collection device, a positive control and instructions for use.

BRIEF DESCRIPTION OF THE FIGURES

(FIG. 2A) An embodiment of the sensor system with non-template (sense) ssDNA strands and split site after the start codon of the coding sequence. Hybridization region and target RNA are shaded, and 5' phosphate (P) on the B domain is shown. The A domain comprises a promoter, a ribosome binding site (RBS), an ATG start codon, and a 3' hybridization region (shaded). The B domain comprises a 5' phosphate (P), a 5' hybridization domain (shaded), and a coding sequence. The primer is also shown. (FIG. 2B) Alternative sensor component schemes: (i) A and B domains linked at the 5' and 3' ends, respectively; (ii) incorporating the ssDNA primer as a terminal hairpin of B domain; or (iii) including hairpins on both the 5' end of the A domain and the 3' end of the B domain.

FIG. 3: Illustrations showing three versions of the sensor system components. In Version 1, the expression cassette is split into Part A and Part B after the start codon (ATG) of the coding sequence. In Version 2, the expression cassette is split into Part A and Part B between the promoter (P) and ribosome binding site (RBS). In Version 3, the expression cassette is split into Part A and Part B within the coding sequence. Inserted target hybridization regions are shown as hatched boxes for Versions 1 and 2 designs. Version 3 does not include inserted sequence and instead has a target sequence matching the reporter coding sequences flanking the junction site. A primer hybridizing to the 3' end of Part B is shown.

(FIG. 4A) Expression cassettes with two different inserted hybridization regions, AB_T1 and AB_T2, were compared to B part only for the Version 1 system. (FIG. 4B) Expression cassettes with two different inserted hybridization regions, AB_T1 and AB_T2, were compared to B part only for the Version 2 system. (FIG. 4C) The Version 3 expression cassette was compared to the corresponding A part. RLU=relative light units.

(FIG. 5A) The Klenow fragment +exo DNA polymerase was used for primer extension through the ligated junction. (FIG. 5B) The Sequenase™ DNA polymerase was used for primer extension through the ligated junction. Blank=empty well; RLU=relative light units.

(FIG. 11A) Klenow fragment +exo; (FIG. 11B) Klenow fragment-exo; (FIG. 11C) phi29 polymerase; and (FIG. 11D) Sequenase™ DNA polymerases were all effective at activating the expression cassette in the presence of ligase and RNA T2 target (+LT) as compared to reaction without ligase and target (−LT). RLU=relative light units.

(FIG. 14A) Performance of the polymerases (4 units per reaction, unless otherwise specified) in the in vitro detection system targeting the CT target RNA sequence (+RNA) versus a negative control without the target RNA sequence (−RNA). IsoPol (polymerase from *Psychrobacillus*); IsoPol SD+ (polymerase from *Psychrobacillus* with enhanced strand displacement); Bsu (polymerase from *B. subtilis*). RLU=relative light units. (FIG. 14B) Signal to background ratio based on these measurements (S:B ratio) is shown for each polymerase. (FIG. 14C) S:B ratio using different amounts of units of IsoPol SD+, from 1.7 to 4 U.

(FIG. 15A) Activity of the Nluc with the hybridization sequence inserted at the solvent exposed loop regions indicated. (FIG. 15B) ssDNA sensor parts were constructed based on the split locations in A and target CT sequence as described, and these were tested for detection of 100 nM target CT RNA. RLU=relative light units.

Figure 1:
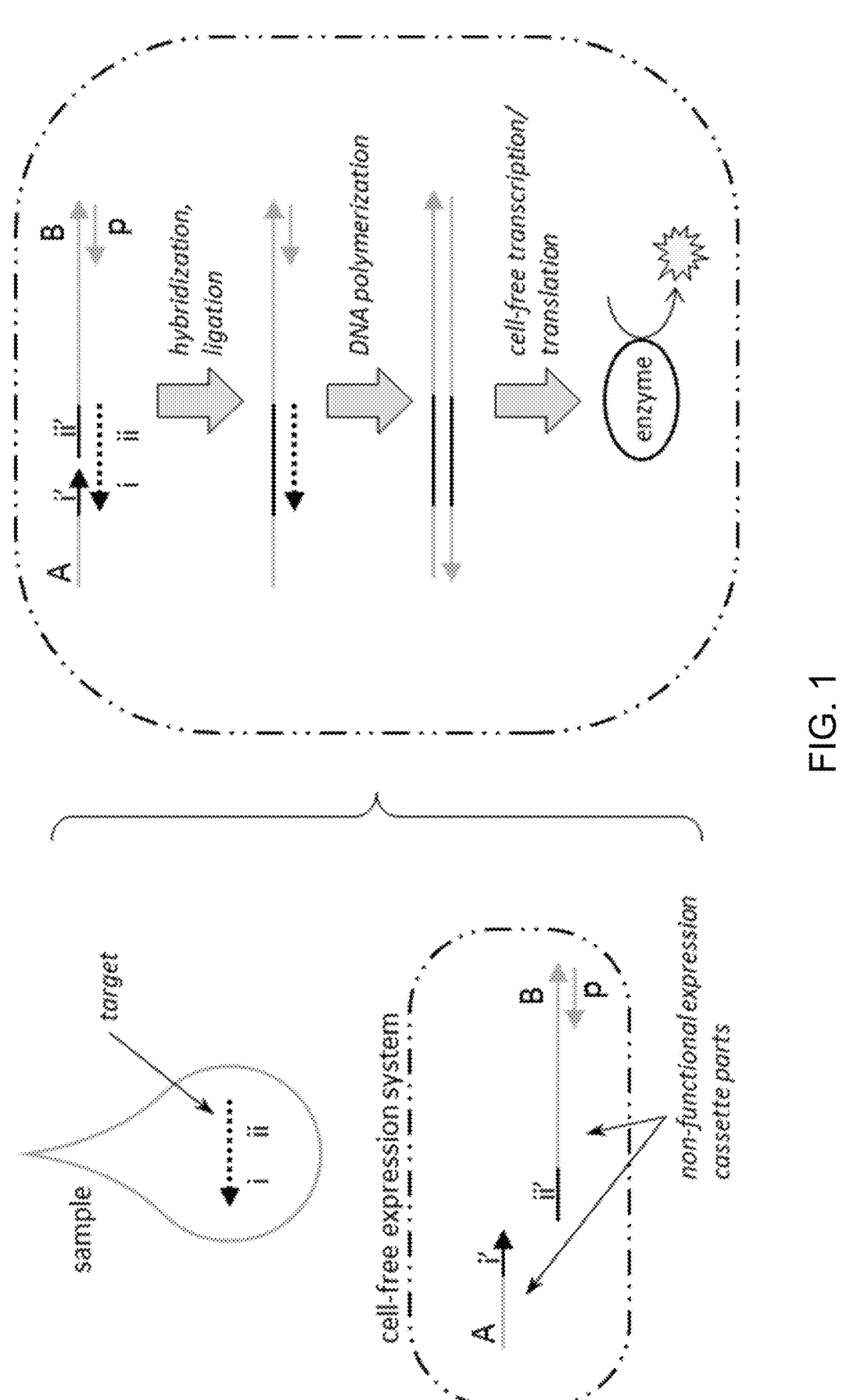
FIG. 1: Illustration of nucleic acid detection technology. A sample containing a target nucleic acid (dashed line) is combined with the nucleic acid sensor parts (A, B, p) in a cell-free expression system. The junction of the sensor parts (i', ii') is designed to hybridize to the target nucleic acid (i, ii) enabling ligation of A and B into a single strand by a ligase. DNA polymerase extends a primer, p, to create a functional, double-stranded expression cassette that is transcribed and translated into a detectable reporter (e.g., an enzyme, or a readily detectible non-catalytic polypeptide) by the cell-free expression system.

The Full Length construct is a complete luciferase containing T7 driven PCR product, while the negative construct is a reaction with no PCR product added.

DETAILED DESCRIPTION OF THE INVENTION

Described herein is a nucleic acid sensor system based on a non-functional, inactive expression cassette designed for activation in the presence of a target nucleic acid. Activation can occur, e.g., by hybridization of multiple separate cassette molecules to a target molecule, thereby bringing the cassette molecules into association and providing a complete cassette which is functional. The active, functional expression cassette is transcribed and translated to an encoded protein or polypeptide in a cell-free expression system. Cell-free expression systems contain cellular machinery operating outside the context of a living cell and without the constraints of a cell membrane. The encoded protein or polypeptide may be detected either directly or indirectly.

A cell-free expression system is an in vitro system that contains all of the molecular machinery, building block components, and energy molecules necessary for protein production from an expression cassette, including transcription of DNA to RNA and the translation of RNA to protein. Molecular machinery necessary for protein production from an expression cassette includes but is not limited to RNA polymerases, ribosomes, and tRNAs. Cell-free expression systems can be based on cell extract, where whole cells are lysed by membrane disruption to enable external expression, or based on transcription and translation machinery purified from cells. In both cases, these systems can be supplemented with building block components such as dNTPs and amino acids together with energy components such as ATP.

As described herein, a promoter, ribosome binding site (RBS), and protein coding sequence of an expression cassette are separated into two single-stranded DNA (ssDNA) nucleic acids or domains. Separation of the expression cassette into two parts (e.g., a first nucleic acid or domain, and a second nucleic acid or domain), and the use of non-template (sense) ssDNA, renders the expression cassette non-functional for transcription and translation of the reporter protein. As used herein, "non-template" indicates the DNA strand that is complementary to the template strand from which mRNA can be transcribed; as such, the non-template strand cannot be directly transcribed into mRNA. As used herein, "sense" indicates that the DNA strand is the same strand as the encoded mRNA. A nucleic acid which "encodes" a particular unit or component is a nucleic acid which comprises the sequence necessary to transcribe (and optionally translate) the specified unit or component. An intervening step of synthesizing a template strand may be necessary for such transcription to occur, but the nucleic acid is still said to encode the unit or component as the genetic information is intrinsic to the nucleic acid's sequence or structure. As used herein, "non-functional" indicates that the DNA strand or molecule cannot be transcribed into mRNA that encodes a reporter protein, as the promoter, RBS, and coding sequence are not all present on the same strand and/or molecule.

The parts of the nucleic acid sensor system are designed so that a target nucleic acid (RNA or ssDNA) can hybridize and bridge the nucleic acids or domains at the hybridization site and/or junction site enabling a ligase to connect the two nucleic acids or domains into a single strand. Subsequent elongation of a 'primer' complementary to a 3' region of the joined/connected/ligated non-template (sense) strand by a DNA polymerase results in the formation of a functional dsDNA expression cassette than can be transcribed by RNA polymerase and translated into a reporter protein (see e.g., FIG. 1).

Described herein is a nucleic acid sensor system, including, a first nucleic acid and a second nucleic acid. The first and second nucleic acids can each be a molecule or a sequence. The first nucleic acid comprises a 3' hybridization region. The 3' hybridization region is located at the 3' end of the first nucleic acid. The 3' hybridization region is complementary to a first region of a target nucleic acid. The second nucleic acid comprises a 5' hybridization region. The 5' hybridization region is located at the 5' end of the second nucleic acid. The 5' hybridization region is complementary to a second region of the target nucleic acid. In some embodiments of any of the aspects, the first and second regions of the target nucleic acid are adjacent, contiguous, and/or consecutive with each other.

The first nucleic acid and the second nucleic acid can be bridged or brought into close proximity by a target nucleic acid. The first region of the target nucleic acid hybridizes to the upstream hybridization region (e.g., 3' hybridization region) of the first nucleic acid. The second region of the target nucleic acid hybridizes to the downstream hybridization region (e.g., 5' hybridization region) of the second nucleic acid. Since the first and second regions of the target nucleic acid are adjacent, contiguous, and/or consecutive with each other, the 3' hybridization region of the first nucleic acid is brought into close proximity to the 5' hybridization region of the second nucleic acid. The 3' hybridization region and the 5' hybridization region, which in some embodiments of any of the aspects includes a 5' phosphate, can be joined, connected or ligated by a ligase. The ligated first and second nucleic acids form a non-template cassette encoding a promoter, a ribosome binding site, and a coding sequence for a reporter protein. In some embodiments of any of the aspects, the first and second nucleic acids, once ligated together by a ligase, are referred to as the first and second domains. The first and second nucleic acids can be separate molecules or sequences, whereas the first and second domains can be located on the same molecule or sequence following hybridization and ligation of the first and second nucleic acids.

In some embodiments of any of the aspects, the first nucleic acid and the second nucleic acid, when ligated together, are configured to encode a non-template cassette comprising a promoter, a ribosome binding site, and a coding sequence for a reporter protein. In some embodiments of any of the aspects, the first nucleic acid and the second nucleic acid, when ligated together and hybridized to a target nucleic acid that hybridizes to the 3' hybridization region and the 5' hybridization region, are configured to encode a non-template cassette comprising a promoter, a ribosome binding site, and a coding sequence for a reporter protein. In some embodiments of any of the aspects, a target nucleic acid hybridization sequence is located within the cassette, and the cassette is separated into a first nucleic acid and second nucleic acid wherein the separation occurs within the hybridization region.

In some embodiments of any of the aspects, the first nucleic acid includes the promoter, and the second nucleic acid includes the coding sequence for a reporter protein. In some embodiments of any of the aspects, the first nucleic acid includes the promoter and ribosome binding site and the second nucleic acid includes the coding sequence for a reporter protein.

In some embodiments of any of the aspects, the system further comprises a primer complementary to a 3' region of the second nucleic acid or complementary to a sequence which is 3' of the coding sequence in the second nucleic acid or domain. In some embodiments of any of the aspects, the system further comprises a primer complementary to a 3' region of the second nucleic acid or complementary to a sequence which is 3' of any promoter, ribosome binding site, or coding sequence in the second nucleic acid or domain. In some embodiments of any of the aspects, the first nucleic acid and the second nucleic acid are DNA. In some embodiments of any of the aspects, the first nucleic acid and the second are ssDNA.

Further described herein is a nucleic acid sensor system, including a) a non-functional, single-stranded, non-template form of a DNA expression cassette including: i) a promoter, ii) a RBS, iii) a coding sequence for a reporter protein, wherein a target nucleic acid hybridization sequence is inserted within the cassette, and the cassette is separated into two nucleic acids, or domains, wherein the separation occurs within the hybridization region, b) a single-stranded DNA primer complementary to a 3' region of the expression cassette or complementary to a sequence which is 3' of the coding sequence in the second nucleic acid or domain, c) a ligase and a cell-free expression system.

Further described herein is a nucleic acid sensor system, including a) a non-functional, single-stranded, non-template form of a DNA expression cassette including: i) a promoter, ii) a RBS, iii) a coding sequence for a reporter protein, wherein a target nucleic acid hybridization sequence is inserted within the cassette, and the cassette is separated into two molecules, sequences, nucleic acids, or domains, wherein the separation occurs within the hybridization region, b) a single-stranded DNA primer complementary to a 3' region of the expression cassette or complementary to a sequence which is 3' of any promoter, ribosome-binding site, or coding sequence in the second nucleic acid or domain, c) a ligase and a cell-free expression system.

Figure 3:
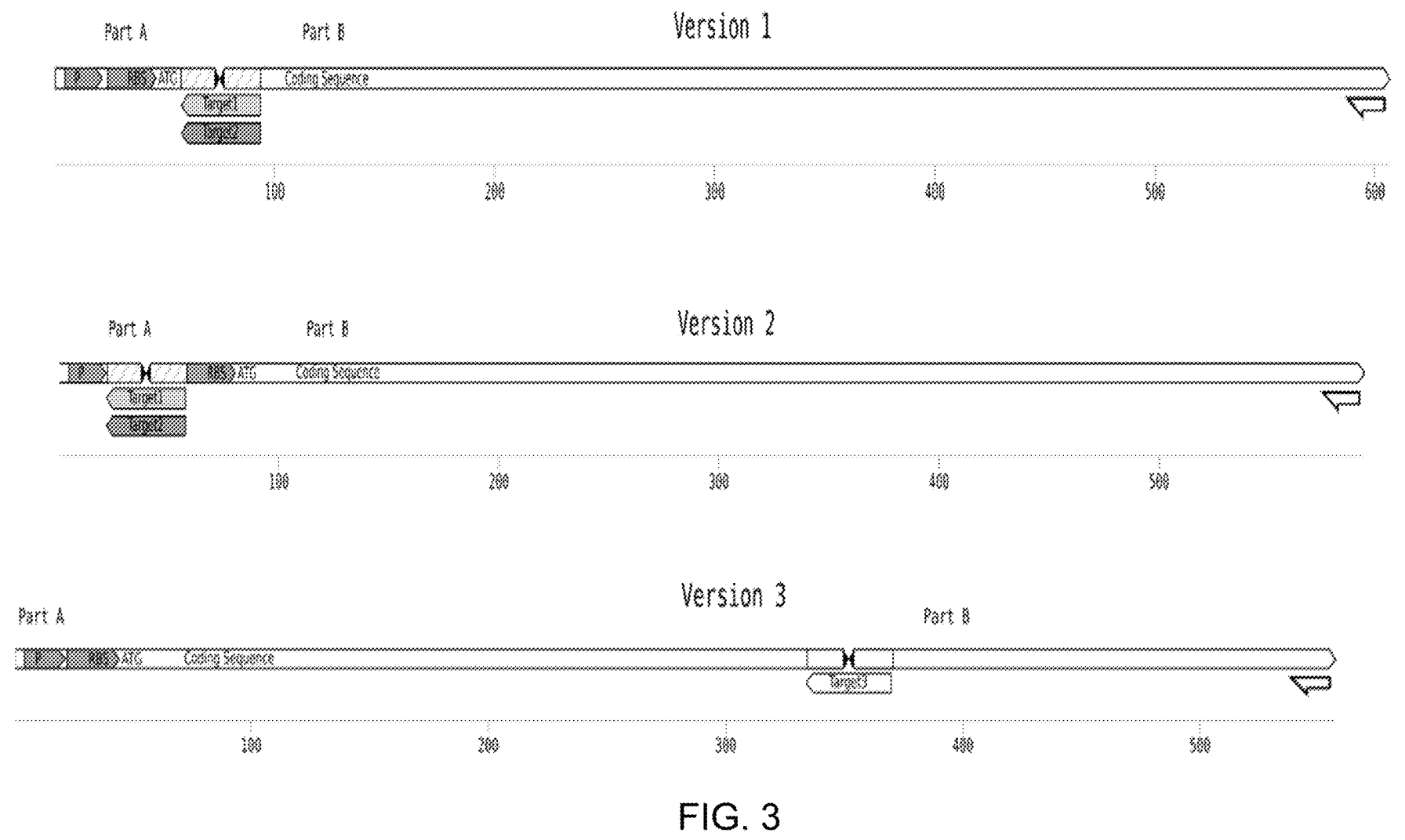

Described herein is a nucleic acid sensor system, referred to in some aspects or embodiments as a version 1 (v1) nucleic acid system (see e.g., FIG. 3). In some embodiments of any of the aspects, the first nucleic acid or domain comprises the promoter, the ribosome binding site, and a start codon of the coding sequence for the reporter protein, and the second nucleic acid or domain comprises the remaining coding sequence for the reporter protein. In some embodiments of any of the aspects, this nucleic acid system comprises a) a first ssDNA nucleic acid or domain including from 5' to 3', a non-template (sense) strand of: i) a promoter, ii) a RBS, iii) a start codon, and iv) a 3' hybridization region, in the form of a reading frame in-frame with the start codon, b) a second ssDNA nucleic acid or domain including from 5' to 3', a non-template (sense) strand of: i) a 5' hybridization region, in the form of a reading frame in-frame with the start codon, and ii) a coding sequence for a reporter protein or polypeptide linked downstream of the hybridization region and in-frame with the start codon, and c) a ssDNA primer complementary to a 3' region of the second nucleic acid or domain.

In some embodiments of any of the aspects, either the first or second nucleic acid or domain comprises the promoter, the ribosome binding site, and a start codon of the coding sequence for the reporter protein, and the remaining nucleic acid or domain comprises the remaining coding sequence for the reporter protein. In some embodiments of any of the aspects, this nucleic acid system comprises a) a first ssDNA nucleic acid or domain including from 5' to 3', a non-template (sense) strand of: i) a promoter, ii) a RBS, iii) a start codon, and iv) an upstream portion of a hybridization region (e.g., 3' hybridization region), in the form of a reading frame in-frame with the start codon, b) a second ssDNA nucleic acid or domain including from 5' to 3', a non-template (sense) strand of: i) a downstream portion of the hybridization region (e.g., 5' hybridization region), in the form of a reading frame in-frame with the start codon, and ii) a coding sequence for a reporter protein linked downstream of the hybridization region and in-frame with the start codon, and c) a ssDNA primer complementary to a 3' region of the second domain.

Further described herein is a nucleic acid sensor system, referred to in some aspects or embodiments as a version 2 (v2) nucleic acid system (see e.g., FIG. 3). In some embodiments of any of the aspects, the first nucleic acid or domain comprises the promoter and the second nucleic acid or domain comprises the ribosome binding site and coding sequence for the reporter protein. In some embodiments of any of the aspects, this nucleic acid system comprises: a) a first ssDNA nucleic acid or domain including from 5' to 3', a non-template (sense) strand of: i) a promoter, and ii) a 3' hybridization region, b) a second ssDNA domain including from 5' to 3', a non-template (sense) strand of: i) a 5' hybridization region, ii) a RBS, and iii) a start codon linked in-frame with a coding sequence for a reporter protein, and c) a ssDNA primer complementary to a 3' region of the second nucleic acid or domain or complementary to a sequence which is 3' of the coding sequence in the second nucleic acid or domain.

In some embodiments of any of the aspects, either the first or second nucleic acid or domain comprises the promoter and the remaining nucleic acid or domain comprises the ribosome binding site and coding sequence for the reporter protein. In some embodiments of any of the aspects, this nucleic acid system comprises: a) a first ssDNA nucleic acid or domain including from 5' to 3', a non-template (sense) strand of: i) a promoter, and ii) an upstream portion of a hybridization region (e.g., 3' hybridization region), b) a second ssDNA domain including from 5' to 3', a non-template (sense) strand of: i) a downstream portion of the hybridization region (e.g., 5' hybridization region), ii) a RBS, and iii) a start codon linked in-frame with a coding sequence for a reporter protein, and c) a ssDNA primer complementary to a 3' region of the second nucleic acid or domain or complementary to a sequence which is 3' of any promoter, ribosome binding site, or coding sequence in the second nucleic acid or domain.

Described herein is a nucleic acid sensor system, referred to in some aspects or embodiments as a version 3 (v3) nucleic acid system (see e.g., FIG. 3). In some embodiments of any of the aspects, first nucleic acid or domain comprises the promoter, the ribosome binding site, and a 5' portion of the coding sequence for the reporter protein, and the second nucleic acid or domain comprises the remaining coding sequence for the reporter protein. In some embodiments of any of the aspects, this nucleic acid system comprises: a) a first ssDNA nucleic acid or domain including from 5' to 3', a non-template (sense) strand of: i) a promoter, ii) a RBS, iii) a start codon linked in-frame with an upstream portion of a coding sequence for a reporter protein, e.g., comprising a start codon and at least one additional codon, and iv) a 3' hybridization region in the form of a reading frame linked downstream of and in-frame with the upstream portion of a coding sequence for a reporter protein, b) a second ssDNA nucleic acid or domain including from 5' to 3', a non-template (sense) strand of: i) a 5' hybridization region in the form of a reading frame in-frame with the start codon, and ii) a downstream portion of a coding sequence for the reporter protein linked downstream of and in-frame with the downstream portion of the hybridization region, and c) a ssDNA primer complementary to the second nucleic acid domain at its 3' end or complementary to a sequence which is 3' of the coding sequence in the second nucleic acid or domain.

In some embodiments of any of the aspects, either the first or second nucleic acid or domain comprises the promoter, the ribosome binding site, and a 5' portion of the coding sequence for the reporter protein, and the remaining nucleic acid or domain comprises the remaining coding sequence for the reporter protein. In some embodiments of any of the aspects, this nucleic acid system comprises: a) a first ssDNA nucleic acid or domain including from 5' to 3', a non-template (sense) strand of: i) a promoter, ii) a RBS, iii) a start codon linked in-frame with an upstream portion of a coding sequence for a reporter protein, e.g., comprising a start codon and at least one additional codon, and iv) an upstream portion of a hybridization region (e.g., 3' hybridization region) in the form of a reading frame linked downstream of and in-frame with the upstream portion of a coding sequence for a reporter protein, b) a second ssDNA nucleic acid or domain including from 5' to 3', a non-template (sense) strand of: i) a downstream portion of the hybridization region (e.g., 5' hybridization region) in the form of a reading frame in-frame with the start codon, and ii) a downstream portion of a coding sequence for the reporter protein linked downstream of and in-frame with the downstream portion of the hybridization region, and c) a ssDNA primer complementary to the second nucleic acid domain at its 3' end or complementary to a sequence which is 3' of any promoter, ribosome binding site, or coding sequence in the second nucleic acid or domain.

In some embodiments of any of the aspects, the 3' hybridization region and 5' hybridization region are located in the coding sequence of the reporter protein or polypeptide (e.g., the v3 nucleic acid sensor system). In some embodiments of any of the aspects, the 3' hybridization region and 5' hybridization region are located within a region encoding for a solvent exposed loop of the reporter protein. As used herein, a "solvent exposed loop" refers to a region of a protein that is on the external (solvent) side of a protein. A solvent exposed loop can be more conformationally flexible than other regions of the protein. A solvent exposed loop can represent an optimal site for insertion of an exogenous nucleic acid sequence or sequences (e.g., the 3' and 5' hybridization regions). Inserting an exogenous nucleic acid sequence into a solvent exposed loop could be more likely to not disrupt the protein's normal structure and or function. By way of non-limiting example, specific solvent-exposed loop sites tested or used for insertion of the 3' and 5' hybridization regions into Nanoluciferase include E50-N51, L66-S67, G123-K124, G135-N136, or N145-P146 (see e.g., Example 17). As another non-limiting example, specific solvent-exposed loop sites tested or used for insertion of the 3' and 5' hybridization regions into Nanoluciferase include Y17-N18, G26-G27, S29-S30, G36-G37, E50-N51, L66-S67, K79-V80, D86-H87, D101-G102, R113-P114, G123-K124, G135-N136, N145-P146, and N157-G148 (see e.g., Example 18). In some embodiments of any of the aspects, the 3' hybridization region and 5' hybridization region are located in the coding sequence of the reporter protein and do not substantially impact reporter gene function, or in structured regions that enable detection via protein-protein or protein-small molecule interaction.

In some embodiments of any of the aspects, at least a portion of the 3' hybridization region is in the promoter, the ribosome binding site, or the coding sequence. In some embodiments of any of the aspects, at least a portion of the 5' hybridization region is in the promoter, the ribosome binding site, or the coding sequence. In some embodiments of any of the aspects, the 3' hybridization region is not within or co-extensive with the promoter, the ribosome binding site, or the coding sequence. In some embodiments of any of the aspects, the 3' hybridization region is 3' of any promoter, ribosome binding site, or coding sequence in the first nucleic acid or domain. In some embodiments of any of the aspects, the 5' hybridization region is not within or co-extensive with the promoter, the ribosome binding site, or the coding sequence. In some embodiments of any of the aspects, the 5' hybridization region is 5' of any promoter, ribosome binding site, or coding sequence in the second nucleic acid.

In various embodiments of the aforementioned, the first and second ssDNA nucleic acids or domains are separate DNA fragments and the second ssDNA nucleic acid or domain includes a 5' phosphate. In some embodiments of any of the aspects, the second ssDNA nucleic acid or domain further includes a nucleotide sequence or linker at its 3' end including the ssDNA primer in a terminal hairpin loop (see e.g., FIG. 2B (ii) or FIG. 2B (iii)). In some embodiments of any of the aspects, the 5' end of the first nucleic acid or domain further includes a sequence or linker that forms a terminal hairpin loop (see e.g., FIG. 2B (iii)). In some embodiments of any of the aspects, the 5' end of the first nucleic acid or domain is linked to the 3' end of the second nucleic acid or domain through intervening ssDNA sequences so that the first and second domains are present on a single ssDNA sequence (see e.g., FIG. 2B (i)).

In some embodiments of any of the aspects, the full hybridization region (e.g., both of the 3' and 5' hybridization regions) is at least 12-60 nucleotides. In some embodiments of any of the aspects, the full hybridization region is at least 12 to 40 nucleotides. In some embodiments of any of the aspects, the full hybridization region is at least 12 to 36 nucleotides. In some embodiments of any of the aspects, the full hybridization region is at least 12 nucleotides. In some embodiments of any of the aspects, the 3' hybridization region (e.g., the upstream portion of the hybridization region) and the 5' hybridization region (e.g., the downstream portion of the hybridization region) are each at least 6-20 nucleotides. In some embodiments of any of the aspects, the 3' hybridization region and the 5' hybridization region are each at least 6-18 nucleotides. In some embodiments of any of the aspects, the 3' hybridization region and the 5' hybridization region are each at least 18 nucleotides. In some embodiments of any of the aspects, the 3' hybridization region and the 5' hybridization region are each at least 6 nucleotides.

In some embodiments of any of the aspects, the 3' hybridization region and the 5' hybridization region are complementary to a portion of the target nucleic acid such that hybridization of the target nucleic acid to the 3' and 5' hybridization regions creates a junction between the first and second nucleic acids or domains sufficient for productive ligation to occur.

In some embodiments of any of the aspects, the hybridization regions and the complementary targeted portion of the target nucleic acid are complementary by 80 to 85%, 85% to 90%, 90 to 95%, 95 to 99%, or 99% or more percent identity, wherein percent identity is established by selecting a comparison window between two sequences of n nucleotides, and the degree of complementary base pairs within the comparison is divided by n nucleotides in the comparison window, or any other technique for determining percent identity readily known to one of ordinary skill. A junction of the nucleic acids or domains can refer to a point at which the two molecules or domains are in physical contact, or positioned such that ligation of the two molecules or domains are capable of being ligated to each other at the junction.

In some embodiments of any of the aspects, the nucleic acid sensor system includes a primer complementary to a 3' region of the second nucleic acid. In some embodiments of any of the aspects, the primer is complementary to a sequence which is 3' of the coding sequence in the second nucleic acid or domain. In some embodiments of any of the aspects, the primer is complementary to a sequence which is 3' of any promoter, ribosome binding site, or coding sequence in the second nucleic acid or domain. In some embodiments of any of the aspects, the primer is ssDNA. In some embodiments of any of the aspects, the primer binds to the second nucleic acid or domain and allows for DNA polymerization of the template strand that is complementary to the non-template strand. In some embodiments of any of the aspects, the primer is SEQ ID NO: 19.

Reporter proteins are those which provide a detectable signal and/or comprise the ability to generate a detectable signal (e.g. by catalyzing reaction converting a compound to a detectable product, or binding to another molecule that enables detection). Detectable signals can comprise, for example, fluorescence or luminescence. Detectable signals, methods of detecting them, and methods of incorporating them into reagents (e.g. polypeptides comprising a reporter protein) are well known in the art. In some embodiments of any of the aspects, detectable signals can include signals that can be detected by spectroscopic, photochemical, biochemical, immunochemical, electromagnetic, radiochemical, or chemical means, such as fluorescence, chemifluorescence, or chemiluminescence, or any other appropriate means. In some embodiments of any of the aspects, the reporter protein is selected from the group consisting of luciferase, nanoluciferase, beta-lactamase, beta-galactosidase, horseradish peroxidase, alkaline phosphatase, catalase, carbonic anhydrase, green fluorescent protein, red fluorescent protein, cyan fluorescent protein, yellow fluorescent protein, trypsin, a protease, a peptide that complements and activates a truncated reporter protein, a kinase.

In some embodiments of any of the aspects, the systems include one or more of ligase, a RNA polymerase, a strand-displacing DNA polymerase, dNTPs, RNAse inhibitor, and a cell free expression system. In some embodiments of any of the aspects, the systems may also include a reverse transcriptase with a functional RNaseH domain. In some embodiments of any of the aspects, the systems may include separate reverse transcriptase and RNaseH activities. In some embodiments of any of the aspects, the cell free expression system is whole cell extract.

As described herein, the nucleic acid system can comprise: a) a single-stranded DNA (ssDNA) primer complementary to i) a 3' region of the expression cassette, ii) a 3' region of the second nucleic acid or domain, iii) a sequence which is 3' of the coding sequence in the second nucleic acid or domain, or iv) a sequence which is 3' of any promoter, ribosome binding site, or coding sequence in the expression cassette; b) a ligase; and/or c) a cell-free expression system.

As described herein, the nucleic acid system can comprise: a) a single-stranded DNA (ssDNA) primer complementary to i) a 3' region of the expression cassette, ii) a 3' region of the second nucleic acid or domain, iii) a sequence which is 3' of any promoter, ribosome binding site, or coding sequence in the second nucleic acid or domain, or iv) a sequence which is 3' of any promoter, ribosome binding site, or coding sequence in the expression cassette; b) a ligase; and/or c) a cell-free expression system.

As used herein, a "polymerase" refers an enzyme that catalyzes the synthesis of long nucleic acids. As used herein, a "strand-displacing polymerase" refers to a polymerase which has the ability to displace or dislodge downstream DNA or RNA (e.g., the target DNA or RNA hybridized to the nucleic acid sensor system) encountered during synthesis. DNA polymerases exhibit varying degrees of strand displacement activity. DNA polymerases with low strand-displacement activity are often unable to synthesize DNA past a downstream DNA or RNA, potentially resulting in incomplete DNA polymerization. DNA polymerases with high strand-displacement activity are often able to synthesize DNA past a downstream DNA or RNA, resulting in complete DNA polymerization. In some embodiments of any of the aspects, the strand displacing DNA polymerase is selected from the group consisting of a Klenow fragment with exonuclease portion, a Klenow fragment without the exonuclease portion, a phi29 polymerase, a modified T7 DNA polymerase, a polymerase from *Psychrobacillus*, a polymerase from *Psychrobacillus* with enhanced strand displacement, and a polymerase from *B. subtilis* (see e.g., Example 13, Example 16).

In some embodiments of any of the aspects, the junction (e.g., the 3' or 5' hybridization region) is configured to hybridize against a polymorphism of the target nucleic acid. In some embodiments of any of the aspects, the free end of the junction or the 3' or 5' hybridization region is configured to hybridize to a polymorphism of the target nucleic acid. In some embodiments of any of the aspects, the polymorphism is located at one or both of the two bases at the junction of the hybridization region, on either or both the upstream or downstream ssDNA sensor domain. In some embodiments of any of the aspects, one or more polymorphisms may be optionally introduced within the hybridization region. As a non-limiting example, four different exemplary variants (polymorphisms) were tested (see e.g., Example 15).

In some embodiments of any of the aspects, the first and second nucleic acids can be separate molecules or sequences. In some embodiments of any of the aspects, the first and second nucleic acids, when ligated together, after being ligated together, or after being ligated together by a ligase, are referred to as the first and second domains. The first and second nucleic acids can be separate molecules or sequences, whereas the first and second domains can be located on the same molecule or sequence following hybridization and ligation of the first and second nucleic acids.

In some embodiments, one or more components of the nucleic acid sensor systems described herein can be conjugated to a solid substrate. The solid substrate can be selected from a group consisting of: a bead, a magnetic microbead, a paramagnetic microbead, a microporous membrane, a hollow fiber, any other fluid filtration membrane, a flow device, a microtiter plate, a test tube, a cell culture plate, a microarray plate, glass beads, latex beads, a living cell, an extracellular matrix of a biological tissue or organ, and a phagocyte. In some embodiments of any of the aspects, the solid substrate can be attached or conjugated to the first nucleic acid, the second nucleic acid, the first domain, the second domain, the primer, and/or the target nucleic acid. In some embodiments of any of the aspects, the solid substrate is attached or conjugated to the first nucleic acid and/or the second nucleic acid.

As used herein, "components of the nucleic acid sensor system" refers to the first part, the second part, or the first nucleic acid, the second nucleic acid, or the first domain, the second domain, or A domain, B domain, or first sequence, second sequence, and/or the primer, and/or the target nucleic acid. Without limitations, exemplary types of substrates that can be employed include, but are not limited to a nucleic acid scaffold, a biological molecule (e.g., a living cell), or a solid surface. In some embodiments of any of the aspects, the solid surface can be functionalized with a coupling molecule, e.g., an amino group, to facilitate the conjugation of components of the nucleic acid sensor system to the solid surface.

The attachment of components of the nucleic acid sensor system to a substrate surface can be performed with multiple approaches, for example, by direct cross-linking the components of the nucleic acid sensor system to the substrate surface; cross-linking the components of the nucleic acid sensor system to the substrate surface via a nucleic acid matrix (e.g., DNA matrix or DNA/oligonucleotide origami structures); cross-linking the components of the nucleic acid sensor system to the substrate surface via a dendrimer-like structure (e.g., PEG/Chitin-structure); attracting magnetic microbeads coated with components of the nucleic acid sensor system to the substrate surface with a focused magnetic field gradient applied to the substrate surface, attaching components of the nucleic acid sensor system to a substrate via biotin-avidin or biotin-avidin-like interaction, or any other art-recognized methods.

The components of the nucleic acid sensor system can be adapted for orienting the hybridization region away from the substrate. A component of the nucleic acid sensor system can comprise a nucleic acid sequence or polypeptide sequence which binds to a target sequence or binding partner on the solid substrate. Alternatively, or additionally, the surface of a substrate can be functionalized to include coupling molecules described herein. As used herein, the term "coupling molecule" refers to any molecule or any functional group that is capable of selectively binding with a component of the nucleic acid sensor system described herein. Representative examples of coupling molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule, such as biotin and avidin. The coupling molecules need not comprise an entire naturally occurring molecule but may consist of only a portion, fragment or subunit of a naturally or non-naturally occurring molecule, as for example the Fab fragment of an antibody. The coupling molecule can further comprise a detectable label. The coupling molecule can also encompass various functional groups that can couple the substrate to the components of the nucleic acid sensor system. Examples of such functional groups include, but are not limited to, an amino group, a carboxylic acid group, an epoxy group, and a tosyl group.

In some embodiments of any of the aspects, the components of the nucleic acid sensor system can be conjugated to a substrate surface through a covalent or non-covalent interaction. The component of the nucleic acid sensor system- and/or coupling molecule can be conjugated to the surface of a solid substrate covalently or non-covalently using any of the methods known to those of skill in the art. For example, covalent immobilization can be accomplished through, for example, silane coupling. See, e.g., Weetall, 15 Adv. Mol. Cell Bio. 161 (2008); Weetall, 44 Meths. Enzymol. 134 (1976). The covalent interaction between the components of the nucleic acid sensor system and/or coupling molecule and the surface can also be mediated by other art-recognized chemical reactions, such as NHS reaction or a conjugation agent. The non-covalent interaction between the component of the nucleic acid sensor system and/or coupling molecule and the surface can be formed based on ionic interactions, van der Waals interactions, dipole-dipole interactions, hydrogen bonds, electrostatic interactions, and/or shape recognition interactions.

Without limitations, conjugation can include either a stable or a labile (e.g. cleavable) bond or conjugation agent. Exemplary conjugations include, but are not limited to, covalent bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, temperature sensitive, radiation (IR, near-IR, UV) sensitive bond or conjugation agent, pH-sensitive bond or conjugation agent, non-covalent bonds (e.g., ionic charge complex formation, hydrogen bonding, pi-pi interactions, cyclodextrin/adamanty host guest interaction) and the like.

As used herein, the term "conjugation agent" means an organic moiety that connects two parts of a compound. Linkers typically comprise a direct bond or an atom such as oxygen or sulfur, a unit such as NR1, C(O), C(O)NH, SO, SO2, SO2NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroaryl-alkynyl, heterocyclylalkyl, heterocyclylalkenyl, heterocy-clylalkynyl, aryl, heteroaryl, heterocyclyl, cycloalkyl, cycloalkenyl, alkylarylalkyl, alkylarylalkenyl, alkylarylal-kynyl, alkenylarylalkyl, alkenylarylalkenyl, alkenylarylal-kynyl, alkynylarylalkyl, alkynylarylalkenyl, alkynylarylal-kynyl, alkylheteroarylalkyl, alkylheteroarylalkenyl, alkylheteroarylalkynyl, alkenylheteroarylalkyl, alkenylhet-eroarylalkenyl, alkenylheteroarylalkynyl, alkynylheteroary-lalkyl, alkynylheteroarylalkenyl, alkynylheteroarylalkynyl, alkylheterocyclylalkyl, alkylheterocyclylalkenyl, alkyl-hererocyclylalkynyl, alkenylheterocyclylalkyl, alkenylhet-erocyclylalkenyl, alkenylheterocyclylalkynyl, alkynylhet-erocyclylalkyl, alkynylheterocyclylalkenyl, alkynylheterocyclylalkynyl, alkylaryl, alkenylaryl, alky-nylaryl, alkylheteroaryl, alkenylheteroaryl, alkynyl-hereroaryl, where one or more methylenes can be interrupted or terminated by O, S, S(O), SO2, NH, C(O)N(R1) 2, C(O), cleavable linking group, substituted or unsubstituted aryl, substituted or unsubstituted heteroaryl, substituted or unsub-stituted heterocyclic; where R1 is hydrogen, acyl, aliphatic or substituted aliphatic.

Without limitations, any conjugation chemistry known in the art for conjugating two molecules or different parts of a composition together can be used for linking at least one component of the nucleic acid sensor system to a substrate. Exemplary coupling molecules and/or functional groups for conjugating at least one component of the nucleic acid sensor system to a substrate include, but are not limited to, a polyethylene glycol (PEG, NH2-PEGX-COOH which can have a PEG spacer arm of various lengths X, where 1<X<100, e.g., PEG-2K, PEG-5K, PEG-10K, PEG-12K, PEG-15K, PEG-20K, PEG-40K, and the like), maleimide conjugation agent, PASylation, HESylation, Bis(sulfosuccinimidyl) suberate conjugation agent, DNA conjugation agent, peptide conjugation agent, silane conjugation agent, polysaccharide conjugation agent, hydrolyzable conjugation agent, and any combinations thereof.

In alternative embodiments, the components of the nucleic acid sensor system can be conjugated onto the surface of the solid substrate by a coupling molecule pair. The terms "coupling molecule pair" and "coupling pair" as used interchangeably herein refer to the first and second molecules that specifically bind to each other. One member of the binding pair is conjugated with the solid substrate while the second member is conjugated with the component of the nucleic acid sensor system. As used herein, the phrase "first and second molecules that specifically bind to each other" refers to binding of the first member of the coupling pair to the second member of the coupling pair with greater affinity and specificity than to other molecules.

Exemplary coupling molecule pairs include, without limi-tations, any haptenic or antigenic compound in combination with a corresponding antibody or binding portion or frag-ment thereof (e.g., digoxigenin and anti-digoxigenin; mouse immunoglobulin and goat anti-mouse immunoglobulin) and non-immunological binding pairs (e.g., biotin-avidin, biotin-streptavidin), hormone (e.g., thyroxine and cortisol-hor-mone binding protein), receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleotide pairs capable of forming nucleic acid duplexes). The coupling molecule pair can also include a first molecule that is negatively charged and a second molecule that is positively charged.

One example of using coupling pair conjugation is the biotin-avidin or biotin-streptavidin conjugation. In this approach, one of the members of the coupling pair (e.g., a portion of the component of the nucleic acid sensor system such as the 5' end, or a substrate) is biotinylated and the other (e.g., a substrate or the component of the nucleic acid sensor system) is conjugated with avidin or streptavidin. Many commercial kits are also available for biotinylating mol-ecules, such as nucleic acids or proteins. For example, an aminooxy-biotin (AOB) can be used to covalently attach biotin to a molecule with an aldehyde or ketone group. In one embodiment, AOB is attached to the substrate-binding domain (e.g., comprising AKT oligopeptide) of the compo-nents of the nucleic acid sensor system.

One non-limiting example of using conjugation with a coupling molecule pair is the biotin-sandwich method. See, e.g., Davis et al., 103 PNAS 8155 (2006). The two mol-ecules to be conjugated together are biotinylated and then conjugated together using tetravalent streptavidin. In addi-tion, a peptide can be coupled to the 15-amino acid sequence of an acceptor peptide for biotinylation (referred to as AP; Chen et al., 2 Nat. Methods 99 (2005)). The acceptor peptide sequence allows site-specific biotinylation by the *E. coli* enzyme biotin ligase (BirA; Id.). A component of the nucleic acid sensor system can be similarly biotinylated for conju-gation with a solid substrate. Many commercial kits are also available for biotinylating nucleic acids or proteins. Another example for conjugation to a solid surface would be to use PLP-mediated bioconjugation. See, e.g., Witus et al., 132 JACS 16812 (2010). As described earlier, an AKT sequence conjugated to the 5' end of a component of the nucleic acid sensor system can allow the substrate binding domain to be biotinylated at a single site and further conjugated to the streptavidin-coated solid surface.

Still another example of using coupling pair conjugation is double-stranded nucleic acid conjugation. In this approach, one of the members of the coupling pair (e.g., a component of the nucleic acid sensor system) can be conjugated with a first strand of the double-stranded nucleic acid and the other (e.g., a substrate, or component of the nucleic acid sensor system) is conjugated with the second strand of the double-stranded nucleic acid. Nucleic acids can include, without limitation, defined sequence segments and sequences comprising nucleotides, ribonucleotides, deoxyribonucleotides, nucleotide analogs, modified nucleotides and nucleotides comprising backbone modifications, branch points and non-nucleotide residues, groups or bridges.

In some embodiments of any of the aspects, the linker can comprise at least one cleavable linking group. A cleavable linking group is one which is sufficiently stable under one set of conditions, but which is cleaved under a different set of conditions to release the two parts the linker is holding together.

Cleavable linking groups are susceptible to cleavage agents, e.g., hydrolysis, pH, redox potential or the presence of degradative molecules. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases. A linker can include a cleavable linking group that is cleavable by a particular enzyme. The type of cleavable linking group incorporated into a linker can depend on the cell, organ, or tissue to be targeted.

Exemplary cleavable linking groups include, but are not limited to, hydrolyzable linkers, redox cleavable linking groups (e.g., —S—S— and —C(R)2—S—S—, wherein R is H or C1—C6 alkyl and at least one R is C1-C6 alkyl such as CH3 or CH2CH3); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S) (OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S) (H)—S—, wherein R is optionally substituted linear or branched C1-C10 alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHRAC(O)NHCHRBC(O)—, where RA and RB are the R groups of the two adjacent amino acids). A peptide based cleavable linking group comprises two or more amino acids. In some embodiments of any of the aspects, the peptide-based cleavage linkage comprises the amino acid sequence that is the substrate for a peptidase or a protease. In some embodiments of any of the aspects, an acid cleavable linking group is cleavable in an acidic environment with a pH of about 6.5 or lower (e.g., about 6.5, 6.0, 5.5, 5.0, or lower), or by agents such as enzymes that can act as a general acid.

Activation agents can be used to activate the components to be conjugated together (e.g., surface of a substrate). Without limitations, any process and/or reagent known in the art for conjugation activation can be used. Exemplary surface activation method or reagents include, but are not limited to, 1-Ethyl-3-[3-dimethylaminopropyl]carbodiimide hydrochloride (EDC or EDAC), hydroxybenzotriazole (HOBT), N-Hydroxysuccinimide (NHS), 2-(1H-7-Azabenzotriazol-1-yl)-1,1,3,3-tetramethyl uronium hexafluorophosphate methanaminium (HATU), silanization, surface activation through plasma treatment, and the like.

Again, without limitations, any art known reactive group can be used for coupling. For example, various surface reactive groups can be used for surface coupling including, but not limited to, alkyl halide, aldehyde, amino, bromo or iodoacetyl, carboxyl, hydroxyl, epoxy, ester, silane, thiol, and the like.

In some embodiments of any of the aspects, the systems and/or conditions described herein can be provided with a positive control. As used herein, a positive control is a reaction that is known to produce results or generate a reaction product. As an example, a positive control can be Target 1 or T1 (SEQ ID NO: 20) and a nucleic acid system known to hybridize to T1. Nucleic acid systems known to hybridize to T1 include but are not limited to v1_A_T7 (SEQ ID NO: 1) and v1_B_T7 (SEQ ID NO: 2); v1_CSs_T7 (SEQ ID NO: 6); v2_A_T7 (SEQ ID NO: 9) and v2_B_T7 (SEQ ID NO: 10); v3_A_T7 (SEQ ID NO: 13) and v3_B_T7 (SEQ ID NO: 14). As another example, a positive control can be Target 2 or T2 (SEQ ID NO: 21) and a nucleic acid system known to hybridize to T2. Nucleic acid systems known to hybridize to T2 include but are not limited to v1_A_T2 (SEQ ID NO: 3) and v1_B_T2 (SEQ ID NO: 5); v1_A2_T2 (SEQ ID NO: 4) and v1_B_T2 (SEQ ID NO: 5); v1_CSt_T2 (SEQ ID NO: 7); v1_CSs_T2 (SEQ ID NO: 8); v2_A_T2 (SEQ ID NO: 11) and v2_B_T2 (SEQ ID NO: 12); v3_A_T2 (SEQ ID NO: 15) and v3_B_T2 (SEQ ID NO: 16). As another example, a positive control can be Target 3 or T3 (SEQ ID NO: 22) and a nucleic acid system known to hybridize to T3. Nucleic acid systems known to hybridize to T2 include but are not limited to v3_A_T3 (SEQ ID NO: 17) and v3_B_T3 (SEQ ID NO: 18).

In some embodiment of any of the aspects, a system or composition described herein can be provided in a kit. In various embodiments, the kit includes instructions for use. The kit is an assemblage of materials or components, including at least one of the nucleic acid sensor systems described herein. The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals. In some embodiments, the kit is configured for agricultural applications, treating for example crop diseases, or detecting traits. In some embodiments, the kit is configured for industrial applications. In some embodiments, the kit is configured for consumer applications, for example at-home testing.

Instructions for use may be included in the kit. "Instructions for use" typically include a tangible expression describing the technique to be employed in using the components of the kit to affect a desired outcome in a subject. Still in accordance with the present invention, "instructions for use" may include a tangible expression describing the preparation of a nucleic acid sensor systems and/or at least one method parameter, such as the relative amounts of nucleic acid sensor systems, dosage requirements and administration instructions, and the like, typically for an intended purpose. Optionally, the kit also contains other useful components, such as, measuring tools, diluents, buffers, sample collection device (e.g. swabs), instructions for use, and/or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging may also preferably provide an environment that protects from light, humidity, and oxygen. As used herein, the term "package" refers to a suitable solid matrix or material such as glass, plastic, paper, foil, polyester (such as polyethylene terephthalate, or Mylar) and the like, capable of holding the individual kit components in a format suitable for use. Thus, for example, a package can be a glass vial, plastic vial, or lateral flow strip used to contain suitable quantities of a composition containing a volume of a nucleic acid sensor systems described herein. The packaging material generally has an external label which indicates the contents and/or purpose of the kit and/or its components.

Described herein is a method for detecting a target nucleic acid in a sample, including a) providing the aforementioned nucleic acid sensor systems, in which the upstream hybridization region (e.g., 3' hybridization region) and downstream hybridization region (e.g., 5' hybridization region) are complementary to a portion of the target nucleic acid such that hybridization of the target nucleic acid to the upstream and downstream hybridization regions creates a junction between the first and second nucleic acids or domains sufficient for productive ligation to occur to thereby operatively link all components; b) contacting the nucleic acid sensor system with the sample in the presence of ligase under conditions appropriate for hybridization of the target nucleic acid with the upstream hybridization region (e.g., 3' hybridization region) and downstream hybridization region (e.g., 5' hybridization region) and ligation of the upstream hybridization region (e.g., 3' hybridization region) and downstream hybridization region (e.g., 5' hybridization region), to thereby produce a reaction product; c) contacting the reaction product produced in step b) to a cell free expression system including a strand displacing DNA polymerase, dNTPs and other building block materials necessary for protein production, and a ssDNA primer under conditions appropriate for DNA polymerization, transcription and translation to thereby produce a reaction product, wherein the reaction product is a polypeptide or enzyme; d) measuring directly or indirectly the presence of the polypeptide or enzyme reaction product of step c) compared to that of an appropriate control, wherein significant reaction product presence indicates the presence of the target nucleic acid in the sample.

Described herein is a method for detecting a target nucleic acid in a sample, including a) providing the aforementioned nucleic acid sensor systems, in which the upstream hybridization region (e.g., 3' hybridization region) and downstream hybridization region (e.g., 5' hybridization region) are complementary to a portion of the target nucleic acid such that hybridization of the target nucleic acid to the upstream and downstream hybridization regions creates a junction between the first and second nucleic acids or domains sufficient for productive ligation to occur to thereby operatively link all components; b) contacting the nucleic acid sensor system with the sample in the presence of ligase under conditions appropriate for hybridization of the target nucleic acid with the upstream hybridization region (e.g., 3' hybridization region) and downstream hybridization region (e.g., 5' hybridization region) and ligation of the upstream hybridization region (e.g., 3' hybridization region) and downstream hybridization region (e.g., 5' hybridization region), to thereby produce a reaction product; c) contacting the reaction product produced in step b) to a cell free expression system including a strand displacing DNA polymerase, dNTPs and other building block materials necessary for protein production, and a ssDNA primer under conditions appropriate for DNA polymerization, transcription and translation to thereby produce an operably-linked ssDNA reaction product; d) measuring reporter protein present in the reaction product of step c) compared to that of an appropriate control, wherein significant reporter protein presence indicates the presence of the target nucleic acid in the sample.

As used herein, "appropriate control" can refer to a reference sample which may be a positive or a negative control. As described herein, a positive control is a reaction that is known to produce results. A negative control is a reaction that is known to produce no results or background level detection in the absence of a target sequence. For example, a negative control can include a reaction without a target nucleic acid, with a non-target nucleic acid, or missing one or more components of the nucleic acid sensor system.

In some embodiments of any of the aspects, the nucleic acid sensor system components are each present at about 2 to about 500 nM. In some embodiments of any of the aspects, the nucleic acid sensor system components are each present at about 16 nM. In some embodiments of any of the aspects, the nucleic acid sensor system components are each present at about 2 nM, at about 4 nM, at about 6 nM, at about 8 nM, at about 10 nM, at about 12 nM, at about 14 nM, at about 16 nM, at about 18 nM, at about 20 nM, at about 22 nM, at about 24 nM, 26 nM, at about 28 nM, at about 30 nM, at about 32 nM, at about 34 nM, at about 36 nM, at about 38 nM, at about 40 nM, at about 42 nM, at about 44 nM, 46 nM, at about 48 nM, or at about 50 nM. In some embodiments of any of the aspects, the nucleic acid sensor system components are each present at about 60 nM, at about 70 nM, at about 80 nM, at about 90 nM, at about 100 nM, at about 110 nM, at about 120 nM, at about 130 nM, at about 140 nM, at about 150 nM, at about 160 nM, at about 170 nM, at about 180 nM, at about 190 nM, at about 200 nM, at about 210 nM, at about 220 nM, at about 230 nM, at about 240 nM, at about 250 nM, at about 260 nM, at about 270 nM, at about 280 nM, at about 290 nM, at about 300 nM, at about 310 nM, at about 320 nM, at about 330 nM, at about 340 nM, at about 350 nM, at about 360 nM, at about 370 nM, at about 380 nM, at about 390 nM, at about 400 nM, at about 410 nM, at about 420 nM, at about 430 nM, at about 440 nM, at about 450 nM, at about 460 nM, at about 470 nM, at about 480 nM, at about 490 nM, or at about 500 nM In some embodiments of any of the aspects, the nucleic acid sensor system components are each present at 2 to 500 nM. In some embodiments of any of the aspects, the nucleic acid sensor system components are each present at 16 nM. In some embodiments of any of the aspects, the nucleic acid sensor system components are each present at 2 nM, at 4 nM, at 6 nM, at 8 nM, at 10 nM, at 12 nM, at 14 nM, at 16 nM, at 18 nM, at 20 nM, at 22 nM, at 24 nM, 26 nM, at 28 nM, at 30 nM, at 32 nM, at 34 nM, at 36 nM, at 38 nM, at 40 nM, at 42 nM, at 44 nM, 46 nM, at 48 nM, or at 50 nM. In some embodiments of any of the aspects, the nucleic acid sensor system components are each present at 60 nM, at 70 nM, at 80 nM, at 90 nM, at 100 nM, at 110 nM, at 120 nM, at 130 nM, at 140 nM, at 150 nM, at 160 nM, at 170 nM, at 180 nM, at 190 nM, at 200 nM, at 210 nM, at 220 nM, at 230 nM, at 240 nM, at 250 nM, at 260 nM, at 270 nM, at 280 nM, at 290 nM, at 300 nM, at 310 nM, at 320 nM, at 330 nM, at 340 nM, at 350 nM, at 360 nM, at 370 nM, at 380 nM, at 390 nM, at 400 nM, at 410 nM, at 420 nM, at 430 nM, at 440 nM, at 450 nM, at 460 nM, at 470 nM, at 480 nM, at 490 nM, or at 500 nM In some embodiments of any of the aspects, the ligase is present at about 10-1000 nM. In some embodiments of any of the aspects, the ligase is present at about 100 nM. In some embodiments of any of the aspects, the ligase is present at about 10 nM, at about 20 nM, at about 30 nM, at about 40 nM, at about 50 nM, at about 60 nM, at about 70 nM, at about 80 nM, at about 90 nM, at about 100 nM, at about 110 nM, at about 120 nM, at about 130 nM, at about 140 nM, at about 150 nM, at about 160 nM, at about 170 nM, at about 180 nM, at about 190 nM, at about 200 nM, at about 210 nM, at about 220 nM, at about 230 nM, at about 240 nM, at about 250 nM, at about 260 nM, at about 270 nM, at about 280 nM, at about 290 nM, at about 300 nM, at about 310 nM, at about 320 nM, at about 330 nM, at about 340 nM, at about 350 nM, at about 360 nM, at about 370 nM, at about 380 nM, at about 390 nM, at about 400 nM, at about 410 nM, at about 420 nM, at about 430 nM, at about 440 nM, at about 450 nM, at about 460 nM, at about 470 nM, at about 480 nM, at about 490 nM, at about 500 nM, at about 510 nM, at about 520 nM, at about 530 nM, at about 540 nM, at about 550 nM, at about 560 nM, at about 570 nM, at about 580 nM, at about 590 nM, at about 600 nM, at about 610 nM, at about 620 nM, at about 630 nM, at about 640 nM, at about 650 nM, at about 660 nM, at about 670 nM, at about 680 nM, at about 690 nM, at about 700 nM, at about 710 nM, at about 720 nM, at about 730 nM, at about 740 nM, at about 750 nM, at about 760 nM, at about 770 nM, at about 780 nM, at about 790 nM, at about 800 nM, at about 810 nM, at about 820 nM, at about 830 nM, at about 840 nM, at about 850 nM, at about 860 nM, at about 870 nM, at about 880 nM, at about 890 nM, at about 900 nM, at about 910 nM, at about 920 nM, at about 930 nM, at about 940 nM, at about 950 nM, at about 960 nM, at about 970 nM, at about 980 nM, at about 990 nM, or at about 1000 nM.

In some embodiments of any of the aspects, the ligase is present at 10-1000 nM. In some embodiments of any of the aspects, the ligase is present at 100 nM. In some embodiments of any of the aspects, the ligase is present at 10 nM, at 20 nM, at 30 nM, at 40 nM, at 50 nM, at 60 nM, at 70 nM, at 80 nM, at 90 nM, at 100 nM, at 110 nM, at 120 nM, at 130 nM, at 140 nM, at 150 nM, at 160 nM, at 170 nM, at 180 nM, at 190 nM, at 200 nM, at 210 nM, at 220 nM, at 230 nM, at 240 nM, at 250 nM, at 260 nM, at 270 nM, at 280 nM, at 290 nM, at 300 nM, at 310 nM, at 320 nM, at 330 nM, at 340 nM, at 350 nM, at 360 nM, at 370 nM, at 380 nM, at 390 nM, at 400 nM, at 410 nM, at 420 nM, at 430 nM, at 440 nM, at 450 nM, at 460 nM, at 470 nM, at 480 nM, at 490 nM, at 500 nM, at 510 nM, at 520 nM, at 530 nM, at 540 nM, at 550 nM, at 560 nM, at 570 nM, at 580 nM, at 590 nM, at 600 nM, at 610 nM, at 620 nM, at 630 nM, at 640 nM, at 650 nM, at 660 nM, at 670 nM, at 680 nM, at 690 nM, at 700 nM, at 710 nM, at 720 nM, at 730 nM, at 740 nM, at 750 nM, at 760 nM, at 770 nM, at 780 nM, at 790 nM, at 800 nM, at 810 nM, at 820 nM, at 830 nM, at 840 nM, at 850 nM, at 860 nM, at 870 nM, at 880 nM, at 890 nM, at 900 nM, at 910 nM, at 920 nM, at 930 nM, at 940 nM, at 950 nM, at 960 nM, at 970 nM, at 980 nM, at 990 nM, or at 1000 nM.

In some embodiments of any of the aspects, step b) comprising contacting the nucleic acid sensor system with the sample in the presence of ligase can comprise incubating or maintain for a period of from 1 minute to 60 minutes. In some embodiments of any of the aspects, the ligation reaction of step b) is incubated or maintained for about 1 minute, for about 2 minutes, for about 3 minutes, for about 4 minutes, for about 5 minutes, for about 6 minutes, for about 7 minutes, for about 8 minutes, for about 9 minutes, for about 10 minutes, for about 11 minutes, for about 12 minutes, for about 13 minutes, for about 14 minutes, for about 15 minutes, for about 16 minutes, for about 17 minutes, for about 18 minutes, for about 19 minutes, for about 20 minutes, for about 21 minutes, for about 22 minutes, for about 23 minutes, for about 24 minutes, for about 25 minutes, for about 26 minutes, for about 27 minutes, for about 28 minutes, for about 29 minutes, for about 30 minutes, for about 31 minutes, for about 32 minutes, for about 33 minutes, for about 34 minutes, for about 35 minutes, for about 36 minutes, for about 37 minutes, for about 38 minutes, for about 39 minutes, for about 40 minutes, for about 41 minutes, for about 42 minutes, for about 43 minutes, for about 44 minutes, for about 45 minutes, for about 46 minutes, for about 47 minutes, for about 48 minutes, for about 49 minutes, for about 50 minutes, for about 51 minutes, for about 52 minutes, for about 53 minutes, for about 54 minutes, for about 55 minutes, for about 56 minutes, for about 57 minutes, for about 58 minutes, for about 59 minutes, or for about 60 minutes. Optionally the reaction of step b) can be incubated at about ambient temperature (e.g., 24-26° C.).

In some embodiments of any of the aspects, step b) comprising contacting the nucleic acid sensor system with the sample in the presence of ligase can comprise incubating or maintain for a period of from 1 minute to 60 minutes. In some embodiments of any of the aspects, the ligation reaction of step b) is incubated or maintained for 1 minute, for 2 minutes, for 3 minutes, for 4 minutes, for 5 minutes, for 6 minutes, for 7 minutes, for 8 minutes, for 9 minutes, for 10 minutes, for 11 minutes, for 12 minutes, for 13 minutes, for 14 minutes, for 15 minutes, for 16 minutes, for 17 minutes, for 18 minutes, for 19 minutes, for 20 minutes, for 21 minutes, for 22 minutes, for 23 minutes, for 24 minutes, for 25 minutes, for 26 minutes, for 27 minutes, for 28 minutes, for 29 minutes, for 30 minutes, for 31 minutes, for 32 minutes, for 33 minutes, for 34 minutes, for 35 minutes, for 36 minutes, for 37 minutes, for 38 minutes, for 39 minutes, for 40 minutes, for 41 minutes, for 42 minutes, for 43 minutes, for 44 minutes, for 45 minutes, for 46 minutes, for 47 minutes, for 48 minutes, for 49 minutes, for 50 minutes, for 51 minutes, for 52 minutes, for 53 minutes, for 54 minutes, for 55 minutes, for 56 minutes, for 57 minutes, for 58 minutes, for 59 minutes, or for 60 minutes. Optionally the reaction of step b) can be incubated at ambient temperature (e.g., 24-26° C.).

In some embodiments of any of the aspects, step c) comprising contacting the reaction product produced in step b) to a cell free expression system can comprise incubation or maintaining for a period of time from 15 minutes to 12 hours. In some embodiments of any of the aspects, the reaction of step c) is incubated for about 15 minutes, for about 30 minutes, for about 45 minutes, for about 60 minutes. In some embodiments the reaction of step c) is incubated for about 1.0 hour, for about 1.5 hours, for about 2.0 hours, for about 2.5 hours, for about 3.0 hours, for about 3.5 hours, for about 4.0 hours, for about 4.5 hours, for about 5.0 hours, for about 5.5 hours, for about 6.0 hours, for about 6.5 hours, for about 7.0 hours, for about 7.5 hours, for about 8.0 hours, for about 8.5 hours, for about 9.0 hours, for about 9.5 hours, for about 10.0 hours, for about 10.5 hours, for about 11.0 hours, for about 11.5 hours, or for about 12.0 hours. Optionally the reaction of step c) can be incubated at about ambient temperature (e.g., 24-26° C.). For example, step b) can be incubated for a period of from 5 minutes to 15 minutes at ambient temperature (e.g., 24-26° C.) and/or step c) can be incubated for a period of time from 60 minutes to 3 hours, at ambient temperature (e.g., 24-26° C.).

In some embodiments of any of the aspects, step c) comprising contacting the reaction product produced in step b) to a cell free expression system can comprise incubation or maintaining for a period of time from 15 minutes to 12 hours. In some embodiments of any of the aspects, the reaction of step c) is incubated for 15 minutes, for 30 minutes, for 45 minutes, for 60 minutes. In some embodiments the reaction of step c) is incubated for 1.0 hour, for 1.5 hours, for 2.0 hours, for 2.5 hours, for 3.0 hours, for 3.5 hours, for 4.0 hours, for 4.5 hours, for 5.0 hours, for 5.5 hours, for 6.0 hours, for 6.5 hours, for 7.0 hours, for 7.5 hours, for 8.0 hours, for 8.5 hours, for 9.0 hours, for 9.5 hours, for 10.0 hours, for 10.5 hours, for 11.0 hours, for 11.5 hours, or for 12.0 hours. Optionally the reaction of step c) can be incubated at ambient temperature (e.g., 24-26° C.). For example, step b) can be incubated for a period of from 5 minutes to 15 minutes at ambient temperature (e.g., 24-26° C.) and/or step c) can be incubated for a period of time from 60 minutes to 3 hours, at ambient temperature (e.g., 24-26° C.).

Those skilled in the art will appreciate that, in some embodiments, particular steps may be performed in series; in some embodiments particular steps may be performed in parallel or simultaneously (e.g., in a "one-pot" reaction). For example, in some embodiments, steps b) and c) may be performed serially; in some embodiments, these steps may be performed in parallel or simultaneously (e.g., in such "one-pot" reaction). In some embodiments of any of the aspects, the cell free expression system further comprises an RNAse inhibitor. The RNase inhibitor can inhibit at least one of RNase A, RNase H, RNase III, RNase L, RNase P, RNase PhyM, RNase T1, Rnase T2, Rnase U2, or Rnase V. In some embodiments of any of the aspects, the cell free expression system further comprises 0.5 nM to 5 µM ssDNA primer complementary to the 3' end of the second nucleic acid or domain. In some embodiments of any of the aspects, the cell free expression system further comprises about 1.25 µM ssDNA primer complementary to the 3' end of the second nucleic acid or domain. In some embodiments of any of the aspects, the cell free expression system comprises about 0.5 nM, about 1 nM, about 5 nM, about 10 nM, about 20 nM, about 30 nM, about 40 nM, about 50 nM, about 60 nM, about 70 nM, about 80 nM, about 90 nM, about 100 nM, about 110 nM, about 125 nM, about 250 nM, about 375 nM, about 500 nM, about 625 nM, about 750 nM, about 875 nM, about 1.000 µM, about 1.125 M, about 1.250 µM, about 1.375 µM, about 1.500 µM, about 1.625 µM, about 1.750

µM, about 1.875 µM, about 2.000 µM, about 2.125 µM, about 2.250 µM, about 2.375 µM, about 2.500 µM, about 2.625 µM, about 2.750 µM, about 2.875 µM, about 3.000 µM, about 3.125 µM, about 3.250 M, about 3.375 µM, about 3.500 µM, about 3.625 µM, about 3.750 µM, about 3.875 µM, about 4.000 µM, about 4.125 M, about 4.250 µM, about 4.375 µM, about 4.500 µM, about 4.625 µM, about 4.750 µM, about 4.875 µM, or about 5.000 µM of the ssDNA primer complementary to the 3' end of the second nucleic acid or domain.

Those skilled in the art will appreciate that various configurations of cell free expression systems can be useful. For example, in some embodiments, a cell free expression system may include about 1.25 µM ssDNA primer complementary to a sequence within the non-template expression cassette or intervening ssDNA sequences. In some embodiments of any of the aspects, the cell free expression system comprises about 0.5 nM, about 1 nM, about 5 nM, about 10 nM, about 20 nM, about 30 nM, about 40 nM, about 50 nM, about 60 nM, about 70 nM, about 80 nM, about 90 nM, about 100 nM, about 110 nM, about 125 nM, about 250 nM, about 375 nM, about 500 nM, about 625 nM, about 750 nM, about 875 nM, about 1.000 µM, about 1.125 µM, about 1.250 µM, about 1.375 µM, about 1.500 µM, about 1.625 µM, about 1.750 µM, about 1.875 UM, about 2.000 µM, about 2.125 µM, about 2.250 µM, about 2.375 µM, about 2.500 µM, about 2.625 µM, about 2.750 µM, about 2.875 µM, about 3.000 µM, about 3.125 µM, about 3.250 M, about 3.375 µM, about 3.500 µM, about 3.625 µM, about 3.750 µM, about 3.875 µM, about 4.000 µM, about 4.125 µM, about 4.250 µM, about 4.375 µM, about 4.500 µM, about 4.625 µM, about 4.750 µM, about 4.875 µM, or about 5.000 UM of the ssDNA primer complementary to a sequence within the non-template expression cassette or intervening ssDNA sequences (e.g. FIG. 2B (i)).

In some embodiments of any of the aspects, the concentration of dNTPs is at about 200-500 M. In some embodiments of any of the aspects, the concentration of dNTPS is at about 230. In some embodiments of any of the aspects, the concentration of dNTPs is at about 200 µM, at about 210 µM, at about 220 µM, at about 230 µM, at about 240 µM, at about 250 µM, at about 260 µM, at about 270 µM, at about 280 µM, at about 290 µM, at about 300 µM, at about 310 µM, at about 320 µM, at about 330 µM, at about 340 µM, at about 350 µM, at about 360 µM, at about 370 µM, at about 380 µM, at about 390 µM, at about 400 µM, at about 410 µM, at about 420 µM, at about 430 µM, at about 440 µM, at about 450 µM, at about 460 µM, at about 470 µM, at about 480 µM, at about 490 µM, or at about 500 µM.

In some embodiments of any of the aspects, the concentration of dNTPs is at 200-500 µM. In some embodiments of any of the aspects, the concentration of dNTPS is at 230 M. In some embodiments of any of the aspects, the concentration of dNTPs is at 200 µM, at 210 µM, at 220 µM, at 230 µM, at 240 µM, at 250 µM, at 260 µM, at 270 µM, at 280 µM, at 290 µM, at 300µ, at 310µ, at 320µ, at 330µ, at 340µ, at 350µ, at 360µ, at 370µ, at 380 µM, at 390 µM, at 400 µM, at 410 µM, at 420 µM, at 430 µM, at 440 µM, at 450 µM, at 460 µM, at 470 µM, at 480 µM, at 490 µM, or at 500 µM.

In some embodiments of any of the aspects, the DNA polymerase is selected from the group consisting of a Klenow fragment with exonuclease portion, a Klenow fragment without the exonuclease portion, a phi29 polymerase, a modified T7 DNA polymerase, a polymerase from *Psychrobacillus*, a polymerase from *Psychrobacillus* with enhanced strand displacement, and a polymerase from *B. subtilis*. In various embodiments, the various aforementioned components are in a combined mixture suitable for performing the aforementioned method. In some embodiments of any of the aspects, the reporter protein is luciferase and the reporter protein substrate is a luciferase substrate and measuring is by detection of luminescence in the cell free expression system.

In some embodiments of any of the aspects, the method further includes hybridization of the ssDNA primer to the RNA transcript, reverse transcription using a reverse transcriptase, and endolytic cleavage. For example, amplification of the expression cassette formed by target nucleic-acid mediated ligation and primer extension can further improve detection system sensitivity. Transcription of the dsDNA product to RNA can be followed by hybridization of the DNA primer, for example the same primer that anneals to the 3' end of the expression cassette or a different DNA primer, to the complementary 3' end of the RNA transcript. A reverse transcriptase can extend the DNA primer to create an RNA/DNA hybrid molecule. RNaseH endonuclease activity can hydrolytically cleave the RNA of the DNA/RNA hybrid to create a ssDNA molecule complementary to the upstream, or A sensor part or A domain, or another DNA primer (see e.g., FIG. 2A). As used herein, "A sensor part" is used interchangeably with first sensor part, first nucleic acid, A domain, first sequence or first domain, and refers to the portion of the nucleic acid hybridization sequence comprising a 3' hybridization region. As used herein, "B sensor part" is used interchangeably with second sensor part, second nucleic acid, B domain, B sequence or second domain, and refers to the portion of the nucleic acid hybridization sequence comprising a 5' hybridization region. Hybridization of the A sensor part to the ssDNA molecule enables extension via the DNA polymerase to create a full expression cassette. Transcription of the expression cassette to RNA enables subsequent rounds of expression cassette amplification. In some embodiments of any of the aspects, the systems may include an enzyme containing reverse transcriptase activity and a non-specific endonuclease that catalyzes the hydrolytic cleavage of RNA in an RNA/DNA hybrid molecule. In some embodiments of any of the aspects, the reverse transcriptase may be HIV-1, RTx, Luna® (New England Biolabs®), recombinant Moloney Murine Leukemia Virus Reverse Transcriptases with reduced or fully removed RNAse H activity (RNase H−). In some embodiments of any of the aspects, the endonuclease may be RNaseH. In some embodiments of any of the aspects, the activities may be catalyzed by a single enzyme, such as Avian Myeloblastosis Virus (AMV) Reverse Transcriptase, Moloney Murine Leukemia Virus Reverse Transcriptase, or variants thereof.

As used herein, "DNA expression cassette" refers to a single-stranded DNA (ssDNA) comprising the first and second nucleic acids or A and B domains, which, when ligated together encodes a polypeptide.

As used herein, a "target" or "target nucleic acid" or "target sequence" or "target nucleic acid sequence" refers to an RNA or ssDNA that can hybridize with both the 3' hybridization region of the first nucleic acid or A domain, and the 5' hybridization region of the second nucleic acid or B domain.

Also described herein is a method for detecting a target nucleic acid in a sample, including: a) providing the aforementioned nucleic acid sensor systems, in which the upstream and downstream hybridization regions are complementary to a portion of the target nucleic acid such that hybridization of the target nucleic acid to the upstream and downstream hybridization regions creates a junction between the first and second domains sufficient for productive ligation to occur; b) contacting the nucleic acid sensor system with the sample in the presence of ligase under conditions appropriate for hybridization of the target nucleic acid with the upstream and downstream hybridization regions and ligation of the upstream and downstream hybridization region, to thereby produce an operably-linked ssDNA reaction product; c) contacting the reaction product produced in step b) to a cell free expression system including a strand-displacing DNA polymerase, dNTPs and other building block components necessary for protein production, and a ssDNA primer under conditions appropriate for DNA polymerization, transcription and translation to thereby produce a reporter protein; d) observing activity of reporter protein product of step c) to indicate the presence of the target nucleic acid in the sample.

In some embodiments of any of the aspects, the sensor system described herein, and methods of using thereof, may be used for the detection of a target nucleic acid which differs from another nucleic acid in the sample by a single base, enabling discrimination of single nucleotide polymorphisms (SNPs). In some embodiments of any of the aspects, the location of the SNP within the hybridization region is positioned at one of the two bases of the linking junction, on either the upstream or downstream ssDNA domain. In some embodiments of any of the aspects, one or more mismatched bases may be additionally introduced within the hybridization region. Destabilization of the hybridization regions due to the presence of the SNP would impede the ability for the ligase to successfully link the upstream and downstream domains, resulting in a differential signal output. In various embodiments, the junction is configured to hybridize against a polymorphism of the target nucleic acid. As an example, four different exemplary variants (polymorphisms) were tested (see e.g., Example 15).

In a various embodiments, the ssDNA A domain would include, in the 5' to 3' direction, (i) a promoter, (ii) a ribosome binding site (RBS), (iii) the start codon of a reporter protein coding sequence, and (iv) a hybridization region complementary to a region of the target nucleic acid. The ssDNA B domain would include, in the 5' to 3' direction, (i) a hybridization region complementary to a region of the target nucleic acid, and (ii) the remaining coding sequence of a reporter protein. A third nucleic acid component would be a ssDNA 'primer' that hybridizes to the 3' end of the B domain (see e.g., FIG. 2A). Alternative sensor component schemes include: (i) A and B domains, wherein the 5' end of the A domain is linked to the 3' end of the B domain with intervening ssDNA sequences, (ii) incorporating the ssDNA primer as a terminal hairpin of B domain, or (iii) including hairpins on both the 5' end of the A domain and the 3' end of the B domain (see e.g., FIG. 2B). These alternative schemes may offer advantages by reducing the number of components and/or reducing the number of exposed ssDNA ends susceptible to DNA exonucleases.

The sensor system molecules are incubated with a sample containing a target nucleic acid and a cell-free expression system containing necessary components and building block materials for transcription and translation. The claimed sensors can be used for in vitro detection of any RNA or ssDNA (e.g., ssDNA viruses, or ssDNA generated by denaturation of genomic dsDNA), single nucleotide variants, or SNPs. This enables detection of a variety of microorganism and nucleic acids indicative of infection or other factors associated with human health, animal health, and plant health.

RNA targets include messenger RNA, microRNA, viral genomic RNA, and ribosomal RNA. A particularly useful target for bacterial detection is ribosomal RNA (e.g., 16S or 23S rRNA) as it can be present at many copies per individual bacterial cell and can be used to distinguish bacterial genus/species. Infectious bacterial target organisms include, but are limited to species of *Streptococcus, Staphylococcus, Bacillus, Campylobacter, Chlamydia, Clostridium, Enterococcus, Escherichia, Helicobacter, Listeria, Mycobacterium, Salmonella, Vibrio, Yersinia.* A description of a variety of 16S ribosomal RNA target regions for the diagnosis of pathogenic bacteria is further described in, e.g., J. Microbiol Methods 2007 May 69 (2): 330-339, which is incorporated herein by reference in its entirety. RNA viruses can be detected, for example, by designing sensors for regions of viral RNA genomes. Exemplary RNA viruses include but are not limited to human immunodeficiency virus (HIV), influenza virus, zika virus, ebola virus, rotavirus, polio virus, dengue virus, yellow fever virus, hepatitis C virus, measles virus, and rabies virus.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ *ed., Revised*, J. Wiley & Sons (New York, NY 2006), and Sambrook and Russel, *Molecular Cloning: A Laboratory Manual* 4$^{th}$ *ed.*, Cold Spring Harbor Laboratory Press (Cold Spring Harbor, NY 2012), provide one skilled in the art with a general guide to many of the terms used in the present application.

As used herein, the term "nucleic acid" or "nucleic acid sequence" refers to any molecule, preferably a polymeric molecule, including units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the target nucleic acid is DNA. In another aspect, the target is RNA. Suitable nucleic acid molecules are DNA, including genomic DNA or cDNA. Other suitable nucleic acid molecules are RNA, including mRNA and ribosomal RNA.

As used herein, the term "DNA" is defined as deoxyribonucleic acid. The term "polynucleotide" is used herein interchangeably with "nucleic acid" to indicate a polymer of nucleosides. Typically, a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However, the term encompasses molecules comprising nucleosides or nucleoside analogs containing chemically or biologically modified bases, modified backbones, etc., whether or not found in naturally occurring nucleic acids, and such molecules may be preferred for certain applications. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

As used herein, the term "single-stranded DNA (ssDNA)" refers to DNA that consists only of one chain of nucleotides, as opposed to two strands of DNA that form the DNA helix.

Where this application refers to a polynucleotide it is understood that both DNA, RNA, and in each case both single- and double-stranded forms (and complements of each single-stranded molecule) are provided.

As used herein, "promoter" refers to a polynucleotide molecule that in its native state (i.e., as is naturally in the genome of an organism) is located upstream of or 5' to a translational start codon of an open reading frame (or protein-coding region). In some embodiments, the term "promoter" may be used herein to refer to a modified polynucleotide molecule, specifically designed to have desired properties (e.g., improved transcriptional efficiency). A promoter can comprise sequence both 5' and/or 3' of the transcription start site. A promoter is involved in the recognition and binding of RNA polymerase II, or other RNA polymerases such as T7 RNA polymerase, and other proteins (trans-acting transcription factors) to initiate transcription. A promoter typically can be from about 20 bp to about 1000 bp in length, e.g. about 20 bp in length, about 30 bp in length, about 40 bp in length, about 50 bp in length, about 60 bp in length, about 70 bp in length, about 80 bp in length, about 90 bp in length, about 100 bp in length, about 150 bp in length, about 200 bp in length, about 250 bp in length, about 300 bp in length, about 350 bp in length, about 400 bp in length, about 450 bp in length, about 500 bp in length, about 550 bp in length, about 600 bp in length, about 650 bp in length, about 700 bp in length, about 750 bp in length, about 800 bp in length, about 850 bp in length, about 900 bp in length, about 950 bp in length, or about 1000 bp in length. The sequence and/or location of a given promoter can be predicted using computer programs known in the art, e.g. ElDorado; Gene2Promoter; GEMS Launcher; PromoterInspector; Promoter2.0; McPromoter; EP3; ProSOM; and TRED.

As used herein, the term "complementary" refers to the hierarchy of hydrogen-bonded base pair formation preferences between the nucleotide bases G, A, T, C and U, such that when two given polynucleotides or polynucleotide sequences anneal to each other, A pairs with T and G pairs with C in DNA, and G pairs with C and A pairs with U in RNA. As used herein, "substantially complementary" refers to a nucleic acid molecule or portion thereof (e.g. a primer) having at least 90% complementarity over the entire length of the molecule or portion thereof with a second nucleotide sequence, e.g. 90% complementary, 95% complementary, 98% complementary, 99% complementary, or 100% complementary. As used herein, "substantially identical" refers to a nucleic acid molecule or portion thereof having at least 90% identity over the entire length of a molecule or portion thereof with a second nucleotide sequence, e.g. 90% identity, 95% identity, 98% identity, 99% identity, or 100% identity.

As used herein, "hybridize" refers to two nucleic acid strands engaging in physical base pairing, preferably to the extent that the strands remain base paired to such a degree that a template-dependent polymerase can conduct polymerization on the duplex. One having ordinary skill in the art, using the sequence information of the target nucleic acid sequences, can design hybridization regions or sequences for the sensors described herein which are complementary (e.g., fully complementary) to a single target and not to other nucleic acid sequences that may be present in the sample. Hybridization conditions can be routinely optimized to minimize background signal.

As used herein, the term "operably linked" refers to a first polynucleotide molecule, such as a promoter or start codon, connected with a second transcribable polynucleotide molecule, such as a gene coding for a reporter protein, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter regulates or mediates transcription of the gene of interest in a cell.

As used herein, the term "ribosome binding site (RBS)" refers to a nucleotide sequence positioned upstream (e.g., towards the 5' end) of the start codon for mRNA transcript that functions to recruit ribosome during initiation of protein translation. Ribosome recruitment in eukaryotes is generally mediated by the 5' cap present on eukaryotic mRNAs.

As used herein, the term "terminal hairpin loop" refers to a structure that forms when two regions of the same strand, usually complementary in nucleotide sequence when read in opposite directions, base-pair to form a double helix that ends in an unpaired loop.

As used herein, a "portion" of a nucleic acid molecule refers to contiguous set of nucleotides comprised by that molecule. A portion can comprise all or only a subset of the nucleotides comprised by the molecule. A portion can be double-stranded or single-stranded.

As used herein, the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), *The Encyclopedia of Molecular Biology*, published by Blackwell Science Ltd., 1994 (ISBN 0-632-02182-9). Definitions of common terms in molecular biology can also be found in Benjamin Lewin, *Genes X*, published by Jones & Bartlett Publishing, 2009 (ISBN-10: 0763766321); Kendrew et al. (eds.), *Molecular Biology and Biotechnology: a Comprehensive Desk Reference*, published by VCH Publishers, Inc., 1995 (ISBN 1-56081-569-8) and Current *Protocols in Protein Sciences* 2009, Wiley Intersciences, Coligan et al., eds.

In some embodiments of any of the aspects, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a biomolecule directly, and/or detecting particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the components of the nucleic acid sensor system described herein are exogenous. In some embodiments of any of the aspects, the components of the nucleic acid sensor system described herein are ectopic. In some embodiments of any of the aspects, the components of the nucleic acid sensor system described herein are not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell, a cell-free system, or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell, a cell-free system, or organism in which it is found in relatively low amounts and one wishes to increase the amount of the nucleic acid or polypeptide in the cell, a cell-free system, or organism, e.g., to create ectopic expression or levels. In contrast, the term "endogenous" refers to a substance that is native to the biological system, a cell-free system, or cell. As used herein, "ectopic" refers to a substance that is found in an unusual location and/or amount. An ectopic substance can be one that is normally found in a given cell or cell-free system, but at a much lower amount and/or at a different time. Ectopic also includes substance, such as a polypeptide or nucleic acid that is not naturally found or expressed in a given cell in its natural environment.

In some embodiments of any of the aspects, a nucleic acid encoding a polypeptide as described herein (e.g. a polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

It should be understood that the vectors described herein can, in some embodiments of any of the aspects, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration.

As used herein, "contacting" refers to any suitable means for delivering, or exposing, an agent to another agent, a reagent, a sequence, a cell, or a cell-free expression system. Exemplary delivery methods include, but are not limited to, direct delivery to cell culture medium, perfusion, injection, or other delivery method well known to one skilled in the art. In some embodiments of any of the aspects, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Unless otherwise stated, the present invention was performed using standard procedures, as described, for example in Sambrook and Russel, *Molecular Cloning: A Laboratory Manual 4th ed.*, Cold Spring Harbor Laboratory Press (Cold Spring Harbor, NY 2012) and Davis et al., *Basic Methods in Molecular Biology*, Elsevier Science Publishing, Inc., New York, USA (1995) which are all incorporated by reference herein in their entireties.

Other terms are defined herein within the description of the various aspects of the invention.

One skilled in the art will recognize many methods and materials similar or equivalent to those described herein, which could be used in the practice of the present invention. Indeed, the present invention is in no way limited to the methods and materials described.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The various methods and techniques described herein provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are nucleic acid sensor system components, including single stranded nucleic acid domains, ribosome binding sites, codons, operatively linked and/or functionally organized, further including techniques and composition and use of solutions used therein, and the particular use of the products created through the teachings of the invention. Various embodiments of the invention can specifically include or exclude any of these variations or elements.

In some embodiments of any of the aspects, the numbers expressing quantities of ingredients, properties such as concentration, reaction conditions, and so forth, used to describe and claim certain embodiments of the invention are to be understood as being modified in some instances by the term "about." Accordingly, in some embodiments of any of the aspects, the numerical parameters set forth in the written description and attached claims are approximations that can vary depending upon the desired properties sought to be obtained by a particular embodiment. In some embodiments of any of the aspects, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments of any of the aspects, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the herein-described elements in all possible variations thereof is encompassed by the invention unless otherwise indicated herein or otherwise clearly contradicted by context.

Furthermore, numerous references have been made to patents and printed publications throughout this specification. Each of the cited references and printed publications are herein individually incorporated by reference in their entirety.

It is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The technology described herein is further illustrated by the following examples which in no way should be construed as being further limiting.

Some embodiments of the technology described herein can be defined according to any of the following numbered paragraphs:

1. A nucleic acid sensor system, comprising:
   a) a first nucleic acid comprising a 3' hybridization region and a second nucleic acid comprising 5' hybridization region,
   b) wherein the first nucleic acid and the second nucleic acid, when bridged by a target nucleic acid that hybridizes to the 3' hybridization region and the 5' hybridization region, are configured to encode a non-template cassette comprising a promoter, a ribosome binding site, and a coding sequence for a reporter protein.

2. The nucleic acid sensor system of paragraph 1, wherein the system comprises a primer complementary to a 3' region of the second nucleic acid.

3. The nucleic acid sensor system of paragraph 1, wherein the first nucleic acid and the second nucleic acid are DNA.

4. The nucleic acid sensor system of paragraph 1, wherein at least a portion of the 3' hybridization region is in the promoter, the ribosome binding site, or the coding sequence.

5. The nucleic acid sensor system of paragraph 1, wherein at least a portion of the 5' hybridization region is in the promoter, the ribosome binding site, or the coding sequence.

6. The nucleic acid system of any one of paragraphs 1-5 comprising a cell free expression system.

7. The nucleic acid system of any one of paragraphs 1-6, comprising a ligase

8. The nucleic acid system of any one of paragraphs 1-7, comprising a reverse transcriptase.

9. The nucleic acid system of any one of paragraphs 1-8, comprising a ribonuclease that hydrolyzes RNA which is hybridized to DNA.

10. The nucleic acid system of any one of paragraphs 9, wherein the ribonuclease is RNAse H.

11. A nucleic acid sensor system, comprising:
   a) a non-functional, single-stranded, non-template form of a DNA expression cassette comprising:
      i) a promoter;
      ii) a RBS;
      iii) a coding sequence for a reporter protein;
      wherein a target nucleic acid hybridization sequence is inserted within the cassette, and the cassette is separated into two molecules wherein the separation occurs within the hybridization region;
   b) a single-stranded DNA primer complementary to a 3' region of the expression cassette;
   c) a ligase; and
   d) a cell-free expression system.

12. A nucleic acid sensor system, comprising:
  a) a first single stranded DNA (ssDNA) domain comprising from 5' to 3', a non-template strand of:
    i) a promoter;
    ii) a ribosome binding site (RBS);
    iii) a start codon; and
    iv) an upstream portion of a hybridization region in the form of a reading frame in-frame with the start codon;
  b) a second ssDNA domain comprising from 5' to 3', a non-template strand of:
    i) a downstream portion of the hybridization region in the form of a reading frame in frame with the start codon; and
    ii) a coding sequence for a reporter protein linked downstream of and in-frame with the downstream portion of the hybridization region; and
  c) a ssDNA primer complementary to a 3' region of the second domain.

13. A nucleic acid sensor system, comprising:
  a) a first single stranded DNA (ssDNA) domain comprising from 5' to 3', a non-template strand of:
    i) a promoter; and
    ii) an upstream portion of a hybridization region;
  b) a second ssDNA domain comprising from 5' to 3', a non-template strand of:
    i) a downstream portion of the hybridization region;
    ii) a ribosome binding site (RBS); and
    iii) a start codon linked in-frame with a coding sequence for a reporter protein; and
  c) a ssDNA primer complementary to a 3' region of the second domain.

14. A nucleic acid sensor system, comprising:
  a) a first single stranded DNA (ssDNA) domain comprising from 5' to 3', a non-template strand of:
    i) a promoter;
    ii) a ribosome binding site (RBS);
    iii) a start codon linked in-frame with an upstream portion of a coding sequence for a reporter protein; and
    iv) an upstream portion of a hybridization region in the form of a reading frame linked downstream of and in-frame with the upstream portion of a coding sequence for a reporter protein;
  b) a second ssDNA domain comprising from 5' to 3', a non-template strand of:
    i) a downstream portion of the hybridization region in the form of a reading frame in frame with the start codon; and
    ii) the remaining portion of a coding sequence for the reporter protein linked downstream of and in-frame with the downstream portion of the hybridization region; and
  c) a ssDNA primer complementary to the second domain at its 3' end.

15. The nucleic acid sensor system of any of paragraphs 11-14, wherein the first and second ssDNA domains are separate DNA fragments and the second ssDNA domain comprises a 5' phosphate.

16. The nucleic acid sensor system of paragraph 15, wherein the second ssDNA domain further comprises a nucleotide sequence at its 3' end comprising the ssDNA primer in a terminal hairpin loop.

17. The nucleic acid sensor system of paragraph 16, wherein the 5' end of the first domain further comprises a sequence that forms a terminal hairpin loop.

18. The nucleic acid sensor system of any of paragraphs 12-15, wherein the 5' end of the first domain is linked to the 3' end of the second domain through intervening ssDNA sequences so that the first and second domains are present on a single ssDNA sequence.

19. The nucleic acid sensor system of any of paragraphs 1-18, wherein the hybridization region is at least 12 nucleotides.

20. The nucleic acid sensor system of paragraph 19, wherein the upstream and downstream portion of the hybridization region are each at least 6 nucleotides.

21. The nucleic acid sensor system of any of paragraphs 11-20, wherein the reporter protein is selected from the group consisting of luciferase, beta-lactamase, beta-galactosidase, horseradish peroxidase, alkaline phosphatase, catalase, carbonic anhydrase, green fluorescent protein, red fluorescent protein, cyan fluorescent protein, yellow fluorescent protein, trypsin, a protease, a peptide that complements and activates a truncated reporter protein.

22. The nucleic acid sensor system of any of paragraphs 12-21, further comprising one or more of ligase, a strand-displacing DNA polymerase, dNTPs, RNAse inhibitor, and a cell free expression system.

23. The nucleic acid sensor system of paragraph 22, wherein the cell free expression system is whole cell extract.

24. The nucleic acid sensor system of paragraph 22 or 23, wherein the strand displacing DNA polymerase is selected from the group consisting of Klenow fragment with exonuclease portion, Klenow fragment without the exonuclease portion, phi29 polymerase, and a modified T7 DNA polymerase.

25. A kit, comprising:
  a nucleic acid sensor system of any of paragraphs 1-24; and
  a positive control.

26. A method for detecting a target nucleic acid in a sample, comprising:
  a) providing a nucleic acid sensor system of any of paragraphs 1-24, in which the upstream and downstream hybridization regions are complementary to a portion of the target nucleic acid such that hybridization of the target nucleic acid to the upstream and downstream hybridization regions creates a junction between the first and second domains;
  b) contacting the nucleic acid sensor system with the sample in the presence of ligase under conditions appropriate for hybridization of the target nucleic acid with the upstream and downstream hybridization regions and ligation of the upstream and downstream hybridization region, to thereby produce an operably-linked ssDNA reaction product;
  c) contacting the reaction product produced in step b) to a cell free expression system comprising a strand displacing DNA polymerase, dNTPs and other building block components necessary for protein production, and a ssDNA primer under conditions appropriate for DNA polymerization, transcription and translation to thereby produce a reporter protein;
  d) measuring reporter protein present to indicates the presence of the target nucleic acid in the sample.

27. The method of paragraph 26, wherein components of the nucleic acid sensor system are each present at about 16 nM.

28. The method of paragraph 26, wherein ligase is present at about 100 nM.

29. The method of paragraph 26, wherein step b) is incubated for a period of from 5 minutes to 15 minutes at ambient temperature (24-26 C) and/or step c) is incubated for a period of time from 60 minutes to 3 hours, at ambient temperature.

30. The method of paragraph 26, wherein the cell free expression system further comprises RNAse inhibitor.

31. The method of paragraph 26, wherein the cell free expression system further comprises 12.5 μM ssDNA primer complementary to the 3' end of the second domain.

32. The method of paragraph 26, wherein the concentration of dNTPs is about 230 μM.

33. The method of paragraph 26, wherein the DNA polymerase is selected from the group consisting of Klenow fragment with exonuclease portion, Klenow fragment without the exonuclease portion, phi29 polymerase, and a modified T7 DNA polymerase.

34. The method of paragraph 26, wherein the reporter protein is luciferase and measuring is by detection of luminescence in the cell free expression system.

35. The method of paragraph 26, wherein transcription further comprises hybridization of the ssDNA primer is hybridized to the RNA transcript, reverse transcription using a reverse transcriptase, and endolytic cleavage.

36. The method of paragraph 26, wherein the junction is configured to hybridize against a polymorphism of the target nucleic acid.

Some embodiments of the technology described herein can be defined according to any of the following numbered paragraphs:

1. A nucleic acid sensor system, comprising:
   a) a first nucleic acid comprising a 3' hybridization region; and
   b) a second nucleic acid comprising a 5' hybridization region;
   wherein the first nucleic acid and the second nucleic acid, when bridged by a target nucleic acid that hybridizes to the 3' hybridization region and the 5' hybridization region, are configured to encode a non-template cassette comprising a promoter, a ribosome binding site, and a coding sequence for a reporter protein.

2. A nucleic acid sensor system, comprising:
   a) a first nucleic acid comprising a 3' hybridization region; and
   b) a second nucleic acid comprising a 5' hybridization region;
   wherein the first nucleic acid and the second nucleic acid, when ligated together, are configured to encode a non-template cassette comprising a promoter, a ribosome binding site, and a coding sequence for a reporter protein.

3. A nucleic acid sensor system, comprising:
   a) a first nucleic acid comprising a 3' hybridization region; and
   b) a second nucleic acid comprising a 5' hybridization region;
   wherein the first nucleic acid and the second nucleic acid, when ligated together and hybridized to a target nucleic acid that hybridizes to the 3' hybridization region and the 5' hybridization region, are configured to encode a non-template cassette comprising a promoter, a ribosome binding site, and a coding sequence for a reporter protein.

4. A nucleic acid sensor system comprising a non-functional, single-stranded, non-template form of a DNA expression cassette comprising:

i) a promoter;
   ii) a ribosome binding site (RBS); and
   iii) a coding sequence for a reporter protein;
   wherein a target nucleic acid hybridization sequence is located within the cassette, and the cassette is separated into a first nucleic acid and second nucleic acid wherein the separation occurs within the hybridization region.

5. The nucleic acid sensor system of any of paragraphs 1-4, wherein either the first or second nucleic acid comprise the coding sequence for a reporter protein and the remaining nucleic acid comprises the promoter.

6. The nucleic acid sensor system of any of paragraphs 1-5, wherein either the first or second nucleic acid comprise the coding sequence for a reporter protein and the remaining nucleic acid comprises the promoter and ribosome binding site.

7. The nucleic acid sensor system of any of paragraphs 1-6, wherein either the first or second nucleic acid comprises the promoter, the ribosome binding site, and a start codon of the coding sequence for the reporter protein and the remaining nucleic acid comprises the remaining coding sequence for the reporter protein.

8. The nucleic acid sensor system of paragraph 7, wherein the first nucleic acid comprises, from 5' to 3':
   i) the promoter;
   ii) the ribosome binding site (RBS);
   iii) the start codon for the coding sequence for the reporter protein; and
   iv) the 3' hybridization region in the form of a reading frame in-frame with the start codon;
   and the second nucleic acid comprises from 5' to 3':
   i) the 5' hybridization region in the form of a reading frame in frame with the remaining coding sequence for the reporter protein; and
   ii) a remaining coding sequence for the reporter protein linked downstream of and in-frame with the 5' hybridization region.

9. The nucleic acid sensor system of any of paragraphs 1-8, wherein either the first or second nucleic acid comprises the promoter and the remaining nucleic acid comprises the ribosome binding site and coding sequence for the reporter protein.

10. The nucleic acid sensor system of paragraph 9, wherein the first nucleic acid comprises, from 5' to 3':
   i) the promoter; and
   ii) the 3' hybridization region;
   and the second nucleic acid comprises from 5' to 3':
   i) the 5' hybridization region;
   ii) the ribosome binding sequence; and
   iii) the coding sequence for the reporting protein.

11. The nucleic acid sensor system of any of paragraphs 1-10, wherein either the first or second nucleic acid comprises the promoter, the ribosome binding site, and a 5' portion of the coding sequence for the reporter protein and the remaining nucleic acid comprises the remaining coding sequence for the reporter protein.

12. The nucleic acid sensor system of paragraph 11, wherein the first nucleic acid comprises, from 5' to 3':
   i) the promoter;
   ii) the RBS;
   iii) a first portion of the coding sequence for the reporter protein, comprising a start codon and at least one additional codon; and iv) the 3' hybridization region in the form of a reading frame in-frame with the start codon;

and the second nucleic acid comprises from 5' to 3':

i) the 5' hybridization region in the form of a reading frame in-frame with the first portion of the coding sequence for the reporter protein and in-frame with the second portion of the coding sequence for the reporter protein; and ii) a second portion of the coding sequence for the reporter protein linked downstream of and in-frame with the 5' hybridization region.

13. The nucleic acid sensor system of any of paragraphs 11-12, wherein the 3' hybridization region and 5' hybridization region are located in the coding sequence of the reporter protein.

14. The nucleic acid sensor system of any of paragraphs 11-13, wherein the 3' hybridization region and 5' hybridization region are located within a region encoding for a solvent exposed loop of the reporter protein.

15. The nucleic acid sensor system of any of paragraphs 11-14, wherein the 3' hybridization region and 5' hybridization region are located in the coding sequence of the reporter protein and do not substantially impact reporter gene function.

16. The nucleic acid sensor system of any of paragraphs 1-15, wherein the first nucleic acid and the second nucleic acid are DNA.

17. The nucleic acid sensor system of any of paragraphs 1-16, wherein the second nucleic acid comprises a 5' phosphate.

18. The nucleic acid sensor system of any of paragraphs 1-17, wherein at least a portion of the 3' hybridization region is in the promoter, the ribosome binding site, or the coding sequence.

19. The nucleic acid sensor system of any of paragraphs 1-18, wherein at least a portion of the 5' hybridization region is in the promoter, the ribosome binding site, or the coding sequence.

20. The nucleic acid sensor system of any of paragraphs 1-19, wherein the 3' hybridization region is not within or co-extensive with the promoter, the ribosome binding site, or the coding sequence.

21. The nucleic acid sensor system of any of paragraphs 1-20, wherein the 3' hybridization region is 3' of any promoter, ribosome binding site, or coding sequence in the first nucleic acid.

22. The nucleic acid sensor system of any of paragraphs 1-21, wherein the 5' hybridization region is not within or co-extensive with the promoter, the ribosome binding site, or the coding sequence.

23. The nucleic acid sensor system of any of paragraphs 1-22, wherein the 5' hybridization region is 5' of any promoter, ribosome binding site, or coding sequence in the second nucleic acid.

24. The nucleic acid sensor system of any of paragraphs 1-23, wherein the two hybridization regions are collectively at least 12 nucleotides in length.

25. The nucleic acid sensor system of any of paragraphs 1-24, wherein the 5' and 3' hybridization regions are each at least 6 nucleotides in length.

26. The nucleic acid sensor system of any of paragraphs 1-25, wherein the first and second nucleic acids are separate molecules.

27. The nucleic acid sensor system of any of paragraphs 1-26, wherein the 5' end of the first nucleic acid is linked to the 3' end of the second nucleic acid through intervening ssDNA sequences so that the first and second nucleic acids are present on a single DNA sequence or strand.

28. The nucleic acid sensor system of any of paragraphs 1-27, wherein the 5' end of the first nucleic acid further comprises a sequence that forms a terminal hairpin loop.

29. The nucleic acid sensor system of any of paragraphs 1-28, wherein the system further comprises a primer complementary to a 3' region of the second nucleic acid.

30. The nucleic acid sensor system of any of paragraphs 1-29, wherein the system further comprises a primer complementary to a sequence which is 3' of any promoter, ribosome binding site, or coding sequence in the second nucleic acid.

31. The nucleic acid sensor system of any of paragraphs 1-30, wherein the second nucleic acid further comprises a nucleotide sequence at its 3' end comprising the primer in a terminal hairpin loop.

32. The nucleic acid sensor system of any of paragraphs 1-31, wherein the reporter protein is selected from the group consisting of luciferase, nanoluciferase, beta-lactamase, beta-galactosidase, horseradish peroxidase, alkaline phosphatase, catalase, carbonic anhydrase, green fluorescent protein, red fluorescent protein, cyan fluorescent protein, yellow fluorescent protein, trypsin, a protease, and a peptide that complements and activates a truncated reporter protein.

33. The nucleic acid system of any of paragraphs 1-32, further comprising a cell free expression system.

34. The nucleic acid system of any of paragraphs 1-33, further comprising a ligase.

35. The nucleic acid system of any of paragraphs 1-34, further comprising a reverse transcriptase.

36. The nucleic acid system of any of paragraphs 1-35, further comprising a ribonuclease that hydrolyzes RNA which is hybridized to DNA.

37. The nucleic acid system of any of paragraphs 1-36, wherein the ribonuclease is RNAse H.

38. The nucleic acid system of any of paragraphs 1-37, further comprising:

a) a single-stranded DNA (ssDNA) primer complementary to i) a 3' region of the expression cassette, ii) a 3' region of the second nucleic acid, iii) a sequence which is 3' of any promoter, ribosome binding site, or coding sequence in the second nucleic acid, or iv) a sequence which is 3' of any promoter, ribosome binding site, or coding sequence in the expression cassette;

b) a ligase; and c) a cell-free expression system.

39. The nucleic acid sensor system of any of paragraphs 1-38, further comprising one or more of ligase, a strand-displacing DNA polymerase, dNTPs, RNAse inhibitor, and a cell free expression system.

40. The nucleic acid sensor system of any of paragraphs 33-39, wherein the cell free expression system is whole cell extract.

41. The nucleic acid sensor system of any of paragraphs 1-40, wherein the DNA polymerase is selected from the group consisting of a Klenow fragment with exonuclease portion, a Klenow fragment without the exonuclease portion, a phi29 polymerase, a modified T7 DNA polymerase, a polymerase from *Psychrobacillus*, a polymerase from *Psychrobacillus* with enhanced strand displacement, and a polymerase from *B. subtilis*.

42. The nucleic acid sensor system of any of paragraphs 1-41, wherein the junction is configured to hybridize against a polymorphism of the target nucleic acid.

43. The nucleic acid sensor system of any of paragraphs 1-42, wherein the 3' or 5' hybridization region is configured to hybridize to a polymorphism of the target nucleic acid.

44. The nucleic acid sensor system of any of paragraphs 1-43, wherein the free end of the 3' or 5' hybridization region is configured to hybridize to a polymorphism of the target nucleic acid.

45. The nucleic acid sensor system of any of paragraphs 1-44, wherein the polymorphism is located at one or both of the two bases at the junction of the hybridization region, on either or both the upstream or downstream ssDNA sensor domain.

46. The nucleic acid sensor system of any of paragraphs 1-45, wherein the hybridization region comprises one or more polymorphisms.

47. A nucleic acid sensor system, comprising:
a) a first domain comprising a 3' hybridization region; and
b) a second domain comprising a 5' hybridization region;
wherein the first domain and the second domain, when bridged by a target nucleic acid that hybridizes to the 3' hybridization region and the 5' hybridization region, are configured to encode a non-template cassette comprising a promoter, a ribosome binding site, and a coding sequence for a reporter protein.

48. A nucleic acid sensor system, comprising:
a) a first domain comprising a 3' hybridization region; and
b) a second domain comprising a 5' hybridization region;
wherein the first domain and the second domain, when ligated together, are configured to encode a non-template cassette comprising a promoter, a ribosome binding site, and a coding sequence for a reporter protein.

49. A nucleic acid sensor system, comprising:
a) a first domain comprising a 3' hybridization region; and
b) a second domain comprising a 5' hybridization region;
wherein the first domain and the second domain, when ligated together and hybridized to a target nucleic acid that hybridizes to the 3' hybridization region and the 5' hybridization region, are configured to encode a non-template cassette comprising a promoter, a ribosome binding site, and a coding sequence for a reporter protein.

50. A nucleic acid sensor system comprising a single-stranded, non-template form of a DNA expression cassette comprising:
i) a promoter;
ii) a ribosome binding site (RBS); and
iii) a coding sequence for a reporter protein;
wherein a target nucleic acid hybridization sequence is located within the cassette, and the cassette is separated into or comprises a first domain and a second domain wherein the separation or transition between domains occurs within the hybridization region.

51. The nucleic acid sensor system of any of paragraphs 47-50, wherein either the first or second domain comprise the coding sequence for a reporter protein and the remaining domain comprises the promoter.

52. The nucleic acid sensor system of any of paragraphs 47-51, wherein either the first or second domain comprise the coding sequence for a reporter protein and the remaining domain comprises the promoter and ribosome binding site.

53. The nucleic acid sensor system of any of paragraphs 47-52, wherein either the first or second domain comprises the promoter, the ribosome binding site, and a start codon of the coding sequence for the reporter protein and the remaining domain comprises the remaining coding sequence for the reporter protein.

54. The nucleic acid sensor system of paragraph 53, wherein the first domain comprises, from 5' to 3':
i) the promoter;
ii) the ribosome binding site (RBS);
iii) the start codon for the coding sequence for the reporter protein; and
iv) the 3' hybridization region in the form of a reading frame in-frame with the start codon;
and the second domain comprises from 5' to 3':
i) the 5' hybridization region in the form of a reading frame in frame with the remaining coding sequence for the reporter protein; and
ii) a remaining coding sequence for the reporter protein linked downstream of and in-frame with the 5' hybridization region.

55. The nucleic acid sensor system of any of paragraphs 47-54, wherein either the first or second domain comprises the promoter and the remaining domain comprises the ribosome binding site and coding sequence for the reporter protein.

56. The nucleic acid sensor system of paragraph 55, wherein the first domain comprises, from 5' to 3':
i) the promoter; and
ii) the 3' hybridization region;
and the second domain comprises, from 5' to 3':
i) the 5' hybridization region;
ii) the ribosome binding sequence; and
iii) the coding sequence for the reporting protein.

57. The nucleic acid sensor system of any of paragraphs 47-56, wherein either the first or second domain comprises the promoter, the ribosome binding site, and a 5' portion of the coding sequence for the reporter protein and the remaining domain comprises the remaining coding sequence for the reporter protein.

58. The nucleic acid sensor system of paragraph 57, wherein the first domain comprises, from 5' to 3':
i) the promoter;
ii) the RBS;
iii) a first portion of the coding sequence for the reporter protein, comprising a start codon and at least one additional codon; and
iv) the 3' hybridization region in the form of a reading frame in-frame with the start codon;
and the second domain comprises, from 5' to 3':
i) the 5' hybridization region in the form of a reading frame in-frame with the first portion of the coding sequence for the reporter protein and in-frame with the second portion of the coding sequence for the reporter protein; and
ii) a second portion of the coding sequence for the reporter protein linked downstream of and in-frame with the 5' hybridization region.

59. The nucleic acid sensor system of any of paragraphs 57-58, wherein the 3' hybridization region and 5' hybridization region are located in the coding sequence of the reporter protein, within a region encoding for a solvent exposed loop of the reporter protein.

60. The nucleic acid system of any of paragraphs 57-59, wherein the 3' hybridization region and 5' hybridization region are located in the coding sequence of the reporter protein and do not substantially impact reporter gene function.

61. The nucleic acid sensor system of any of paragraphs 47-60, wherein the first domain and the second domain are DNA.

62. The nucleic acid sensor system of any of paragraphs 47-61, wherein at least a portion of the 3' hybridization region is in the promoter, the ribosome binding site, or the coding sequence.

63. The nucleic acid sensor system of any of paragraphs 47-62, wherein at least a portion of the 5' hybridization region is in the promoter, the ribosome binding site, or the coding sequence.

64. The nucleic acid sensor system of any of paragraphs 47-63, wherein the 3' hybridization region is not within or co-extensive with the promoter, the ribosome binding site, or the coding sequence.

65. The nucleic acid sensor system of any of paragraphs 47-64, wherein the 3' hybridization region is 3' of any promoter, ribosome binding site, or coding sequence in the first domain.

66. The nucleic acid sensor system of any of paragraphs 47-65, wherein the 5' hybridization region is not within or co-extensive with the promoter, the ribosome binding site, or the coding sequence.

67. The nucleic acid sensor system of any of paragraphs 47-66, wherein the 5' hybridization region is 5' of any promoter, ribosome binding site, or coding sequence in the second domain.

68. The nucleic acid sensor system of any of paragraphs 47-67, wherein the two hybridization regions are collectively at least 12 nucleotides in length.

69. The nucleic acid sensor system of any of paragraphs 47-68, wherein the 5' and 3' hybridization regions are each at least 6 nucleotides in length.

70. The nucleic acid sensor system of any of paragraphs 47-69, wherein the first and second domains are on the same molecule.

71. The nucleic acid sensor system of any of paragraphs 47-70, wherein the 5' end of the first domain is linked to the 3' end of the second domain through intervening ssDNA sequences so that the first and second domain are present on a single DNA sequence or strand.

72. The nucleic acid sensor system of any of paragraphs 47-71, wherein the 5' end of the first domain further comprises a sequence that forms a terminal hairpin loop.

73. The nucleic acid sensor system of any of paragraphs 47-72, wherein the system further comprises a primer complementary to a 3' region of the second domain.

74. The nucleic acid sensor system of any of paragraphs 47-73, wherein the system further comprises a primer complementary to a sequence which is 3' of any promoter, ribosome binding site, or coding sequence in the second domain.

75. The nucleic acid sensor system of any of paragraphs 47-74, wherein the second domain further comprises a nucleotide sequence at its 3' end comprising the primer in a terminal hairpin loop.

76. The nucleic acid sensor system of any of paragraphs 47-75, wherein the reporter protein is selected from the group consisting of luciferase, nanoluciferase, beta-lactamase, beta-galactosidase, horseradish peroxidase, alkaline phosphatase, catalase, carbonic anhydrase, green fluorescent protein, red fluorescent protein, cyan fluorescent protein, yellow fluorescent protein, trypsin, a protease, and a peptide that complements and activates a truncated reporter protein.

77. The nucleic acid system of any of paragraphs 47-76, further comprising a cell free expression system.

78. The nucleic acid system of any of paragraphs 47-77, further comprising a ligase.

79. The nucleic acid system of any of paragraphs 47-78, further comprising a reverse transcriptase.

80. The nucleic acid system of any of paragraphs 47-79, further comprising a ribonuclease that hydrolyzes RNA which is hybridized to DNA.

81. The nucleic acid system of any of paragraphs 47-80, wherein the ribonuclease is RNAse H.

82. The nucleic acid system of any of paragraphs 47-81, further comprising:
   a) a single-stranded DNA primer complementary to i) a 3' region of the expression cassette, ii) a 3' region of the second nucleic acid, iii) a sequence which is 3' of any promoter, ribosome binding site, or coding sequence in the second nucleic acid, or iv) a sequence which is 3' of any promoter, ribosome binding site, or coding sequence in the expression cassette;
   b) a ligase; and
   c) a cell-free expression system.

83. The nucleic acid sensor system of any of paragraphs 47-82, further comprising one or more of ligase, a strand-displacing DNA polymerase, dNTPs, RNAse inhibitor, and a cell free expression system.

84. The nucleic acid sensor system of any of paragraphs 77-83, wherein the cell free expression system is whole cell extract.

85. The nucleic acid sensor system of any of paragraphs 47-84, wherein the DNA polymerase is selected from the group consisting of a Klenow fragment with exonuclease portion, a Klenow fragment without the exonuclease portion, a phi29 polymerase, a modified T7 DNA polymerase, a polymerase from *Psychrobacillus*, a polymerase from *Psychrobacillus* with enhanced strand displacement, and a polymerase from *B. subtilis*.

86. The nucleic acid sensor system of any of paragraphs 47-85, wherein the junction is configured to hybridize against a polymorphism of the target nucleic acid.

87. The nucleic acid sensor system of any of paragraphs 47-86, wherein the 3' or 5' hybridization region is configured to hybridize to a polymorphism of the target nucleic acid.

88. The nucleic acid sensor system of any of paragraphs 47-87, wherein the free end of the 3' or 5' hybridization region is configured to hybridize to a polymorphism of the target nucleic acid.

89. The nucleic acid sensor system of any of paragraphs 47-88, wherein the polymorphism is located at one or both of the two bases at the junction of the hybridization region, on either or both the upstream or downstream ssDNA sensor domain.

90. The nucleic acid sensor system of any of paragraphs 47-89, wherein the hybridization region comprises one or more polymorphisms.

91. A method for detecting a target nucleic acid in a sample, comprising:
   a) providing a nucleic acid sensor system of any of paragraphs 1-90, in which an upstream hybridization region and a downstream hybridization region are complementary to a portion of the target nucleic acid such that hybridization of the target nucleic acid to the upstream and downstream hybridization regions creates a junction between the first and second nucleic acids or first and second domains;

b) contacting the nucleic acid sensor system with the sample in the presence of ligase under conditions appropriate for hybridization of the target nucleic acid with the upstream and downstream hybridization regions and ligation of the upstream and downstream hybridization regions, to thereby produce an operably-linked ssDNA reaction product;

c) contacting the reaction product produced in step b) to a cell free expression system comprising a DNA polymerase, dNTPs and other building block components necessary for mRNA and protein production, and a ssDNA primer under conditions appropriate for DNA polymerization, RNA transcription, and RNA translation to thereby produce a reporter protein;

d) measuring the reporter protein present to indicate the presence of the target nucleic acid in the sample.

92. A method for detecting a target nucleic acid in a sample, comprising:

a) providing a nucleic acid sensor system of any of paragraphs 1-90, in which the 3' hybridization region and the 5' hybridization region are complementary to a portion of the target nucleic acid such that hybridization of the target nucleic acid to the two hybridization regions creates a junction between the first and second nucleic acids;

b) contacting the nucleic acid sensor system with the sample in the presence of ligase under conditions appropriate for hybridization of the target nucleic acid with the 3' hybridization region and 5'hybridization regions and ligation of the hybridization regions, to thereby produce a reaction product comprising a strand of the target nucleic acid hybridized to a nucleic strand comprising the operably-linked first and second nucleic acids;

c) contacting the reaction product produced in step b) with a cell free expression system to thereby produce a reporter protein;

d) measuring the reporter protein produced in step c) to determine the amount of the target nucleic acid in the sample.

93. The method of any of paragraphs 91-92, wherein components of the nucleic acid sensor system are each present at about 16 nM.

94. The method of any of paragraphs 91-93, wherein ligase is present at about 100 nM.

95. The method of any of paragraphs 91-94, wherein step b) is incubated for a period of from 5 minutes to 15 minutes at ambient temperature (24-26° C.) and/or step c) is incubated for a period of time from 60 minutes to 3 hours, at ambient temperature.

96. The method of any of paragraphs 91-95, wherein the cell free expression system further comprises an RNase inhibitor.

97. The method of any of paragraphs 91-96, wherein the cell free expression system further comprises 12.5 μM ssDNA primer complementary to the 3' end of the second nucleic acid or the second domain.

98. The method of any of paragraphs 91-97, wherein the cell free expression system further comprises a reporter protein substrate.

99. The method of any of paragraphs 91-98, wherein the concentration of dNTPs is about 230 uM.

100. The method of any of paragraphs 91-99, wherein the DNA polymerase is selected from the group consisting of a Klenow fragment with exonuclease portion, a Klenow fragment without the exonuclease portion, a phi29 polymerase, a modified T7 DNA polymerase, a polymerase from *Psychrobacillus*, a polymerase from *Psychrobacillus* with enhanced strand displacement, and a polymerase from *B. subtilis*.

101. The method of any of paragraphs 91-100, wherein the reporter protein is luciferase and the reporter protein substrate is a luciferase substrate and measuring is by detection of luminescence in the cell free expression system.

102. The method of any of paragraphs 91-101, wherein transcription further comprises hybridization of the ssDNA primer to the RNA transcript, reverse transcription using a reverse transcriptase, and endolytic cleavage.

103. The method of any of paragraphs 91-102, wherein the junction is configured to hybridize against a polymorphism of the target nucleic acid.

104. The method of any of paragraphs 91-103, wherein the 3' or 5' hybridization region is configured to hybridize to a polymorphism of the target nucleic acid.

105. The method of any of paragraphs 91-104, wherein the free end of the 3' or 5' hybridization region is configured to hybridize to a polymorphism of the target nucleic acid.

106. The method of any of paragraphs 91-105, wherein the polymorphism is located at one or both of the two bases at the junction of the hybridization region, on either or both the upstream or downstream ssDNA sensor domain.

107. The method of any of paragraphs 91-106, wherein one or more polymorphisms may be optionally introduced within the hybridization region.

Some embodiments of the technology described herein can be defined according to any of the following numbered paragraphs:

1. A nucleic acid sensor system comprising a first and second single stranded DNA sensor parts which, when ligated together generate a single strand of a DNA expression cassette that comprises:

i) a promoter;

ii) a ribosome binding site (RBS); and iii) a coding sequence;

wherein a target nucleic acid hybridization sequence is located within the first and second single stranded DNA sensor parts.

2. A nucleic acid sensor system comprising a first and second single stranded DNA sensor parts which, when ligated together generate a single strand of a DNA expression cassette that comprises:

i) a promoter;

ii) a ribosome binding site (RBS);

iii) a coding sequence, which single strand comprises:

iv) a target nucleic acid hybridization sequence comprising a 3' and 5' hybridization regions, wherein the 3' hybridization region is included in the first sensor part and the 5' hybridization region is included in the second sensor part so that, when the sensor system is contacted with a sample that includes a target nucleic acid that hybridizes with the target nucleic acid sequence, hybridization with the target nucleic acid enables ligation of the first and second parts to generate the single strand.

3. The nucleic acid sensor system of any of paragraphs 1-2, wherein the DNA expression cassette is a non-template DNA expression cassette.

4. The nucleic acid sensor system of any of paragraphs 1-3, wherein the first and second sensor parts of the expression cassette are separated at any given position within the expression cassette.

5. The nucleic acid sensor system of paragraph 4, wherein the separation occurs within the target nucleic acid hybridization sequence.

6. The nucleic acid sensor system of any of paragraphs 1-4, wherein the target nucleic acid hybridization sequence is located at any given position within the expression cassette.

7. The nucleic acid sensor system of any of paragraphs 1-6, wherein either the first or the second sensor part comprises the coding sequence and the remaining sensor part comprises the promoter.

8. The nucleic acid sensor system of any of paragraphs 1-7, wherein either the first or the second sensor part comprises the promoter and the ribosome binding site and the remaining sensor part comprises the coding sequence.

9. The nucleic acid sensor system of any of paragraphs 1-8, wherein either the first or the second sensor part comprises the promoter, the ribosome binding site, and a start codon of the coding sequence and the remaining sensor part comprises the remaining coding sequence.

10. The nucleic acid sensor system of paragraph 9, wherein the first sensor part comprises, from 5' to 3':
   i) the promoter;
   ii) the ribosome binding site (RBS);
   iii) the start codon for the coding sequence; and
   iv) the 3' hybridization region in the form of a reading frame in-frame with the start codon;
and the second sensor part comprises from 5' to 3':
   i) the 5' hybridization region in the form of a reading frame in-frame with the remaining coding sequence; and
   ii) a remaining coding sequence linked downstream of and in-frame with the 5' hybridization region.

11. The nucleic acid sensor system of any of paragraphs 1-10, wherein either the first or the second sensor part comprises the promoter and the remaining sensor part comprises the ribosome binding site and the coding sequence.

12. The nucleic acid sensor system of paragraph 11, wherein the first sensor part comprises, from 5' to 3':
   i) the promoter; and
   ii) the 3' hybridization region;
and the second sensor part comprises, from 5' to 3':
   i) the 5' hybridization region;
   ii) the ribosome binding sequence; and
   iii) the coding sequence.

13. The nucleic acid sensor system of any of paragraphs 1-12, wherein either the first or the second sensor part comprises the promoter, the ribosome binding site, and a 5' portion of the coding sequence and the remaining sensor part comprises the remaining coding sequence.

14. The nucleic acid sensor system of paragraph 13, wherein the first sensor part comprises, from 5' to 3':
   i) the promoter;
   ii) the RBS;
   iii) a first portion of the coding sequence, comprising a start codon and at least one additional codon;
   iv) the 3' hybridization region in the form of a reading frame in-frame with the start codon;
and the second sensor part comprises, from 5' to 3':
   i) the 5' hybridization region in the form of a reading frame in-frame with the first portion of the coding sequence and in-frame with the second portion of the coding sequence; and
   ii) a second portion of the coding sequence linked downstream of and in-frame with the 5' hybridization region.

15. The nucleic acid sensor system of any of paragraphs 1-14, wherein at least a portion of the 3' hybridization region is in the promoter, the ribosome binding site, or the coding sequence.

16. The nucleic acid sensor system of any of paragraphs 1-15, wherein at least a portion of the 5' hybridization region is in the promoter, the ribosome binding site, or the coding sequence.

17. The nucleic acid sensor system of any of paragraphs 1-16, wherein the 3' hybridization region is not within the promoter, the ribosome binding site, or the coding sequence.

18. The nucleic acid sensor system of any of paragraphs 1-17, wherein the 3' hybridization region is 3' of any promoter, ribosome binding site, or coding sequence in the first sensor part.

19. The nucleic acid sensor system of any of paragraphs 1-18, wherein the 5' hybridization region is not within the promoter, the ribosome binding site, or the coding sequence.

20. The nucleic acid sensor system of any of paragraphs 1-19, wherein the 5' hybridization region is 5' of any promoter, ribosome binding site, or coding sequence in the second sensor part.

21. The nucleic acid sensor system of any of paragraphs 1-20, wherein the 3' hybridization region and the 5' hybridization region are collectively at least 12 nucleotides in length.

22. The nucleic acid sensor system of any of paragraphs 1-21, wherein the 3' hybridization region and the 5' hybridization region are each at least 6 nucleotides in length.

23. The nucleic acid sensor system of any of paragraphs 1-22, wherein the first and second sensor parts are on the same molecule.

24. The nucleic acid sensor system of any of paragraphs 1-23, wherein the 5' end of the first sensor part is linked to the 3' end of the second sensor part through intervening ssDNA sequences so that the first and second sensor part form a single molecule.

25. The nucleic acid sensor system of any of paragraphs 1-24, wherein the system further comprises a primer complementary to a sequence within the non-template expression cassette or intervening ssDNA sequences.

26. The nucleic acid sensor system of any of paragraphs 1-22, wherein the first and second sensor parts are on at least two separate molecules.

27. The nucleic acid sensor system of any of paragraphs 1-22 or 26, wherein the 5' end of the first sensor part further comprises a sequence that forms a terminal hairpin loop.

28. The nucleic acid sensor system of any of paragraphs 1-22 or 26-27, wherein the system further comprises a primer complementary to a 3' region of the second sensor part.

29. The nucleic acid sensor system of any of paragraphs 23-25, wherein the system further comprises a primer complementary to a sequence which is 3' of any promoter, ribosome binding site, or coding sequence in the second sensor part.

30. The nucleic acid sensor system of any of paragraphs 23-25, wherein the system further comprises a primer complementary to a region 5' of any promoter, ribosome binding site, or coding sequence in the second sensor part.

31. The nucleic acid sensor system of any of paragraphs 1-22 and 26-30, wherein the second sensor part further comprises a nucleotide sequence at its 3' end comprising the primer in a terminal hairpin loop.

32. The nucleic acid sensor system of any of paragraphs 1-31 wherein the coding sequence of the DNA expression cassette encodes a polypeptide.

33. The nucleic acid sensor system of paragraph 32, wherein the polypeptide is a reporter protein.

34. The nucleic acid sensor system of any of paragraphs 13-14, wherein the 3' hybridization region and the 5' hybridization region are located in the coding sequence, within a region encoding for a solvent exposed loop of the reporter protein.

35. The nucleic acid sensor system of any of paragraphs 13-14 or 34, wherein the 3' hybridization region and the 5' hybridization region are located in the coding sequence of the reporter protein and do not substantially impact reporter gene function.

36. The nucleic acid sensor system of paragraph 33, wherein the reporter protein comprises a luciferase, nanoluciferase, beta-lactamase, beta-galactosidase, horseradish peroxidase, alkaline phosphatase, catalase, carbonic anhydrase, green fluorescent protein, red fluorescent protein, cyan fluorescent protein, yellow fluorescent protein, trypsin, a protease, a peptide that complements and activates a truncated reporter protein, and a polypeptide that is detectable by an assay.

37. The nucleic acid system of any of paragraphs 1-36, further comprising a cell free expression system.

38. The nucleic acid system of any of paragraphs 1-37, further comprising a ligase.

39. The nucleic acid system of any of paragraphs 1-38, further comprising a reverse transcriptase.

40. The nucleic acid system of any of paragraphs 1-39, further comprising a ribonuclease that hydrolyzes RNA which is hybridized to DNA.

41. The nucleic acid system of paragraph 40, wherein the ribonuclease is RNAse H.

42. The nucleic acid sensor system of any of paragraphs 1-41, further comprising one or more of a ligase, a strand-displacing DNA polymerase, dNTPs, RNAse inhibitor, and a cell free expression system.

43. The nucleic acid sensor system of any of paragraphs 37-42, wherein the cell free expression system is whole cell extract.

44. The nucleic acid sensor system of any of paragraphs 1-43, further comprising a DNA polymerase.

45. The nucleic acid sensor system of paragraph 44, wherein the DNA polymerase is selected from the group consisting of a Klenow fragment with exonuclease portion, a Klenow fragment without the exonuclease portion, a phi29 polymerase, a modified T7 DNA polymerase, a polymerase from *Psychrobacillus*, a polymerase from *Psychrobacillus* with enhanced strand displacement, a polymerase from *B. subtilis*, Sequenase™ Version 2.0, a Bsu DNA Polymerase Large Fragment, a Bst 3.0 DNA Polymerase, a Phusion® High-Fidelity DNA Polymerase, a Vent® DNA Polymerase without the exonuclease portion, a Vent® DNA Polymerase, a Q5® High-Fidelity DNA Polymerase, and a DNA Polymerase I Large (Klenow) Fragment.

46. The nucleic acid sensor system of any of paragraphs 1-45, wherein a polymorphism of the target nucleic acid hybridizes to a sequence at the 3' end of the first sensor part hybridization region, and 5' of the second sensor part hybridization region.

47. The nucleic acid sensor system of any of paragraphs 1-46, wherein the 3' hybridization region of the first sensor part or 5' hybridization region of the second sensor part is configured to hybridize to a polymorphism of the target nucleic acid.

48. The nucleic acid sensor system of any of paragraphs 1-47, wherein the free end of the 3' hybridization region of the first sensor part or the free end of 5' hybridization region of the second sensor part is configured to hybridize to a polymorphism of the target nucleic acid.

49. The nucleic acid sensor system of any of paragraphs 1-48, wherein the hybridization sequence of the polymorphism comprises one or both of the most 3' base of the first sensor part hybridization region and the 5' base of the second sensor part hybridization region.

50. The nucleic acid sensor system of any of paragraphs 1-49, wherein the target nucleic acid hybridization region comprises one or more polymorphisms.

51. A method for detecting a target nucleic acid in a sample, comprising:
    a) providing a sample comprising the target nucleic acid;
    b) contacting sample comprising the target nucleic acid with the nucleic acid sensor system of any of paragraphs 1-50 in the presence of a ligase under conditions favorable to the hybridization of the target nucleic acid to the 3' hybridization region of the first sensor part and to the 5' hybridization region of the second sensor part of the expression cassette, to thereby generate a reaction product comprising the target nucleic acid hybridized to the first sensor part and the second sensor part operably-linked to each other;
    c) contacting the reaction product produced in step b) with a cell-free expression system in the presence of a strand displacing DNA Polymerase and a primer, under conditions favorable to the production of a reporter protein;
    d) contacting reaction product produced in step c) with a reagent enabling the detection of the expression of the reporter protein;
    e) measuring the expression of the reporter protein produced in step d) to determine the presence and/or amount of the target nucleic acid in the sample.

52. The method of paragraph 51, wherein the ligase is provided as a part of the cell free system.

53. A method for detecting a target nucleic acid in a sample, comprising:
    a) providing a sample comprising the target nucleic acid;
    b) contacting sample comprising the target nucleic acid with the nucleic acid sensor system of any of paragraphs 1-50 in the presence of a ligase and optionally a primer under conditions favorable to the hybridization of the target nucleic acid sequence to the 3' hybridization region of the first sensor part and to the 5' hybridization region of the second sensor part of the expression cassette, to thereby generate a reaction product comprising the target nucleic acid hybridized to the first sensor part and the second sensor part operably-linked to each other;

c) contacting the reaction product produced in step b) with a cell-free expression system in the presence of a strand displacing DNA Polymerase, under conditions favorable to the production of a reporter protein;

d) contacting reaction product produced in step c) with a reagent enabling the detection of the expression of the reporter protein;

e) measuring the expression of the reporter protein produced in step d) to determine the presence and/or amount of the target nucleic acid in the sample.

54. The method of paragraph 53, wherein the ligase is provided as a part of the cell free system.

55. A method for detecting a target nucleic acid in a sample, comprising:

a) providing a sample comprising the target nucleic acid;

b) contacting sample comprising the target nucleic acid with i) the nucleic acid sensor system of any of paragraphs 1-50 in the presence of a ligase, and ii) a cell-free expression system in the presence of a strand displacing DNA Polymerase and a primer, under conditions favorable to the hybridization of the target nucleic acid to the 3' hybridization region of the first sensor part and to the 5' hybridization region of the second sensor part of the expression cassette, and to the production of a reporter protein;

c) contacting reaction product produced in step b) with a reagent enabling the detection of the expression of the reporter protein;

d) measuring the expression of the reporter protein produced in step d) to determine the presence and/or amount of the target nucleic acid in the sample.

56. The method of paragraph 55, wherein the ligase is provided as a part of the cell free system.

57. A method for detecting a target nucleic acid in a sample, comprising:

a) providing a sample comprising the target nucleic acid sequence;

b) contacting sample comprising the target nucleic acid sequence with i) the nucleic acid sensor system of any of paragraphs 1-50 in the presence of a ligase, ii) a cell-free expression system in the presence of a strand displacing DNA Polymerase and a primer, and iii) a reagent enabling the detection of the expression of the reporter protein, under conditions favorable to the hybridization of the target nucleic acid to the 3' hybridization region of the first sensor part and to the 5' hybridization region of the second sensor part of the expression cassette, and to the production of a reporter protein;

c) measuring the expression of the reporter protein produced in step b) to determine the presence and/or amount of the target nucleic acid in the sample.

58. The method of paragraph 57, wherein the ligase is provided as a part of the cell free system.

59. A kit comprising:

a) a composition comprising a nucleic acid sensor system of any of paragraphs 1-50 in a packaging material;

b) a sample collection device;

c) a positive control; and d) instructions for use.

EXAMPLES

Example 1

Nucleic Acid Sequences

All nucleic acid sequences are included in Table 1 (DNA sequence shown). Short oligonucleotide (<200 nucleotides (nt)) A parts were purchased from Integrated DNA Technologies (IDT, Coralville, IA), with PAGE purification. Longer (>200 nt) ssDNA components and RNA targets sequences were prepared from gBlocks® purchased from IDT as detailed below.

Example 2

Preparation of ssDNA Sensor Components gBlocks® are amplified using primers and Q5 PCR kit (New England Biolabs®, NEB, Ipswich, MA). 200 μL PCR reactions include 100 μL Q5 mastermix, 97 μL water, 1 μL gBlock® (10 ng/μL), 1 μL each 100 μM unlabeled forward and biotinylated reverse primer. PCR reactions are run with hot start at 98° C. for 2 min, 35 cycles of 98° C. denaturing for 10 s, 68° C. annealing for 20 s, and 72° C. extension for 30 s, followed by 72° C. final extension for 2 min. PCR reactions are pooled and purified on a DNA-25 Clean and Concentrate column from Zymo Research® (Irvine, CA), eluted into 50 μL $H_2O$ and run on a 2% E-Gel® EX (Invitrogen®, Carlsbad, CA) for confirmation. Concentration is determined on a Nanodrop® (ThermoFisher Scientific®, Waltham, MA). ssDNA constructs are purified using Dynabeads® MyOne® Streptavidin C1 magnetic beads (ThermoFisher Scientific®). Bead volume is calculated based on PCR concentration and bead binding capacity of 20 μg ds-DNA/1 mg beads, using ~20% excess beads to ensure complete binding. Beads are transferred to 2.0 mL tubes and pelleted via a particle concentrator rack (MPC®). Beads are washed twice using 1× Binding and Wash buffer (B/W, 5 mM Tris-HCl, pH 7.5, 0.5 mM EDTA, 1 M NaCl). One volume of 2×B/W is added to one volume PCR elution, and the PCR mix is added to the beads, rotating at room temperature for a minimum of 20 min. Beads are concentrated and washed twice. ssDNA is eluted two times with one volume of 100 mM cold NaOH. The eluate is neutralized with 0.1 volume 1M HCl and 0.1 volume 3M NaOAc, pH 5.0 and purified using a Zymo® Oligo Clean and Concentrate kit (Zymo Research®).

Example 3

Preparation of RNA Targets gBlocks® encoding the target RNA sequences with 5' T7 promoters were purchased from IDT® and added to the HiScribe® in vitro transcription system (NEB®), and reactions were run for approximately 4 hours. RNA is purified using a Zymo® RNA Clean and Concentrate kit (Zymo Research®) and concentration was determined using a Nanodrop®.

Example 4

Construction of Plasmid Expressing Target RNA in *E. coli* DH5α. *E. coli* cells containing the pUC19-based pgRNA-bacteria plasmid was purchased from Addgene® (plasmid #44251), grown in LB with ampicillin, and the plasmid purified by mini-prep (Zymo Research®). The DNA sequence encoding a target RNA was inserted into the vector using Q5 site-directed mutagenesis (NEB®) and verified with colony PCR.

Example 5

Preparation of RNA Extracts

DH5α *E. coli* cells transformed with a plasmid expressing an RNA target sequence were grown at 37° C. until OD$_{600}$ of 0.3. 0.75 mL of TRIzol® LS Reagent (Thermo Fisher®) was added to 250 µL of cells and mixed via pipetting. This mixture was incubated at room temperature for 5 min. 0.2 mL of chloroform was added and cells were left to sit for 3 min. Next, the reaction was centrifuged for 15 min @ 12000×g and 4° C. After centrifugation, the aqueous phase (top phase) was added to a Zymo® RNA Clean and Concentrate (Zymo Research®) purification column and eluted in 25 µL. The purified RNA was treated with DNase I and added to another RNA purification column to generate the RNA extract. Whole cell extracts were obtained from *E. coli* cells that were grown to the same 0.3 OD, pelleted and concentrated 10× during resuspension in RNA storage buffer (Invitrogen®, 1 mM sodium citrate, pH 6.4). Cells were heat lysed by incubation at 95° C. for 5 min.

Example 6

Standard Detection Assay Conditions 0.41 units of PBCV-1 DNA ligase, 3 µM reverse primer, 50 mM Tris-HCl, 10 mM MgCl$_2$, 1 mM ATP, and 10 mM DTT are combined with 38 nM each part A and B sensor components in 1.2 µL and incubated at room temperature (24-26° C.) for 5-15 minutes as indicated. After the sensor binding and ligation reaction, 1.6 µl of a cell-free expression and substrate mix comprised of 0.45 v/v PURExpress solution A (NEB®), 0.34 v/v PURExpress solution B (NEB), 0.91 units murine RNase inhibitor (NEB®), 228 µM dNTPs mix (NEB®), 0.02 v/v Nano-Glo® substrate (Promega®), and 0.125 units DNA polymerase is added and the expression reaction is sealed with optically clear film and endpoint reads are taken on a Biotek® (Winooski, VT) Synergy NEO plate reader at 100 gain. Any modifications are noted in the example descriptions below.

Example 7

As illustrated in FIG. 1, key components of the system include:
   a single-stranded DNA 'A' domain,
   a single-stranded DNA 'B' domain that is 5' phosphorylated
   a ssDNA primer that hybridizes to the 3' end of the B domain,
   a ligase,
   a DNA polymerase, and
   a cell-free expression system.

Example 8

Disruption of the Expression Cassette.

Figure 2A:
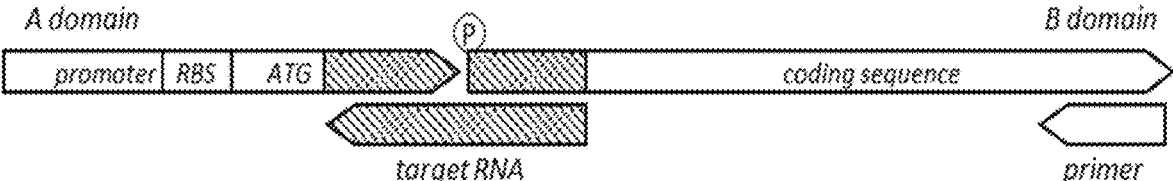
FIG. 2A-FIG. 2B: Illustrations showing nucleic acid components of sensor system.

A double stranded DNA expression cassette consisting of a T7 promoter, ribosome binding site (RBS), and the coding sequence of a luciferase reporter protein was disrupted by splitting the expression cassette into two separate parts—the upstream (or A) part and the downstream (or B) part (see e.g., FIG. 2A). Three versions of the split expression cassette include:

Version 1 (v1)—split after the start codon (ATG) of the coding sequence,
   Version 2 (v2)—split between the promoter and the RBS, and
   Version 3 (v3)—split embedded within a loop or turn of the reporter protein The v1 and v2 constructs include an inserted region of 36 nucleotides at the split site designed to bind to a target 36 nucleotide RNA sequence; 18 nucleotides of the inserted hybridization region are on the 3' end of the A part and 18 nucleotides of the hybridization region are on the 5' end of the B part. Two constructs for each of the v1 and v2 designs were created to target two different RNA molecules (T1 and T2). The v3 construct does not include an inserted hybridization region, and a target RNA was designed to be complementary to the region of the split site. Sensor ssDNA parts for each of the versions described above are illustrated in FIG. 3. DNA sequences of all constructs and targets are listed in Table 1.

Figure 4A:
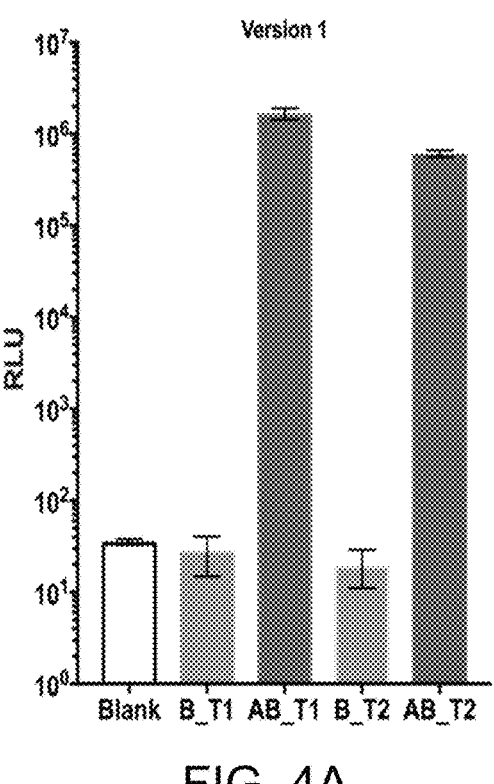
FIG. 4A-FIG. 4C: Bar graphs showing measured luminescence of intact dsDNA expression cassette (AB) versus individual dsDNA A or B parts (B_T1, B_T2, A_T3) for each design version.
Figure 4B:
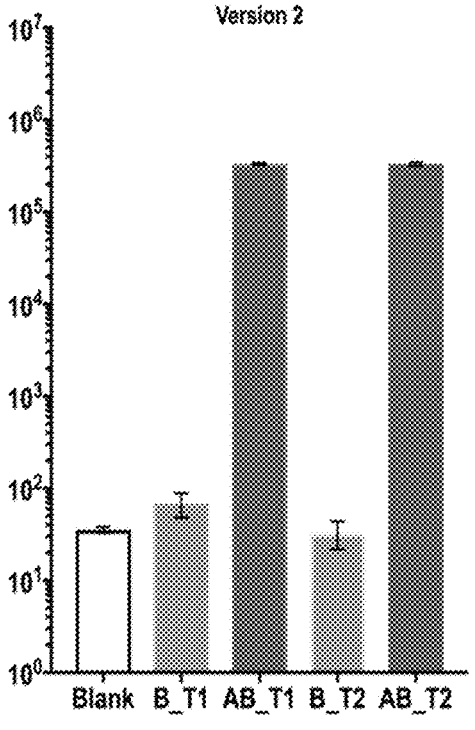
Figure 4C:
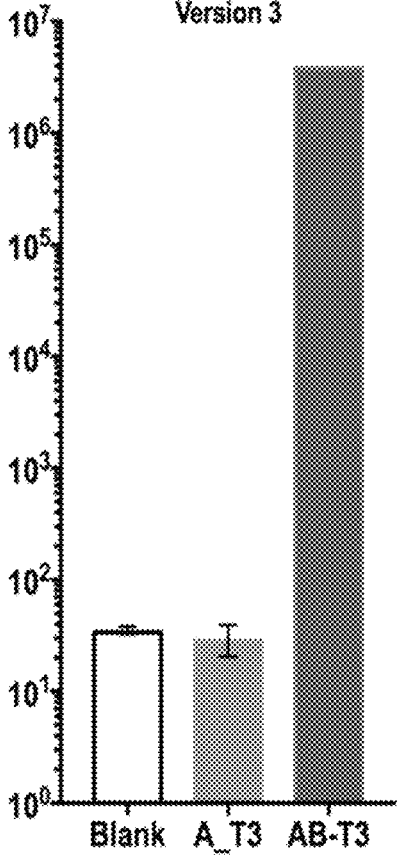

Full, intact dsDNA expression cassettes for v1, v2, and v3, and their respective dsDNA A or B parts were generated by PCR. Linear products were added to a cell-free expression system to monitor transcription, translation, and activity of a luciferase reporter by measuring luminescence (see e.g., FIG. 4A-FIG. 4C). PCR products (12.5 nM) were added directly to a cell-free expression system (PURExpress®, NEB®) supplemented with 200 µM dNTPs, 0.22 mg/ml BSA and Nano-Glo® substrate (Promega®) and incubated at ambient temperature (24-26° C.) for one hour. Luminescence was measured for three separate reactions, as well as for blank wells, using a plate reader.

Example 9

Sensitive Detection of Target RNA with Version I Sensor System.

Figure 5A:
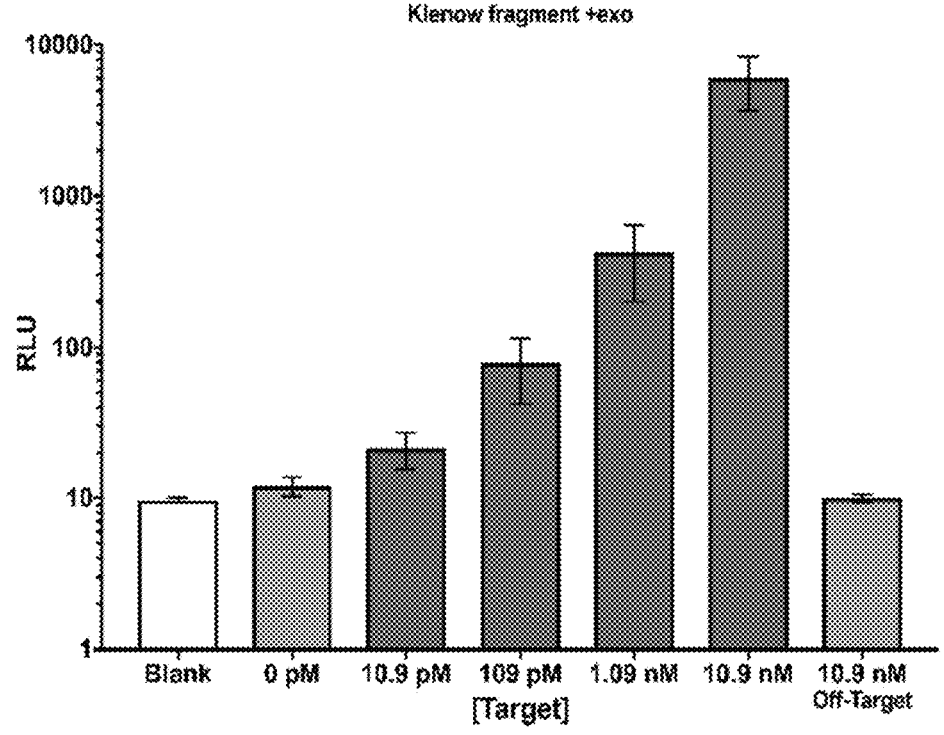
FIG. 5A-FIG. 5B: Bar graphs showing detection of different amounts of target RNA (T2) by Version 1 (v1) sensor system. Reactions included target RNA at concentrations from 0 pM to 10.9 nM. A non-complementary RNA sequence (off-target) was also tested at 10.9 nM.
Figure 5B:
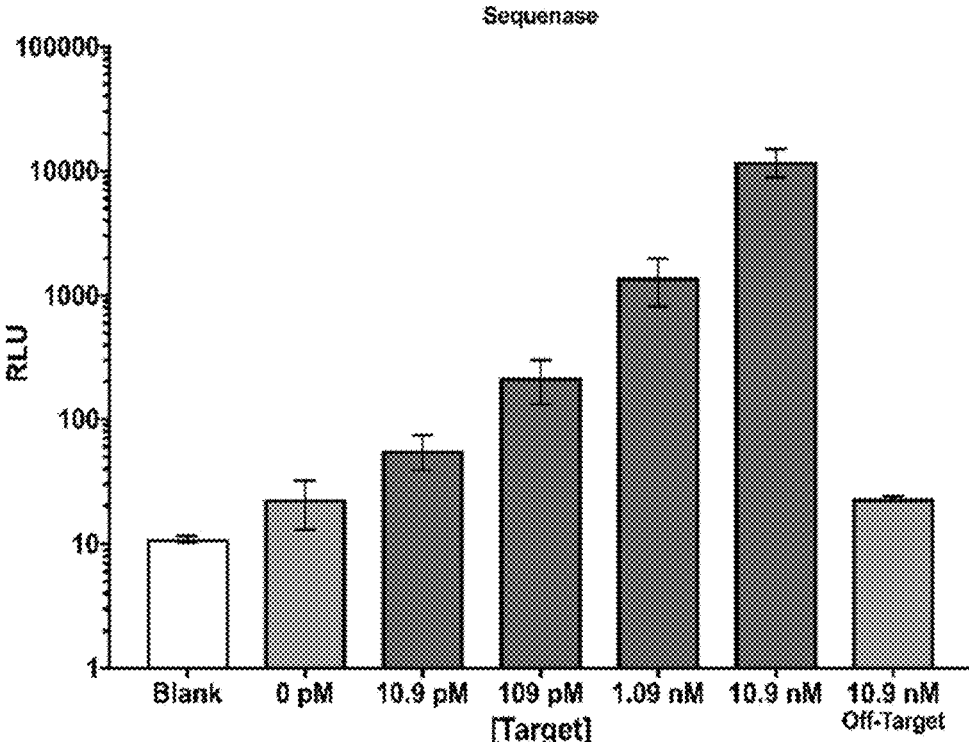

The v1 sensor system (FIG. 3) was tested for activation based on the presence of cognate RNA target sequences bridging separate ssDNA A and B parts. An additional off-target RNA sequence that is not complementary to the target hybridization site was also tested. Data showing v1 sensor detection of RNA target (T2) with a 5-minute ligation followed by a 1-hour expression reaction are shown in FIG. 5A-FIG. 5B. The performance of two different DNA polymerases were tested, Klenow fragment +exo (see e.g., FIG. 5A) and Sequenase™ (see e.g., FIG. 5B).

Figure 6:
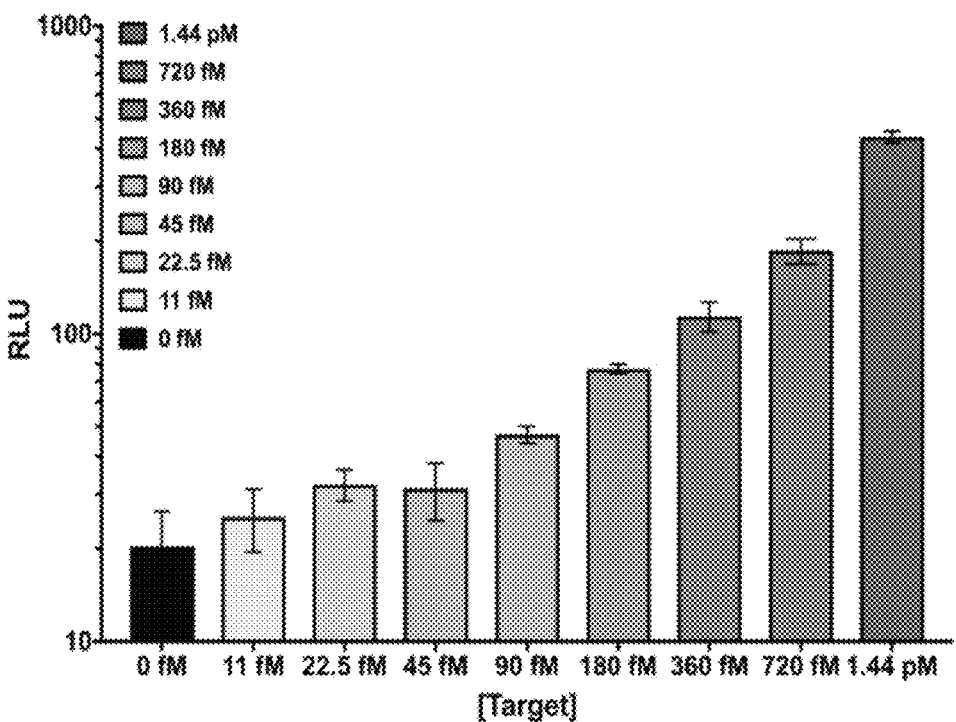
FIG. 6: Bar graph showing detection of different amounts of target T1 RNA by v1 sensor system. Reactions included target RNA at concentrations from 0 to 1.44 pM. The ligation step in these reactions was 15 minutes and luminescence was measured after 1 hour. RLU=relative light units.

The v1 sensor system was also tested for activation by target RNA T1. Experiments were run as described above, except that ligation time was increased from 5 to 15 minutes. Femtomolar detection of T1 RNA is shown in FIG. 6.

Example 10

Figure 7:
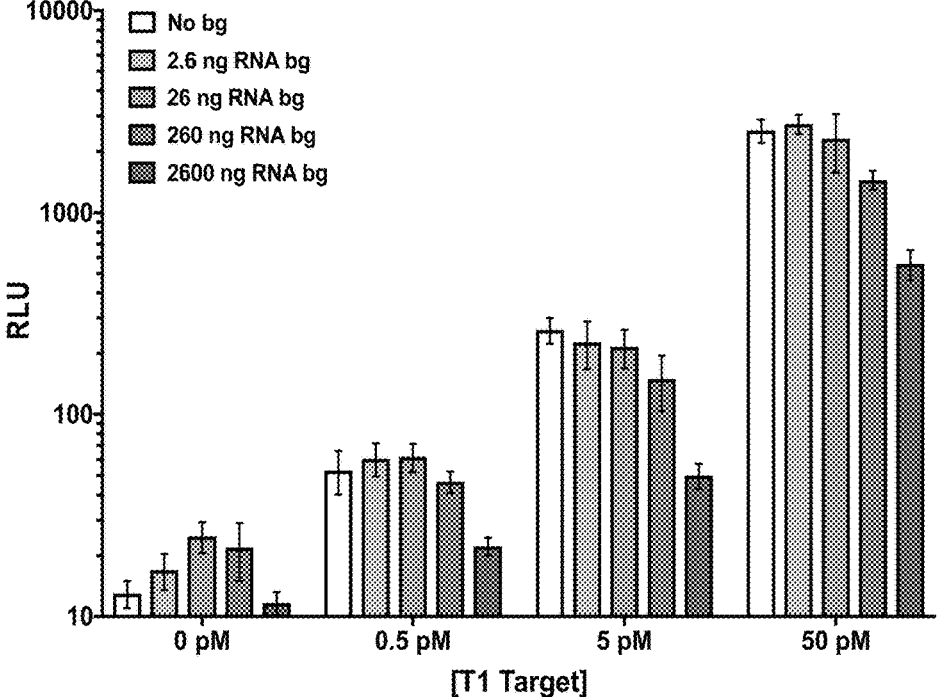
FIG. 7: Bar graph showing comparison of v1 sensor performance at several T1 target RNA concentrations (0 to 50 pM) with increasing amounts of background (bg) RNA, from 0 to 2600 ng. RLU=relative light units

High Specificity of v1 Sensor in Background of *E. coli* RNA and Whole Cell Extract v1 sensor performance was evaluated in the presence of increasing amounts of total *E. coli* RNA (ThermoFisher Scientific®) from 2.6-2600 ng. To accommodate the additional volume from the RNA background, the standard detection assay was modified by increasing the initial concentration of stock ssDNA sensor parts A and B by 7.5× to enable a lower volume of sensor to achieve the same final sensor concentration. This enabled addition of different volumes of background RNA without changing other reaction component concentrations. Detection of T1 RNA in varying backgrounds of non-specific *E. coli* RNA is shown in FIG. 7.

Figure 8:
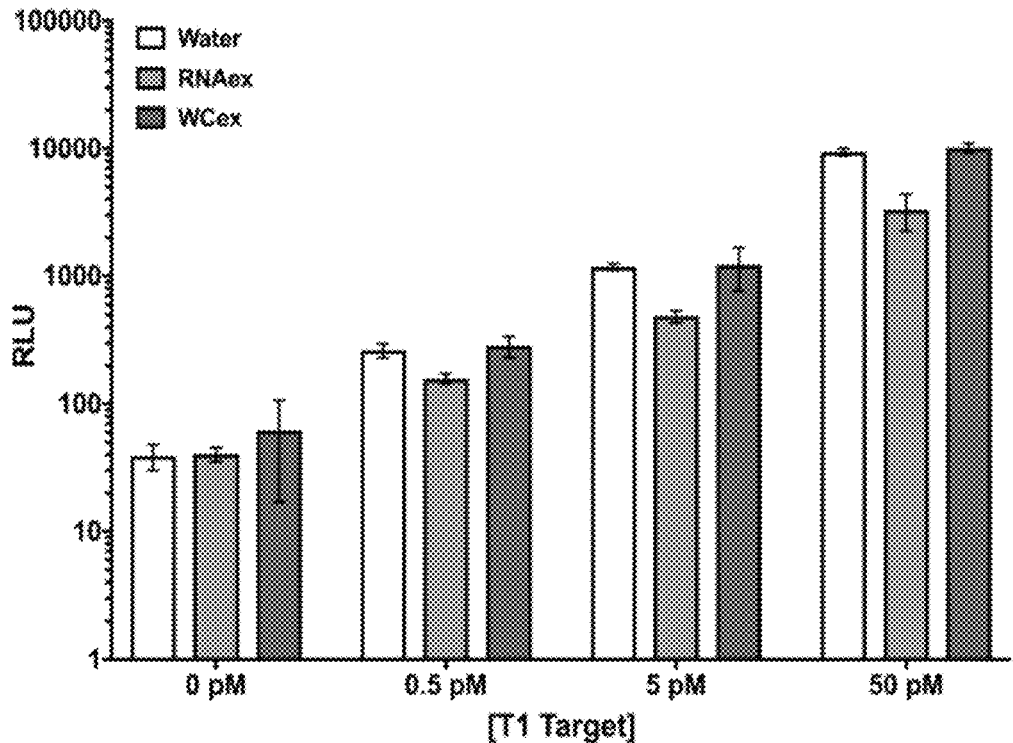
FIG. 8: Bar graph showing comparison of v1 sensor performance of T1 target spiked into backgrounds of water, RNA extract (RNAex), and heat-lysed whole cell extract (WCex). RLU=relative light units.

RNA obtained from *E. coli* by Trizol® extraction (RNAex) and crude whole cell extracts from comparable quantities ($4\times10^6$) of cells lysed by heating at 95° C. for 5 min (WCex) were also tested as background components with the v1 sensor system detecting target T1. Data are shown in FIG. 8.

Example 11

Detection of Target RNA Expressed in *E. coli*.

Figure 9:
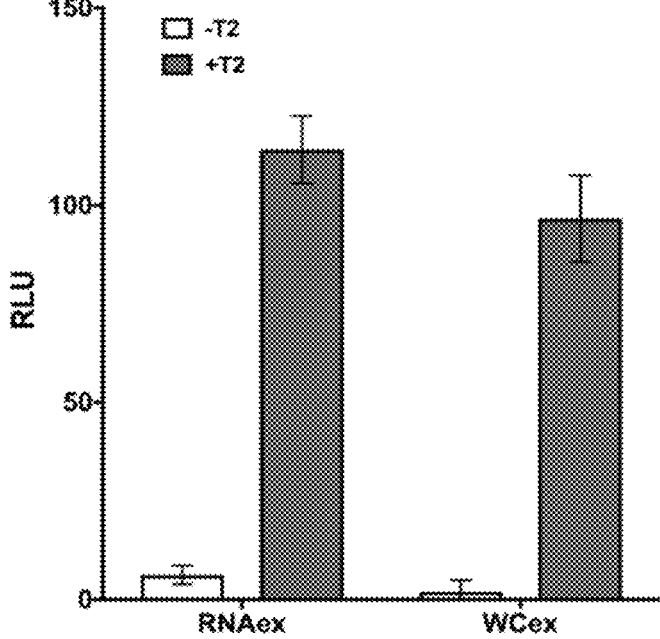
FIG. 9: Bar graph showing comparison of v1 sensor performance with T2 detection directly from RNA extract (RNAex) or heat-lysed whole cell extract (WCex) corresponding to equivalents of cell material. RLU=relative light units.

*E. coli* containing a plasmid expressing the T2 target was harvested and either lysed by heating to 95° C. for 5 min (WCex) or treated to RNA extraction by Trizol® (RNAex). The v1 sensor system was used to detect target RNA in both conditions with a 15-minute ligation and 1-hour expression incubation at room temperature, as shown in FIG. 9.

Example 12

Detection of Target RNA in Background of Human Saliva

Figure 10:
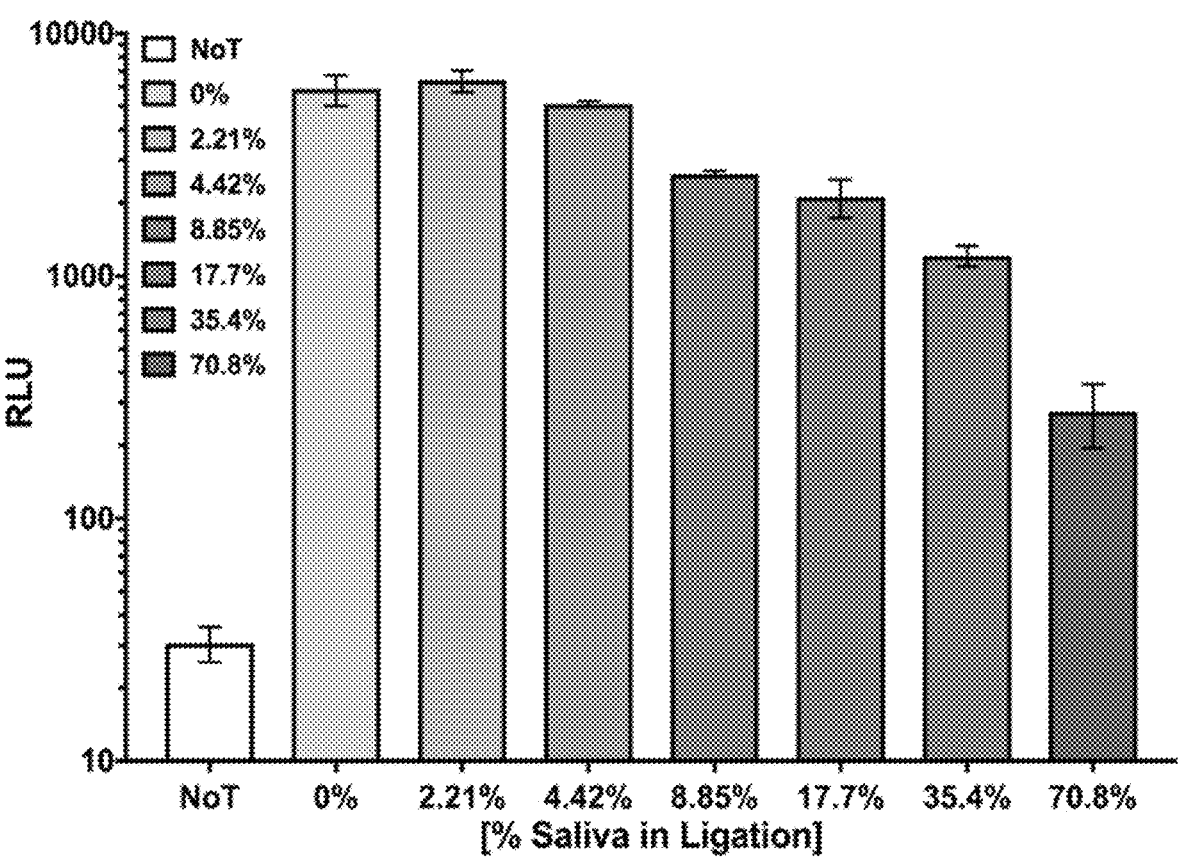
FIG. 10: Bar graph showing v1 sensor performance with T1 detection in increasing backgrounds of pooled human saliva (0 to 70.8%). RLU=relative light units.
Figure 11A:
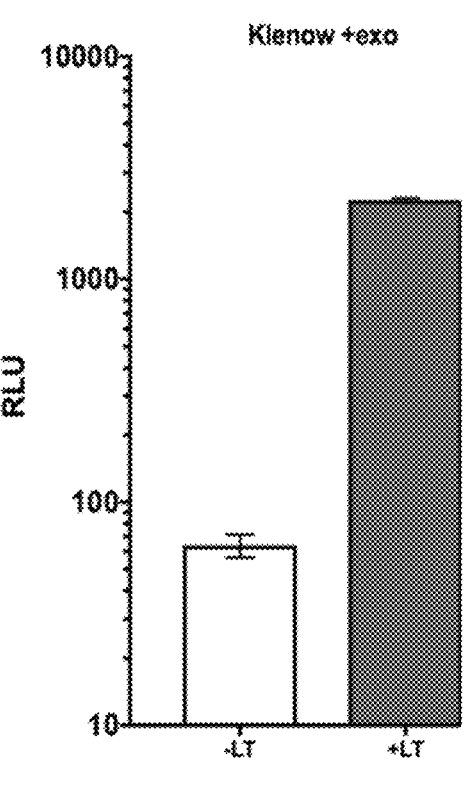
FIG. 11A-FIG. 11D: Bar graphs showing performance of different DNA polymerases in the process of RNA-mediated activation of version 3 sensor system.
Figure 11B:
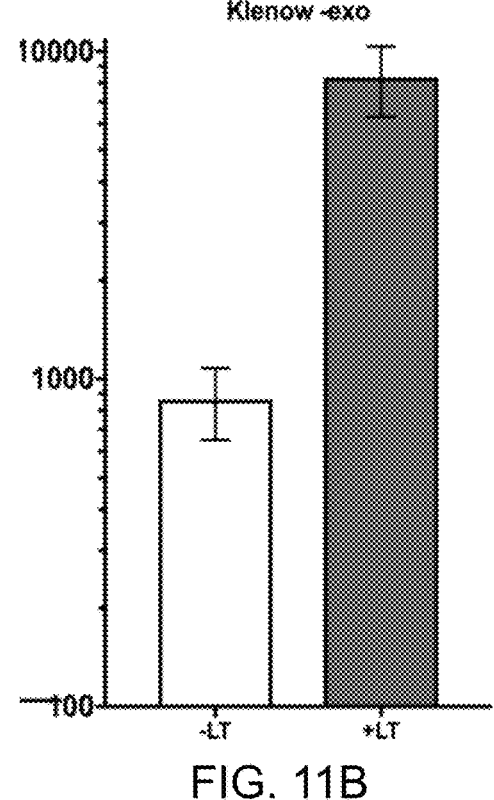
Figure 11C:
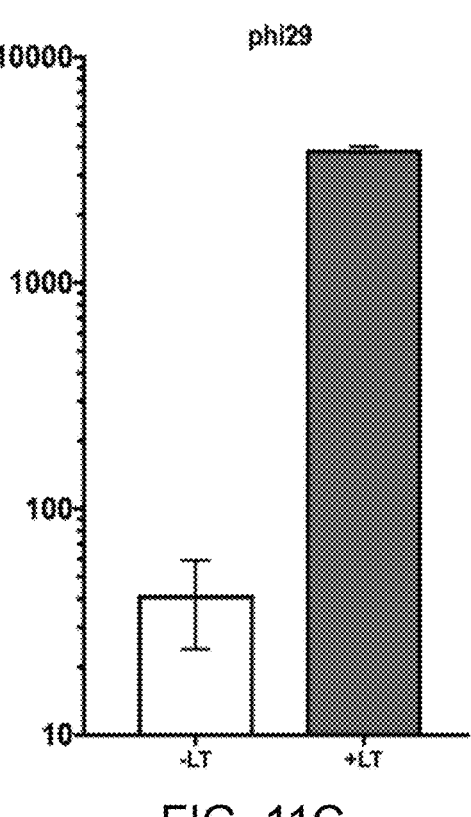
Figure 11D:
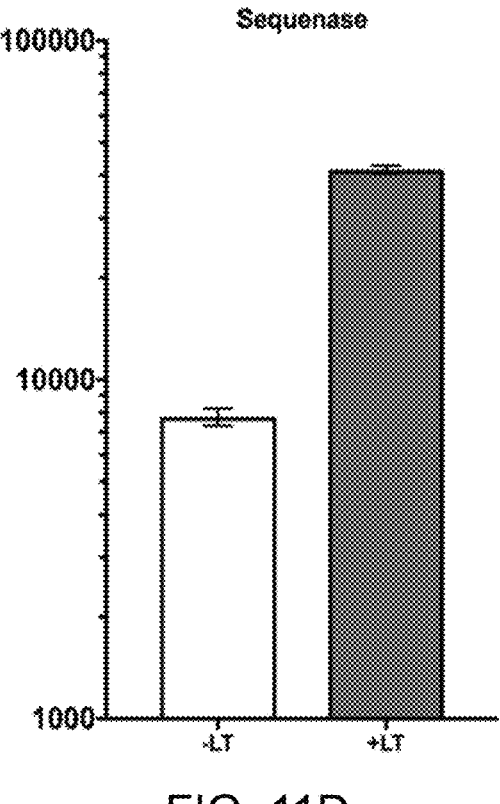

The v1 sensor system was used to detect a fixed concentration (50 pM) of T1 target RNA in increasing concentrations (v/v) of pooled human saliva (Innovative Research Inc.®, Novi, MI). Data are shown in FIG. 10.

Example 13

Performance of Alternative DNA Polymerases.

The v3 sensor system (see e.g., FIG. 3) was tested for performance using different DNA polymerases for the coding strand extension step. DNA polymerase processivity, exonuclease activity, and promiscuity may all have an impact on performance. Parts A and B components were added at 12.5 nM each and were incubated with 8.6 nM target RNA. After a five-minute incubation at ambient temperature (24-26° C.), the ligation reaction was added to a cell-free expression system (PurExpress®, NEB®) supplemented with 125 nM reverse DNA primer and one of the following DNA polymerases (0.15 U each): Klenow fragment +exo; Klenow fragment −exo; phi29 polymerase; or Sequenase™ Reactions were further incubated at ambient temperature for one hour. Performance with Target 2 is shown in FIG. 11A-FIG. 11D.

Example 14

Performance of Alternative Sensor Component Schemes.

Figure 2B:
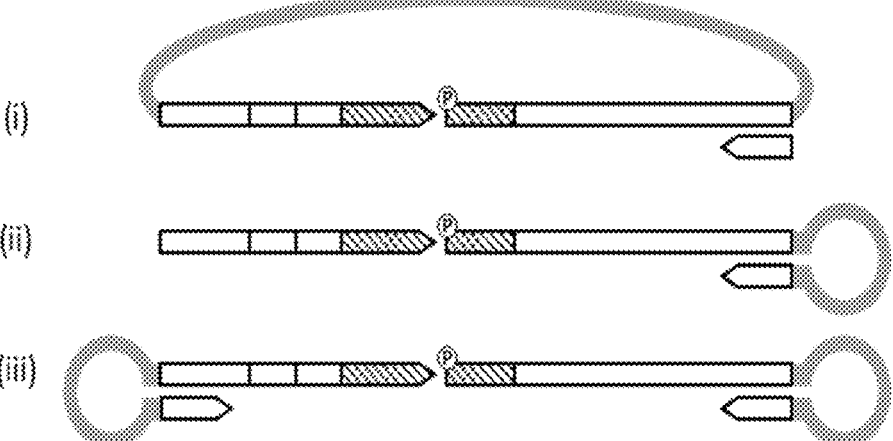
Figure 12:
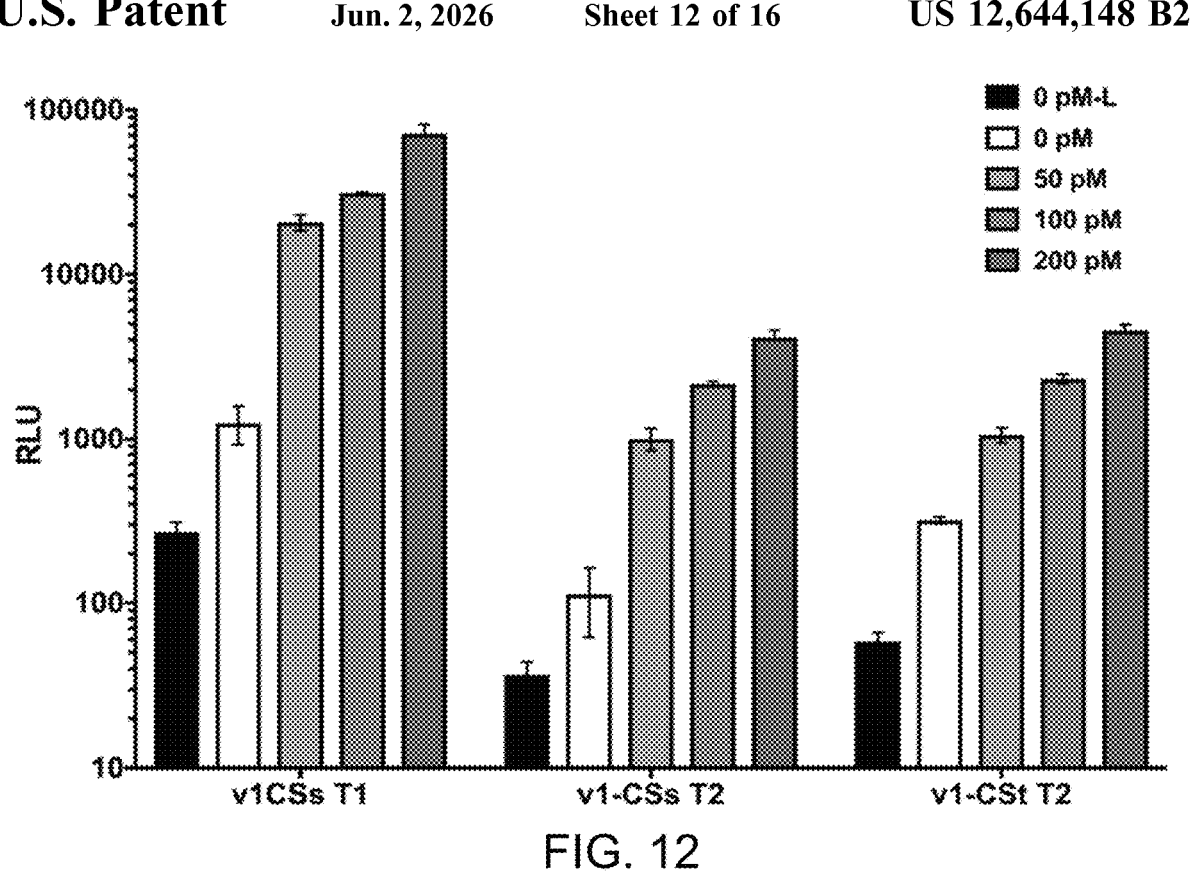
FIG. 12: Bar graph showing testing of alternative sensor component scheme of v1 where both A and B parts are on the same ssDNA sequence such that B is now 5' of A. Two constructs were tested, one terminating the RNA transcript with the use of a T7 terminator domain (CSt) and the other containing three repeat stop codons (CSs). The bar graph shows comparison of performance with detection of T1 or T2 target RNA at varying concentrations (0 to 200 pM). RLU=relative light units.

The alternative sensor component scheme of v1 illustrated in FIG. 2B(i) was created where both A and B parts are on the same ssDNA sequence such that B is now 5' of A. Two constructs were tested, one terminating the RNA transcript with the use of a T7 terminator domain (CSt) and the other containing three repeat stop codons (CSs). Data showing performance of these alternative schemes are shown in FIG. 12.

TABLE 1

Nucleic Acid Sequences. Listed are parts A and B for
each sensor design. Full-length (AB) controls are the
combination of both A and B parts. Lowercase letters
indicate inserted spacer domains.

| Name | SEQ ID NO: | Sequence |
|------|------------|----------|
| v1_A_T1 | 1 | GAATTAATACGACTCACTATAGGGATCTATCCACTACTCCTAAGGAG ACTTTTTATGAATTATCTATGCATTACT |
| V1_B_T1 | 2 | AACCCTTCCGCCACTAAAGTGTTCACATTGGAGGACTTTGTAGGGGA CTGGCGCCAGACAGCGGGCTACAACCTTGATCAGGTTCTGGAGCAG GGAGGTGTAAGTTCACTTTTCCAGAATTTGGGTGTGAGTGTCACCCC GATCCAACGTATCGTGCTTTCCGGAGAAAATGGGCTGAAGATCGAC ATCCATGTTATTATTCCTTATGAAGGGCTTAGCGGAGATCAAATGGG CCAAATCGAAAAGATTTTCAAAGTGGTATATCCTGTTGACGACCATC ATTTTAAGGTCATTCTGCATTACGGAACTTTAGTCATCGACGGCGTC ACACCTAACATGATTGACTATTTTGGCCGTCCGTATGAGGGCATCGC AGTGTTTGACGGAAAAAAAATCACCGTGACAGGGACACTGTGGAAC GGCAATAAGATTATCGACGAGCGCCTTATTAACCCAGATGGGTCGC TTTTATTCCGTGTCACTATTAATGGTGTCACTGGCTGGCGTTTGTGCG AACGCATCCTGGCATAA |
| v1_A_T2 | 3 | GAATTAATACGACTCACTATAGGGGTCCTCCCCCCCAAAACTACAAT AAGGGGGTTTTTTATGTCCATTCCTGGCTTTAAT |
| v1_A2_T2 | 4 | GAATTAATACGACTCACTATAGGGATCTATCCACTACTCCTAAGGAG ACTTTTTATGTCCATTCCTGGCTTTAAT |
| v1_B_T2 | 5 | TTTACTGGTACAGTTTCAGTGTTCACATTGGAGGACTTTGTAGGGGA CTGGCGCCAGACAGCGGGCTACAACCTTGATCAGGTTCTGGAGCAG GGAGGTGTAAGTTCACTTTTCCAGAATTTGGGTGTGAGTGTCACCCC GATCCAACGTATCGTGCTTTCCGGAGAAAATGGGCTGAAGATCGAC ATCCATGTTATTATTCCTTATGAAGGGCTTAGCGGAGATCAAATGGG CCAAATCGAAAAGATTTTCAAAGTGGTATATCCTGTTGACGACCATC ATTTTAAGGTCATTCTGCATTACGGAACTTTAGTCATCGACGGCGTC ACACCTAACATGATTGACTATTTTGGCCGTCCGTATGAGGGCATCGC AGTGTTTGACGGAAAAAAAATCACCGTGACAGGGACACTGTGGAAC GGCAATAAGATTATCGACGAGCGCCTTATTAACCCAGATGGGTCGC TTTTATTCCGTGTCACTATTAATGGTGTCACTGGCTGGCGTTTGTGCG AACGCATCCTGGCATAA |
| v1_CSs_T1 | 6 | AACCCTTCCGCCACTAAAGTGTTCACATTGGAGGACTTTGTAGGGGA CTGGCGCCAGACAGCGGGCTACAACCTTGATCAGGTTCTGGAGCAG |

TABLE 1-continued

Nucleic Acid Sequences. Listed are parts A and B for
each sensor design. Full-length (AB) controls are the
combination of both A and B parts. Lowercase letters
indicate inserted spacer domains.

| Name | SEQ ID NO: | Sequence |
|------|------------|----------|
| | | GGAGGTGTAAGTTCACTTTTCCAGAATTTGGGTGTGAGTGTCACCCC GATCCAACGTATCGTGCTTTCCGGAGAAATGGGCTGAAGATCGAC ATCCATGTTATTATTCCTTATGAAGGGCTTAGCGGAGATCAAATGGG CCAAATCGAAAAGATTTTCAAAGTGGTATATCCTGTTGACGACCATC ATTTTAAGGTCATTCTGCATTACGGAACTTTAGTCATCGACGGCGTC ACACCTAACATGATTGACTATTTTGGCCGTCCGTATGAGGGCATCGC AGTGTTTGACGGAAAAAAAATCACCGTGACAGGGACACTGTGGAAC GGCAATAAGATTATCGACGAGCGCCTTATTAACCCAGATGGGTCGC TTTTATTCCGTGTCACTATTAATGGTGTCACTGGCTGGCGTTTGTGCG AACGCATCCTGGCATAATAATAAGAATTAATACGACTCACTATAGG GATCTATCCACTACTCCTAAGGAGACTTTTTATGAATTATCTATGCA TTACT |
| v1_CSt_T2 | 7 | TTTACTGGTACAGTTTCAGTGTTCACATTGGAGGACTTTGTAGGGGA CTGGCGCCAGACAGCGGGCTACAACCTTGATCAGGTTCTGGAGCAG GGAGGTGTAAGTTCACTTTTCCAGAATTTGGGTGTGAGTGTCACCCC GATCCAACGTATCGTGCTTTCCGGAGAAATGGGCTGAAGATCGAC ATCCATGTTATTATTCCTTATGAAGGGCTTAGCGGAGATCAAATGGG CCAAATCGAAAAGATTTTCAAAGTGGTATATCCTGTTGACGACCATC ATTTTAAGGTCATTCTGCATTACGGAACTTTAGTCATCGACGGCGTC ACACCTAACATGATTGACTATTTTGGCCGTCCGTATGAGGGCATCGC AGTGTTTGACGGAAAAAAAATCACCGTGACAGGGACACTGTGGAAC GGCAATAAGATTATCGACGAGCGCCTTATTAACCCAGATGGGTCGC TTTTATTCCGTGTCACTATTAATGGTGTCACTGGCTGGCGTTTGTGCG AACGCATCCTGGCATAACTAGCATAACCCCTCTCTAAACGGAGGGG TTTGAATTAATACGACTCACTATAGGGGTCCTCCCCCCCAAAACTAC AATAAGGGGGTTTTTTATGTCCATTCCTGGCTTTAAT |
| v1_CSs_T2 | 8 | TTTACTGGTACAGTTTCAGTGTTCACATTGGAGGACTTTGTAGGGGA CTGGCGCCAGACAGCGGGCTACAACCTTGATCAGGTTCTGGAGCAG GGAGGTGTAAGTTCACTTTTCCAGAATTTGGGTGTGAGTGTCACCCC GATCCAACGTATCGTGCTTTCCGGAGAAATGGGCTGAAGATCGAC ATCCATGTTATTATTCCTTATGAAGGGCTTAGCGGAGATCAAATGGG CCAAATCGAAAAGATTTTCAAAGTGGTATATCCTGTTGACGACCATC ATTTTAAGGTCATTCTGCATTACGGAACTTTAGTCATCGACGGCGTC ACACCTAACATGATTGACTATTTTGGCCGTCCGTATGAGGGCATCGC AGTGTTTGACGGAAAAAAAATCACCGTGACAGGGACACTGTGGAAC GGCAATAAGATTATCGACGAGCGCCTTATTAACCCAGATGGGTCGC TTTTATTCCGTGTCACTATTAATGGTGTCACTGGCTGGCGTTTGTGCG AACGCATCCTGGCATAATGATAATAGTTTGGTTTGAATTAATACGAC TCACTATAGGGGTCCTCCCCCCCAAAACTACAATAAGGGGGTTTTTT ATGTCCATTCCTGGCTTTAAT |
| v2_A_T1 | 9 | GAATTAATACGACTCACTATAGGAATTATCTATGCATTACT |
| v2_B_T1 | 10 | AACCCTTCCGCCACTAAAGGGTCAATTAAGGAGGTATATATGGTGTT CACATTGGAGGACTTTGTAGGGGACTGGCGCCAGACAGCGGGCTAC AACCTTGATCAGGTTCTGGAGCAGGGAGGTGTAAGTTCACTTTTCCA GAATTTGGGTGTGAGTGTCACCCCGATCCAACGTATCGTGCTTTCCG GAGAAATGGGCTGAAGATCGACATCCATGTTATTATTCCTTATGAA GGGCTTAGCGGAGATCAAATGGGCCAAATCGAAAAGATTTTCAAAG TGGTATATCCTGTTGACGACCATCATTTTAAGGTCATTCTGCATTAC GGAACTTTAGTCATCGACGCGTCACACCTAACATGATTGACTATTT TGGCCGTCCGTATGAGGGCATCGCAGTGTTTGACGGAAAAAAAATC ACCGTGACAGGGACACTGTGGAACGGCAATAAGATTATCGACGAGC GCCTTATTAACCCAGATGGGTCGCTTTTATTCCGTGTCACTATTAATG GTGTCACTGGCTGGCGTTTGTGCGAACGCATCCTGGCATAA |
| v2_A_T2 | 11 | GAATTAATACGACTCACTATAGGTCCATTCCTGGCTTTAAT |
| v2_B_T2 | 12 | TTTACTGGTACAGTTTCAAAACTGTAAGCCCGTAGAAAGGACTTTCA AACAATAAGCGGGTAAGGAGGTATTAAATGGTGTTCACATTGGAGG ACTTTGTAGGGGACTGGCGCCAGACAGCGGGCTACAACCTTGATCA GGTTCTGGAGCAGGGAGGTGTAAGTTCACTTTTCCAGAATTTGGGTG TGAGTGTCACCCCGATCCAACGTATCGTGCTTTCCGGAGAAATGGG CTGAAGATCGACATCCATGTTATTATTCCTTATGAAGGGCTTAGCGG AGATCAAATGGGCCAAATCGAAAAGATTTTCAAAGTGGTATATCCT GTTGACGACCATCATTTTAAGGTCATTCTGCATTACGGAACTTTAGT |

TABLE 1-continued

Nucleic Acid Sequences. Listed are parts A and B for
each sensor design. Full-length (AB) controls are the
combination of both A and B parts. Lowercase letters
indicate inserted spacer domains.

| Name | SEQ ID NO: | Sequence |
|------|------------|----------|
| | | CATCGACGGCGTCACACCTAACATGATTGACTATTTTGGCCGTCCGT ATGAGGGCATCGCAGTGTTTGACGGAAAAAAAATCACCGTGACAGG GACACTGTGGAACGGCAATAAGATTATCGACGAGCGCCTTATTAAC CCAGATGGGTCGCTTTTATTCCGTGTCACTATTAATGGTGTCACTGG CTGGCGTTTGTGCGAACGCATCCTGGCATAA |
| v3_A_T1 | 13 | GAATTAATACGACTCACTATAGGTGAGTATATAGGTAGAAGAGGTA TTGGAGGTATTGATGGTGTTCACATTGGAGGACTTTGTAGGGGACTG GCGCCAGACAGCGGGCTACAACCTTGATCAGGTTCTGGAGCAGGGA GGTGTAAGTTCACTTTTCCAGAATTTGGGTGTGAGTGTCACCC CGAT CCAACGTATCGTGCTTTCCGGAGAAAATGGGCTGAAGATCGACATC CATGTTATTATTCCTTATGAAGGGCTTAGCGGAGATCAAATGGGCCA AATCGAAAGATTTTCAAAGTGGTATATCCTGTTGACGACCATCATT TTAAGGTCATTCTGCATTACGGAACTTTAGTCATCGACGGCggtggc gggAATTATCTATGCATTACT |
| v3_B_T1 | 14 | AACCCTTCCGCCACTAAAggcggtgggGTCACACCTAACATGATTGA CTATTTTGGCCGTCCGTATGAGGGCATCGCAGTGTTTGACGGAAAAA AAATCACCGTGACAGGGACACTGTGGAACGGCAATAAGATTATCGAC GAGCGCCTTATTAACCCAGATGGGTCGCTTTTATTCCGTGTCACTAT TAATGGTGTCACTGGCTGGCGTTTGTGCGAACGCATCCTGGCATAA |
| v3_A_T2 | 15 | GAATTAATACGACTCACTATAGGTGAGTATATAGGTAGAAGAGGTA TTGGAGGTATTGATGGTGTTCACATTGGAGGACTTTGTAGGGGACTG GCGCCAGACAGCGGGCTACAACCTTGATCAGGTTCTGGAGCAGGGA GGTGTAAGTTCACTTTTCCAGAATTTGGGTGTGAGTGTCACCCCGAT CCAACGTATCGTGCTTTCCGGAGAAAATGGGCTGAAGATCGACATC CATGTTATTATTCCTTATGAAGGGCTTAGCGGAGATCAAATGGGCCA AATCGAAAGATTTTCAAAGTGGTATATCCTGTTGACGACCATCATT TTAAGGTCATTCTGCATTACGGAACTTTAGTCATCGACGGCGGTGGC GGGTCCATTCCTGGCTTTAAT |
| v3_B_T2 | 16 | TTTACTGGTACAGTTTCAGGCGGTGGGGTCACACCTAACATGATTGA CTATTTTGGCCGTCCGTATGAGGGCATCGCAGTGTTTGACGGAAAAA AAATCACCGTGACAGGGACACTGTGGAACGGCAATAAGATTATCGA CGAGCGCCTTATTAACCCAGATGGGTCGCTTTTATTCCGTGTCACTA TTAATGGTGTCACTGGCTGGCGTTTGTGCGAACGCATCCTGGCATAA |
| v3_A_T3 | 17 | GAATTAATACGACTCACTATAGGTGAGTATATAGGTAGAAGAGGTA TTGGAGGTATTGATGGTGTTCACATTGGAGGACTTTGTAGGGGACTG GCGCCAGACAGCGGGCTACAACCTTGATCAGGTTCTGGAGCAGGGA GGTGTAAGTTCACTTTTCCAGAATTTGGGTGTGAGTGTCACCCCGAT CCAACGTATCGTGCTTTCCGGAGAAAATGGGCTGAAGATCGACATC CATGTTATTATTCCTTATGAAGGGCTTAGCGGAGATCAAATGGGCCA AATCGAAAGATTTTCAAAGTGGTATATCCTGTTGACGACCATCATT TTAAGGTCATTCTGCATTACGGAACTTTAGTCATCGACGGC |
| v3_B_T3 | 18 | GTCACACCTAACATGATTGACTATTTTGGCCGTCCGTATGAGGGCAT CGCAGTGTTTGACGGAAAAAAAATCACCGTGACAGGGACACTGTGG AACGGCAATAAGATTATCGACGAGCGCCTTATTAACCCAGATGGGT CGCTTTTATTCCGTGTCACTATTAATGGTGTCACTGGCTGGCGTTTGT GCGAACGCATCCTGGCATAA |
| Rev primer | 19 | TTATGCCAGGATGCGTTCGC |
| T1 | 20 | TTTAGTGGCGGAAGGGTTAGTAATGCATAGATAATT |
| T2 | 21 | TGAAACTGTACCAGTAAAATTAAAGCCAGGAATGGA |
| T3 | 22 | AATCATGTTAGGTGTGACGCCGTCGATGACTAAAGT |

Example 15

Discrimination of Single Nucleotide Variations (SNVs).

Signal nucleotide polymorphisms or single nucleotide variations can be detected using the methods and compositions described herein by positioning the location of the SNP or SNV at one of the two bases at the junction of the hybridization region, on either the upstream or downstream 4891-5430-1425.1 88 ssDNA sensor domain. In some embodiments of any of the aspects, one or more mismatched bases may be additionally introduced within the hybridization region.

Four different exemplary variants were tested using v1. The target sequence and tested variants representing SNPs or SNVs are listed in Table 2 below. Base changes reflecting SNVs are bolded.

TABLE 2

Nucleic Acid Sequences. RNA variants with single nucleotide variations (SNVs).

| RNA variants | SEQ ID NO: | Sequence |
|---|---|---|
| Target (UA) | 23 | UUUAGUGGCGGAAGGGUUAGUAAUGCAUAGAUAAUU |
| SNP-UG | 24 | UUUAGUGGCGGAAGGGUUGGUAAUGCAUAGAUAAUU |
| SNP-AA | 25 | UUUAGUGGCGGAAGGGUAAGUAAUGCAUAGAUAAUU |
| SNP-GA | 26 | UUUAGUGGCGGAAGGGUGAGUAAUGCAUAGAUAAUU |
| SNP-GG | 27 | UUUAGUGGCGGAAGGGUGGGUAAUGCAUAGAUAAUU |

Figure 13:
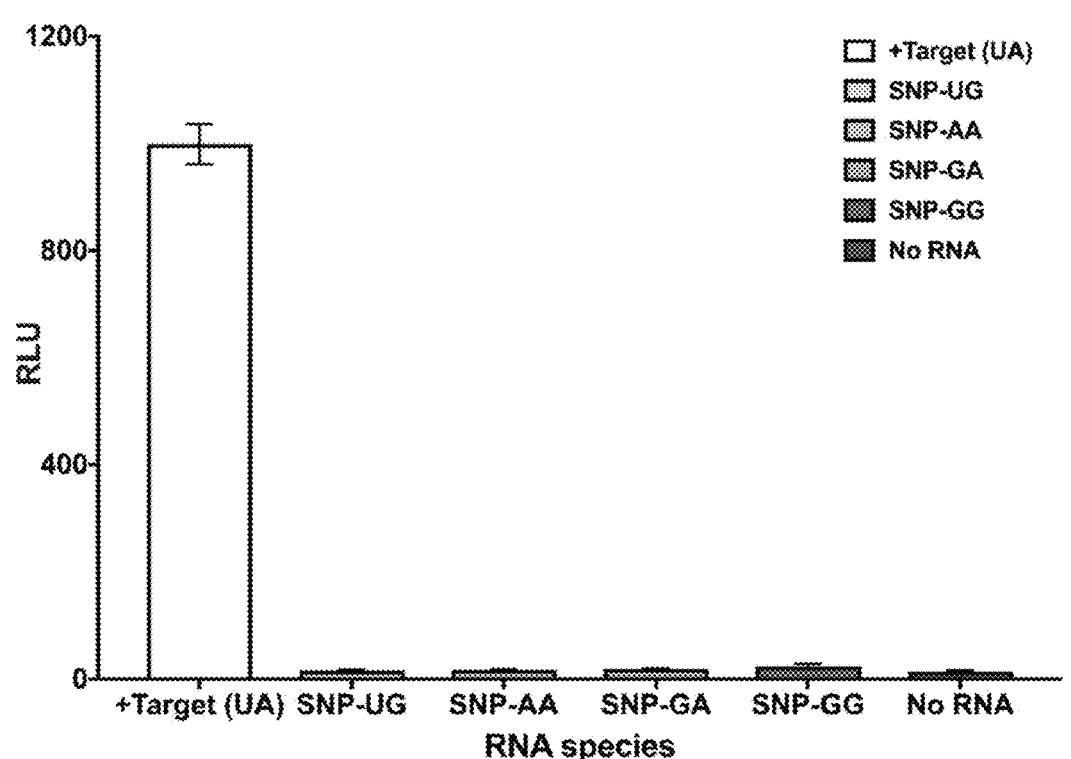
FIG. 13: Bar graph showing discrimination of single nucleotide variations (SNVs) or single nucleotide polymorphisms (SNPs) introduced within the hybridization region of the target of v1. Four different variants were tested (e.g., SNP-UG, SNP-AA, SNP-GA, SNP-GG). RLU=relative light units.

Single stranded RNA sequences listed above were detected with a sensor as described in Example 6. As shown in FIG. 13, differential response is observed based on the presence of a non-matching nucleotide at one or both ends of the hybridization region junction.

Example 16

Performance of Alternative DNA Polymerases.

Multiple DNA polymerases were tested using v1, for function with the method as described in Examples 6 and 13. Additional polymerases and polymerase formulations listed below were also tested: IsoPol (polymerase from *Psychrobacillus*): 4 units per reaction; IsoPol SD⁺ (polymerase from *Psychrobacillus* with enhanced strand displacement): 4 units per reaction (with additional examples using fewer units of enzyme shown); or Bsu (polymerase from *B. subtilis*): 4 units per reaction.

Figure 14A:
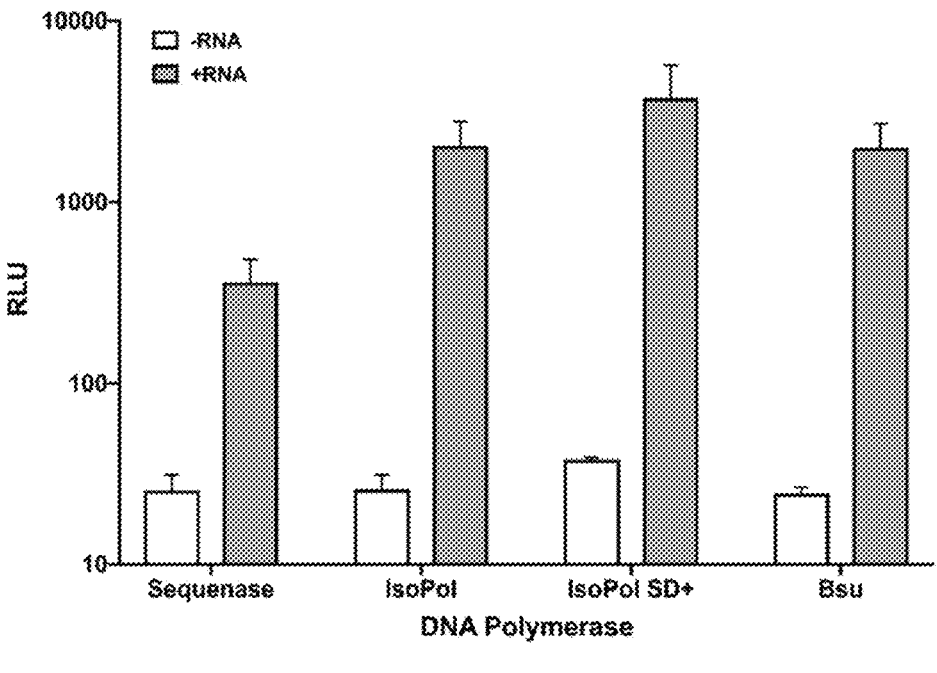
FIG. 14A-FIG. 14C: Bar graphs showing testing of multiple DNA polymerases using v1.
Figure 14B:
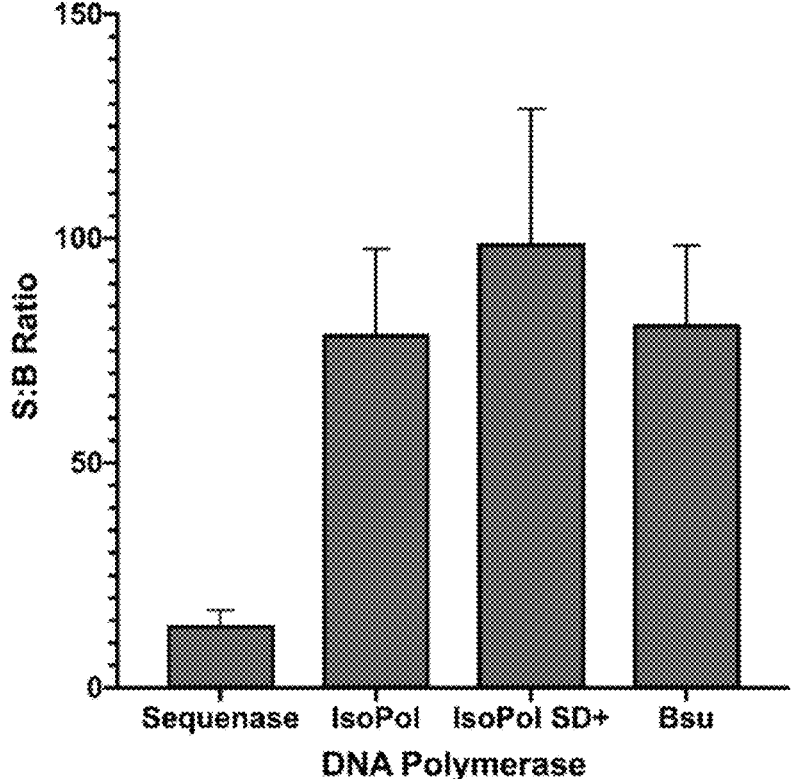

Performance of these polymerases was tested in the in vitro detection system targeting the CT target RNA sequence (+RNA) versus a negative control without the target RNA sequence (−RNA) (see e.g., FIG. 14A). Signal to background ratio based on these measurements (S:B ratio) was also tested for each polymerase (see e.g., FIG. 14B).

Figure 14C:
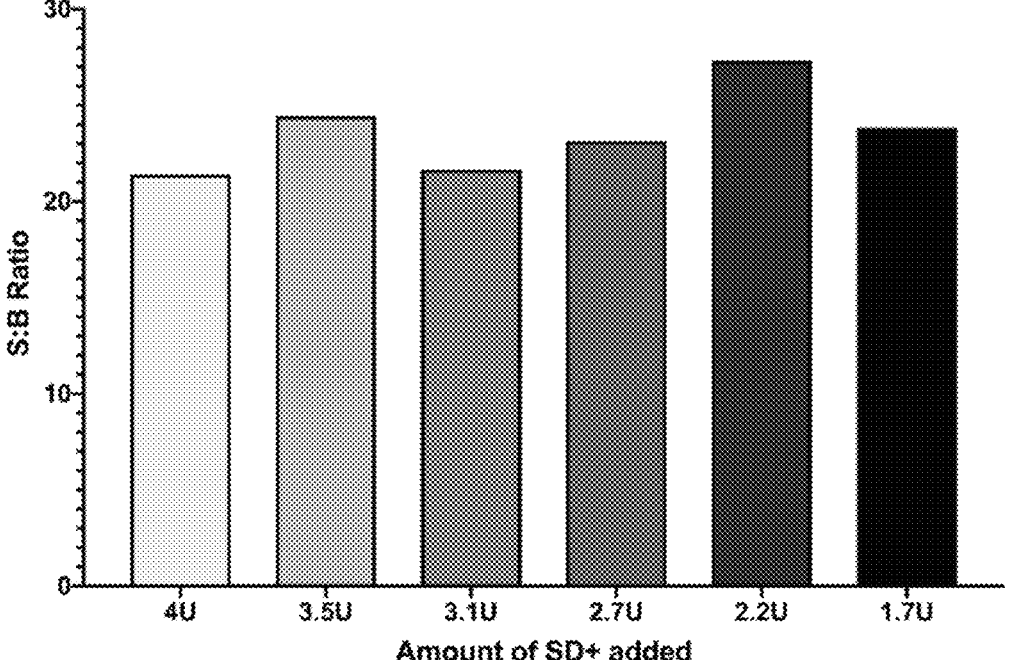

Additionally, different amounts of units of IsoPol SD+ were tested with the detection method (see e.g., FIG. 14C). Effective detection was achieved with as few as 1.7 units of enzyme.

Example 17

Demonstration of Multiple Ways to Separate an Expression Cassette Within a Coding Sequence to Design ssDNA Sensor Parts.

Three exemplary locations are described herein for splitting an expression cassette and insertion of the target hybridization sequence (see e.g., FIG. 3 Version 3). One skilled in the art would understand that solvent exposed loops of any reporter or other protein would be suitable locations for insertion of additional amino acids (e.g., as resulting from insertion of a hybridization region in the DNA sequence). Herein is demonstrated the ability to split the expression cassette at multiple solvent exposed loop sites to create a functional nucleic acid sensing system from the resulting ssDNA sensor parts. The expression cassette includes a gene coding for a nanoluciferase enzyme (NLuc). Solvent exposed loop regions (Loops 1-5) within the Nluc that were tested are indicated in Table 3. The amino acid single letter abbreviations and number within the polypeptide sequence at either end of the split/insertion site are given. For example, E50-N51 indicates insertion of the hybridization sequence in the coding sequence between codons coding for glutamate at amino acid position 50 and asparagine at amino acid position 51.

TABLE 3

Location of solvent exposed loop regions (Loops 1-5) within the Nluc

| Insertion Site | NLuc Location |
|---|---|
| Loop1 | E50-N51 |
| Loop2 | L66-S67 |
| Loop3 | G123-K124 |
| Loop4 | G135-N136 |
| Loop5 | N145-P146 |

Figure 15A:
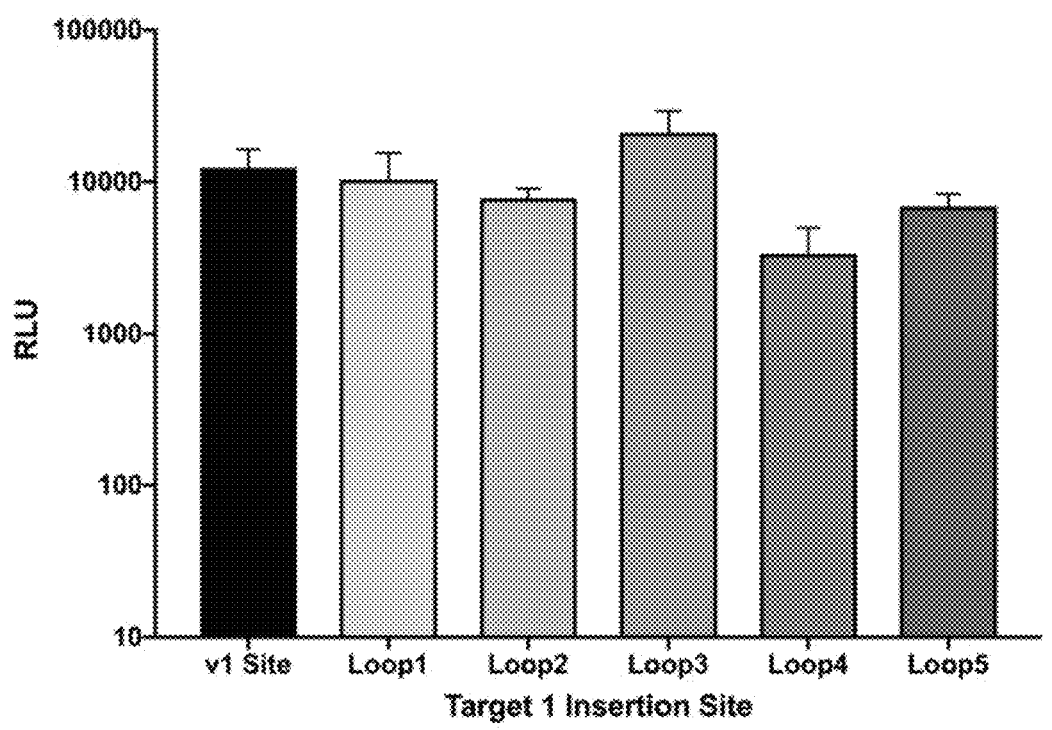
FIG. 15A-FIG. 15B: Bar graphs showing testing of splitting the expression cassette of nanoluciferase enzyme (NLuc) and insertion of the target hybridization sequence into solvent exposed loops.

As shown in FIG. 15A, activity was tested for the Nluc with the hybridization sequence inserted at the solvent exposed loop regions indicated. Additional amino acids within the Nluc resulting from insertion of the hybridization sequence did not substantially impact luciferase function.

Figure 15B:
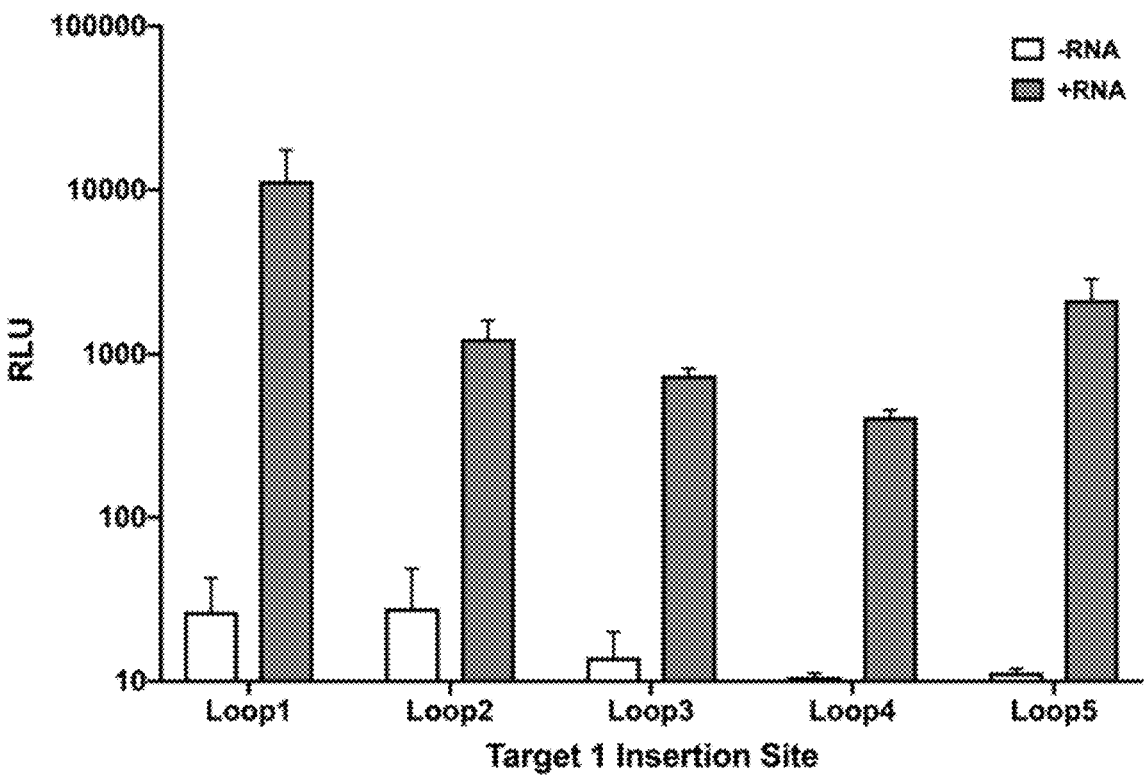

Additionally, ssDNA sensor parts were constructed based on these split locations and target CT sequence as described, and these were tested for detection of 100 nM target CT RNA. All expression cassette spit locations were able to effectively detect target RNA (see e.g., FIG. 15B).

Example 18

Split Nanoluciferase Constructs.

To identify A & B parts that have a lower background in the assay, split sites were chosen in the middle of the luciferase coding sequence (see e.g., FIG. 3 Version 3). By moving the split site into the luciferase coding sequence, the background signal from spurious transcription and translation of individual parts will yield only non-functional fragments of the luciferase protein.

Fourteen different regions of the luciferase protein were identified that could be amenable to harbor an insertion. Fourteen different split sites within these regions (see e.g., SEQ ID NO: 28 and Table 4) were tested to identify split sites that have low background enzymatic signal if the two pieces are expressed in an in vitro cell free expression system in the absence of successful ligation. These sites are located in the known loops of the nano-luciferase protein. A & B parts were built with transcription and translation driven by a T7 promotor, an optimal RBS site and an ATG start codon (see e.g., FIG. 16).

SEQ ID NO: 28 is the sequence of luciferase used in these studies, not including the initiation codon.

```
                                    (SEQ ID NO: 28)
VFTLRDFVGDWRQTAGYNLDQVLEQGGVSSLFQNLGVSVTPIQRIVLSG

ENGLKIDIEVIIPYEGLSGDQMGQIEKIFKVVYPVDDHHFKVILHYGTL

VIDGVTPNMIDYFGRPYEGIAVFDGKKITVTGTLWNGNKIIDERLINPD

GSLLFRVTINGVTGWRLCERILA
```

TABLE 4

List of split sites tested in SEQ ID NO: 28

| Split Site | Region | Split Location |
|---|---|---|
| 1 | G16-L19 | Y17-N18 |
| 2 | Q25-L32 | G26-G27 |

TABLE 4-continued

List of split sites tested in SEQ ID NO: 28

| Split Site | Region | Split Location |
|---|---|---|
| 3 | Q25-L31 | S29-S30 |
| 4 | L35-I42 | G36-G37 |
| 5 | L47-L53 | E50-N51 |
| 6 | P62-G68 | L66-S67 |
| 7 | F78-P83 | K79-V80 |
| 8 | V84-F89 | D86-H87 |
| 9 | L98-N106 | D101-G102 |
| 10 | D109-Y115 | R113-P114 |
| 11 | V120-K125 | G123-K124 |
| 12 | T131-K137 | G135-N136 |
| 13 | L141-L150 | N145-P146 |
| 14 | I156-V159 | N157-G148 |

Figures 16, 17:
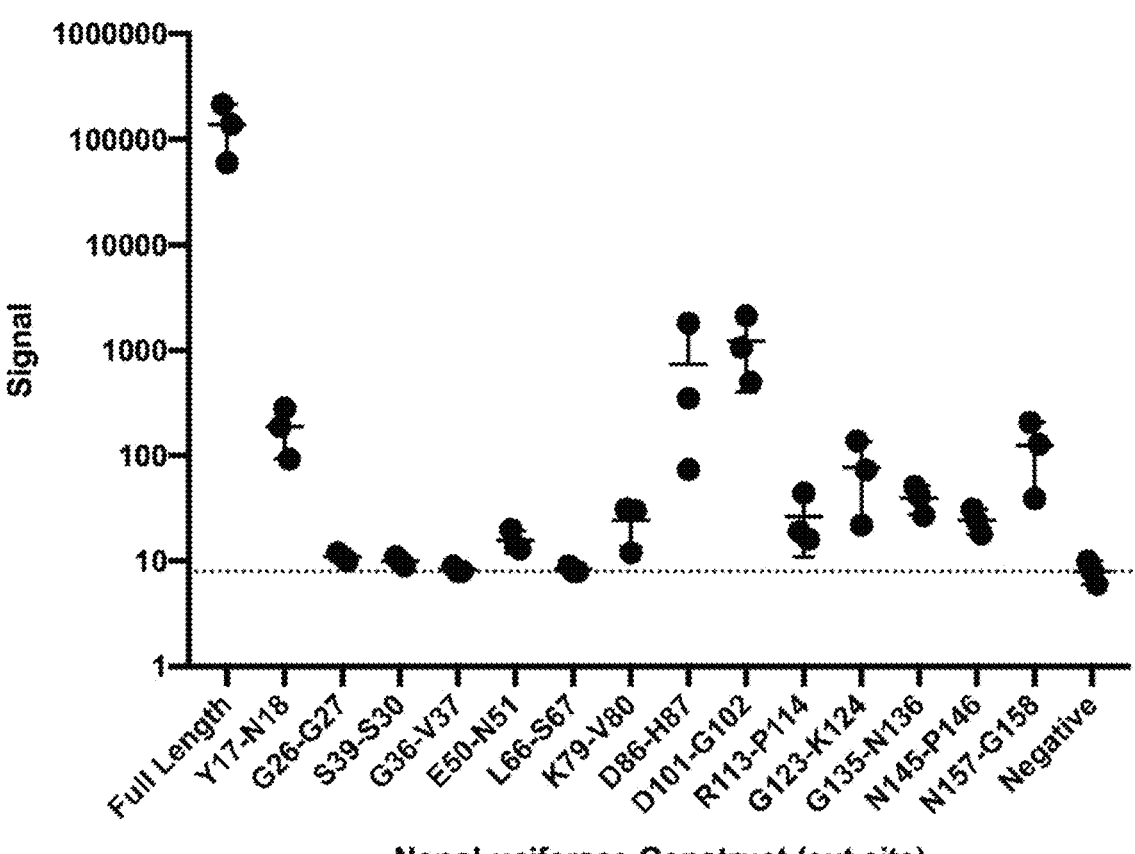
FIG. 16: Schematic of the constructs used to test background from independent transcription/translation of split luciferase constructs. Each PCR product has a T7 promotor followed by an RBS and ATG start codon, the fragment of Nanoluciferase and a stop codon. For example, for split site 1, part A would be a DNA sequence encoding amino acids 1-17 from sequence 1 and part B would be a DNA sequence encoding amino acids 18-170.
FIG. 17: Bar graph showing Luminescence signal of split luciferase constructs tested in a cell free expression system.

Split sites 2, 3, 4, 5, 6, 7, 10, 11, 12, 13 were the sites in NanoLuciferase with the lowest luminescence signal (see e.g., FIG. 17) when tested as split constructs with A and B parts (see e.g., FIG. 16).

To identify split sites that would yield a functional full length luciferase gene after a successful ligation step, PCR constructs were generated with a T7 promotor, RBS, start codon and full length luciferase gene with a trigger sequence. The trigger sequence was inserted into the split sites with the lowest background signal when the two parts were expressed separately (see e.g., FIG. 17).

The sites with the lower background (2, 3, 4, 5, 6, 7, 10, 11, 12, 13) were tested with a specific *Chlamydia*-RNA-sensor (trigger) sequence interested in the split sites of the luciferase gene, such that the translated protein would contain the following sequence IYALLTLPPLNN (SEQ ID NO: 29) flanked on each side by a short linker of 3 glycines.

The invention claimed is:

1. A nucleic acid sensor system comprising first and second single stranded DNA sensor parts which, when ligated together generate a single strand of a DNA expression cassette that comprises:

i) a promoter;
ii) a ribosome binding site (RBS); and
iii) a coding sequence;

wherein an exogenous target nucleic acid hybridization sequence is located within and in-frame with the coding sequence or is located between the promoter and RBS, such that the DNA expression cassette is capable of expressing a protein encoded by the coding sequence; and wherein the exogenous target nucleic acid hybridization sequence is exogenous compared to the coding sequence; and wherein the DNA expression cassette is a non-template DNA expression cassette; and the first and second sensor parts are on at least two separate molecules.

2. The nucleic acid sensor system of claim 1, wherein the exogenous target nucleic acid hybridization sequence comprises exogenous 3' and 5' hybridization regions, wherein the exogenous 3' and 5' hybridization regions are exogenous compared to the coding sequence, wherein the exogenous 3' hybridization region is included in the first sensor part and the exogenous 5' hybridization region is included in the second sensor part so that, when the sensor system is contacted with a sample that includes a target nucleic acid that hybridizes with the exogenous target nucleic acid hybridization sequence, hybridization with the target nucleic acid enables ligation of the first and second parts to generate the single strand.

3. The nucleic acid sensor system of claim 2, wherein when the first and second sensor parts are ligated together to generate the single strand of the DNA expression cassette, a ligation point of the first and second sensor parts is within the exogenous target nucleic acid hybridization sequence.

4. The nucleic acid sensor system of claim 2, wherein either the first or the second sensor part comprises:
   a) the promoter, the ribosome binding site, and a start codon of the coding sequence and the remaining sensor part comprises the remaining coding sequence;
   b) the promoter and the remaining sensor part comprises the ribosome binding site and the coding sequence; or
   c) the promoter, the ribosome binding site, and a 5' portion of the coding sequence and the remaining sensor part comprises the remaining coding sequence.

5. The nucleic acid sensor system of claim 2, wherein the first sensor part comprises, from 5' to 3':
   i) the promoter;
   ii) the ribosome binding site (RBS);
   iii) the start codon for the coding sequence; and
   iv) the exogenous 3' hybridization region in the form of a reading frame in-frame with the start codon;
and the second sensor part comprises from 5' to 3':
   i) the exogenous 5' hybridization region in the form of a reading frame in-frame with the remaining coding sequence; and
   ii) the remaining coding sequence linked downstream of and in-frame with the exogenous 5' hybridization region.

6. The nucleic acid sensor system of claim 2, wherein the first sensor part comprises, from 5' to 3':
   i) the promoter; and
   ii) the exogenous 3' hybridization region;
and the second sensor part comprises, from 5' to 3':
   i) the exogenous 5' hybridization region;
   ii) the ribosome binding sequence; and
   iii) the coding sequence.

7. The nucleic acid sensor system of claim 2, wherein the first sensor part comprises, from 5' to 3':
   i) the promoter;
   ii) the RBS;
   iii) a first portion of the coding sequence, comprising a start codon and at least one additional codon;
   iv) the exogenous 3' hybridization region in the form of a reading frame in-frame with the start codon and the at least one additional codon;
and the second sensor part comprises, from 5' to 3':
   i) the exogenous 5' hybridization region in the form of a reading frame in-frame with the first portion of the coding sequence and in-frame with the second portion of the coding sequence; and ii) the second portion of the coding sequence linked downstream of and in-frame with the exogenous 5' hybridization region.

8. The nucleic acid sensor system of claim 2, wherein the exogenous 3' hybridization region and the exogenous 5' hybridization region are each at least 6 nucleotides in length.

9. The nucleic acid sensor system of claim 2, wherein the system further comprises a primer complementary to a sequence within the DNA expression cassette.

10. The nucleic acid sensor system of claim 2, wherein the system further comprises a DNA polymerase.

11. The nucleic acid sensor system of claim 2, wherein the coding sequence of the expression cassette encodes a reporter protein.

12. A method for detecting a target nucleic acid in a sample, comprising:
   a) providing a sample comprising a target nucleic acid;
   b) contacting the sample comprising the target nucleic acid with the nucleic acid sensor system of claim 11 in the presence of a ligase under conditions favorable to the hybridization of the target nucleic acid to the exogenous 3' hybridization region of the first sensor part and to the exogenous 5' hybridization region of the second sensor part, to thereby generate the single strand of the DNA expression cassette;
   c) contacting the single strand of the DNA expression cassette produced in step b) with a cell-free expression system in the presence of a strand displacing DNA Polymerase and a primer, under conditions favorable to the production of the reporter protein;
   d) contacting the reaction product produced in step c) with a reagent enabling the detection of the expression of the reporter protein;
   e) measuring the expression of the reporter protein produced in step d) to determine the presence and/or amount of the target nucleic acid in the sample.

13. A nucleic acid sensor system comprising first and second single stranded DNA sensor parts which, when ligated together generate a single strand of a DNA expression cassette that comprises:
   i) a promoter;
   ii) a ribosome binding site (RBS); and
   iii) a coding sequence encoding a reporter protein;
wherein an exogenous target nucleic acid hybridization sequence is located within and in-frame with the coding sequence, such that the DNA expression cassette is capable of expressing the reporter protein; and
wherein the exogenous target nucleic acid hybridization sequence is exogenous compared to the coding sequence; and
wherein either the first or the second sensor part comprises:
   a) the promoter, the ribosome binding site, and the start codon of the coding sequence and the remaining sensor part comprises the remaining coding sequence; or
   b) the promoter, the ribosome binding site, and a 5' portion of the coding sequence and the remaining sensor part comprises the remaining coding sequence; and
wherein the DNA expression cassette is a non-template DNA expression cassette;
and the first and second sensor parts are on at least two separate molecules.

14. A nucleic acid sensor system comprising first and second single stranded DNA sensor parts which, when ligated together generate a single strand of a DNA expression cassette that comprises:

i) a promoter;

ii) a ribosome binding site (RBS); and iii) a coding sequence;

wherein an exogenous nucleic acid hybridization sequence is located within the first and second single stranded DNA sensor parts;

wherein the exogenous target nucleic acid hybridization sequence comprises exogenous 3' and 5' hybridization regions, wherein the exogenous target nucleic acid hybridization sequence and the exogenous 3' and 5' hybridization regions are exogenous compared to the coding sequence; wherein the exogenous 3' hybridization region is included in the first sensor part and the exogenous 5' hybridization region is included in the second sensor part so that, when the sensor system is contacted with a sample that includes a target nucleic acid that hybridizes with the exogenous target nucleic acid hybridization sequence, hybridization with the target nucleic acid enables ligation of the first and second parts to generate the single strand;

wherein the first sensor part comprises, from 5' to 3':

i) the promoter;

ii) the ribosome binding site (RBS);

iii) the start codon for the coding sequence; and iv) the exogenous 3' hybridization region in the form of a reading frame in-frame with the start codon;

and the second sensor part comprises from 5' to 3':

i) the exogenous 5' hybridization region in the form of a reading frame in-frame with the remaining coding sequence; and ii) the remaining coding sequence linked downstream of and in-frame with the exogenous 5' hybridization region.

* * * * *

SEQUENCE LISTING

<160> NUMBER OF SEQ ID NOS: 29

<210> SEQ ID NO 1
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaattaatac gactcactat agggatctat ccactactcc taaggagact ttttatgaat      60
tatctatgca ttact                                                       75

<210> SEQ ID NO 2
<211> LENGTH: 531
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aacccttccg ccactaaagt gttcacattg gaggactttg taggggactg gcgccagaca      60
gcgggctaca accttgatca ggttctggag cagggaggtg taagttcact tttccagaat     120
ttgggtgtga gtgtcacccc gatccaacgt atcgtgcttt ccggagaaaa tgggctgaag     180
atcgacatcc atgttattat tccttatgaa gggcttagcg gagatcaaat gggccaaatc     240
gaaaagattt tcaaagtggt atatcctgtt gacgaccatc attttaaggt cattctgcat     300
tacggaactt tagtcatcga cggcgtcaca cctaacatga ttgactattt tggccgtccg     360
tatgagggca tcgcagtgtt tgacggaaaa aaaatcaccg tgacagggac actgtggaac     420
ggcaataaga ttatcgacga gcgccttatt aacccagatg ggtcgctttt attccgtgtc     480
actattaatg gtgtcactgg ctggcgtttg tgcgaacgca tcctggcata a               531

<210> SEQ ID NO 3
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

-continued

```
gaattaatac gactcactat aggggtcctc ccccccaaaa ctacaataag ggggtttttt       60
atgtccattc ctggctttaa t                                                 81

<210> SEQ ID NO 4
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gaattaatac gactcactat aggatctat ccactactcc taaggagact ttttatgtcc        60
attcctggct ttaat                                                        75

<210> SEQ ID NO 5
<211> LENGTH: 531
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
tttactggta cagtttcagt gttcacattg gaggactttg taggggactg gcgccagaca       60
gcgggctaca accttgatca ggttctggag cagggaggtg taagttcact tttccagaat      120
ttgggtgtga gtgtcacccc gatccaacgt atcgtgcttt ccggagaaaa tgggctgaag      180
atcgacatcc atgttattat tccttatgaa gggcttagcg gagatcaaat gggccaaatc      240
gaaaagattt tcaaagtggt atatcctgtt gacgaccatc attttaaggt cattctgcat      300
tacggaactt tagtcatcga cggcgtcaca cctaacatga ttgactattt tggccgtccg      360
tatgagggca tcgcagtgtt tgacggaaaa aaaatcaccg tgacagggac actgtggaac      420
ggcaataaga ttatcgacga gcgccttatt aacccagatg ggtcgctttt attccgtgtc      480
actattaatg tgtgtcactgg ctggcgtttg tgcgaacgca tcctggcata a              531

<210> SEQ ID NO 6
<211> LENGTH: 612
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
aacccttccg ccactaaagt gttcacattg gaggactttg taggggactg gcgccagaca       60
gcgggctaca accttgatca ggttctggag cagggaggtg taagttcact tttccagaat      120
ttgggtgtga gtgtcacccc gatccaacgt atcgtgcttt ccggagaaaa tgggctgaag      180
atcgacatcc atgttattat tccttatgaa gggcttagcg gagatcaaat gggccaaatc      240
gaaaagattt tcaaagtggt atatcctgtt gacgaccatc attttaaggt cattctgcat      300
tacggaactt tagtcatcga cggcgtcaca cctaacatga ttgactattt tggccgtccg      360
tatgagggca tcgcagtgtt tgacggaaaa aaaatcaccg tgacagggac actgtggaac      420
ggcaataaga ttatcgacga gcgccttatt aacccagatg ggtcgctttt attccgtgtc      480
actattaatg tgtgtcactgg ctggcgtttg tgcgaacgca tcctggcata ataataagaa     540
ttaatacgac tcactatagg gatctatcca ctactcctaa ggagactttt tatgaattat      600
```
ctatgcatta ct                                                                             612

<210> SEQ ID NO 7
<211> LENGTH: 644
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
tttactggta cagtttcagt gttcacattg gaggactttg taggggactg gcgccagaca      60
gcgggctaca accttgatca ggttctggag cagggaggtg taagttcact tttccagaat     120
ttgggtgtga gtgtcacccc gatccaacgt atcgtgcttt ccggagaaaa tgggctgaag     180
atcgacatcc atgttattat tccttatgaa gggcttagcg gagatcaaat gggccaaatc     240
gaaaagattt tcaaagtggt atatcctgtt gacgaccatc attttaaggt cattctgcat     300
tacggaactt tagtcatcga cggcgtcaca cctaacatga ttgactattt tggccgtccg     360
tatgagggca tcgcagtgtt tgacggaaaa aaaatcaccg tgacagggac actgtggaac     420
ggcaataaga ttatcgacga gcgccttatt aacccagatg ggtcgctttt attccgtgtc     480
actattaatg gtgtcactgg ctggcgtttg tgcgaacgca tcctggcata actagcataa     540
cccctctcta aacggagggg tttgaattaa tacgactcac tatagggggtc ctccccccca     600 aaactacaat aaggggggttt tttatgtcca ttcctggctt taat                      644

<210> SEQ ID NO 8
<211> LENGTH: 629
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
tttactggta cagtttcagt gttcacattg gaggactttg taggggactg gcgccagaca      60
gcgggctaca accttgatca ggttctggag cagggaggtg taagttcact tttccagaat     120
ttgggtgtga gtgtcacccc gatccaacgt atcgtgcttt ccggagaaaa tgggctgaag     180
atcgacatcc atgttattat tccttatgaa gggcttagcg gagatcaaat gggccaaatc     240
gaaaagattt tcaaagtggt atatcctgtt gacgaccatc attttaaggt cattctgcat     300
tacggaactt tagtcatcga cggcgtcaca cctaacatga ttgactattt tggccgtccg     360
tatgagggca tcgcagtgtt tgacggaaaa aaaatcaccg tgacagggac actgtggaac     420
ggcaataaga ttatcgacga gcgccttatt aacccagatg ggtcgctttt attccgtgtc     480
actattaatg gtgtcactgg ctggcgtttg tgcgaacgca tcctggcata atgataatag     540
tttggtttga attaatacga ctcactatag gggtcctccc ccccaaaact acaataaggg     600
ggttttttat gtccattcct ggctttaat                                        629

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
gaattaatac gactcactat aggaattatc tatgcattac t                          41

<210> SEQ ID NO 10
<211> LENGTH: 555
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
aacccttccg ccactaaagg gtcaattaag gaggtatata tggtgttcac attggaggac        60
tttgtagggg actggcgcca gacagcgggc tacaaccttg atcaggttct ggagcaggga       120
ggtgtaagtt cacttttcca gaatttgggt gtgagtgtca ccccgatcca acgtatcgtg       180
ctttccggag aaaatgggct gaagatcgac atccatgtta ttattcctta tgaagggctt       240
agcggagatc aaatgggcca aatcgaaaag attttcaaag tggtatatcc tgttgacgac       300
catcatttta aggtcattct gcattacgga actttagtca tcgacggcgt cacacctaac       360
atgattgact attttggccg tccgtatgag ggcatcgcag tgtttgacgg aaaaaaaatc       420
accgtgacag ggacactgtg gaacggcaat aagattatcg acgagcgcct tattaaccca       480
gatgggtcgc ttttattccg tgtcactatt aatggtgtca ctggctggcg tttgtgcgaa       540
cgcatcctgg cataa                                                         555

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gaattaatac gactcactat aggtccattc ctggctttaa t                          41

<210> SEQ ID NO 12
<211> LENGTH: 590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
tttactggta cagtttcaaa actgtaagcc cgtagaaagg actttcaaac aataagcggg        60
taaggaggta ttaaatggtg ttcacattgg aggactttgt aggggactgg cgccagacag       120
cgggctacaa ccttgatcag gttctggagc agggaggtgt aagttcactt ttccagaatt       180
tgggtgtgag tgtcaccccg atccaacgta tcgtgctttc cggagaaaat gggctgaaga       240
tcgacatcca tgttattatt ccttatgaag ggcttagcgg agatcaaatg gccaaatcg       300 aaaagatttt caaagtggta tatcctgttg acgaccatca tttttaaggtc attctgcatt       360 acggaacttt agtcatcgac ggcgtcacac ctaacatgat tgactatttt ggccgtccgt       420
atgagggcat cgcagtgttt gacggaaaaa aaatcaccgt gacagggaca ctgtggaacg       480
gcaataagat tatcgacgag cgccttatta acccagatgg gtcgctttta ttccgtgtca       540
ctattaatgg tgtcactggc tggcgtttgt gcgaacgcat cctggcataa                  590
```

-continued

```
<210> SEQ ID NO 13
<211> LENGTH: 394
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gaattaatac gactcactat aggtgagtat ataggtagaa gaggtattgg aggtattgat      60
ggtgttcaca ttggaggact ttgtagggga ctggcgccag acagcgggct acaaccttga     120
tcaggttctg gagcagggag gtgtaagttc acttttccag aatttgggtg tgagtgtcac     180
cccgatccaa cgtatcgtgc tttccggaga aaatgggctg aagatcgaca tccatgttat     240
tattccttat gaagggctta gcggagatca aatgggccaa atcgaaaaga ttttcaaagt     300
ggtatatcct gttgacgacc atcattttaa ggtcattctg cattacggaa ctttagtcat     360
cgacggcggt ggcgggaatt atctatgcat tact                                  394

<210> SEQ ID NO 14
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
aacccttccg ccactaaagg cggtggggtc acacctaaca tgattgacta ttttggccgt      60
ccgtatgagg gcatcgcagt gtttgacgga aaaaaaatca ccgtgacagg gacactgtgg     120
aacggcaata agattatcga cgagcgcctt attaacccag atgggtcgct tttattccgt     180
gtcactatta atggtgtcac tggctggcgt ttgtgcgaac gcatcctggc ataa          234

<210> SEQ ID NO 15
<211> LENGTH: 394
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gaattaatac gactcactat aggtgagtat ataggtagaa gaggtattgg aggtattgat      60
ggtgttcaca ttggaggact ttgtagggga ctggcgccag acagcgggct acaaccttga     120
tcaggttctg gagcagggag gtgtaagttc acttttccag aatttgggtg tgagtgtcac     180
cccgatccaa cgtatcgtgc tttccggaga aaatgggctg aagatcgaca tccatgttat     240
tattccttat gaagggctta gcggagatca aatgggccaa atcgaaaaga ttttcaaagt     300
ggtatatcct gttgacgacc atcattttaa ggtcattctg cattacggaa ctttagtcat     360
cgacggcggt ggcgggtcca ttcctggctt taat                                  394

<210> SEQ ID NO 16
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
```

```
tttactggta cagtttcagg cggtggggtc acacctaaca tgattgacta ttttggccgt          60
ccgtatgagg gcatcgcagt gtttgacgga aaaaaaatca ccgtgacagg gacactgtgg         120
aacggcaata agattatcga cgagcgcctt attaacccag atgggtcgct tttattccgt         180
gtcactatta atggtgtcac tggctggcgt ttgtgcgaac gcatcctggc ataa              234
```

```
<210> SEQ ID NO 17
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gaattaatac gactcactat aggtgagtat ataggtagaa gaggtattgg aggtattgat          60
ggtgttcaca ttggaggact ttgtagggga ctggcgccag acagcgggct acaaccttga         120
tcaggttctg gagcagggag gtgtaagttc acttttccag aatttgggtg tgagtgtcac         180
cccgatccaa cgtatcgtgc tttccggaga aaatgggctg aagatcgaca tccatgttat         240
tattccttat gaagggctta gcggagatca aatgggccaa atcgaaaaga tttttcaaagt        300 ggtatatcct gttgacgacc atcattttaa ggtcattctg cattacggaa ctttagtcat         360
cgacggc                                                                   367
```

```
<210> SEQ ID NO 18
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gtcacaccta acatgattga ctattttggc cgtccgtatg agggcatcgc agtgtttgac          60
ggaaaaaaaa tcaccgtgac agggacactg tggaacggca ataagattat cgacgagcgc         120
cttattaacc cagatgggtc gctttttattc cgtgtcacta ttaatggtgt cactggctgg        180
cgtttgtgcg aacgcatcct ggcataa                                             207
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttatgccagg atgcgttcgc                                                       20
```

```
<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tttagtggcg gaagggttag taatgcatag ataatt                                    36
```

```
<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgaaactgta ccagtaaaat taaagccagg aatgga                                         36

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aatcatgtta ggtgtgacgc cgtcgatgac taaagt                                         36

<210> SEQ ID NO 23
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
uuuaguggcg gaaggguuag uaaugcauag auaauu                                         36

<210> SEQ ID NO 24
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uuuaguggcg gaaggguugg uaaugcauag auaauu                                         36

<210> SEQ ID NO 25
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uuuaguggcg gaaggguaag uaaugcauag auaauu                                         36

<210> SEQ ID NO 26
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uuuaguggcg gaaggugag uaaugcauag auaauu                                          36

<210> SEQ ID NO 27
```

```
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uuuaguggcg gaaggguggg uaaugcauag auaauu                                      36

<210> SEQ ID NO 28
<211> LENGTH: 170
<212> TYPE: PRT
<213> ORGANISM: Unknown
<220> FEATURE:
<223> OTHER INFORMATION: Description of Unknown:
      Luciferase sequence

<400> SEQUENCE: 28

Val Phe Thr Leu Arg Asp Phe Val Gly Asp Trp Arg Gln Thr Ala Gly
1               5                   10                  15

Tyr Asn Leu Asp Gln Val Leu Glu Gln Gly Gly Val Ser Ser Leu Phe
                20                  25                  30

Gln Asn Leu Gly Val Ser Val Thr Pro Ile Gln Arg Ile Val Leu Ser
            35                  40                  45

Gly Glu Asn Gly Leu Lys Ile Asp Ile His Val Ile Ile Pro Tyr Glu
        50                  55                  60

Gly Leu Ser Gly Asp Gln Met Gly Gln Ile Glu Lys Ile Phe Lys Val
65                  70                  75                  80

Val Tyr Pro Val Asp Asp His His Phe Lys Val Ile Leu His Tyr Gly
                85                  90                  95

Thr Leu Val Ile Asp Gly Val Thr Pro Asn Met Ile Asp Tyr Phe Gly
            100                 105                 110

Arg Pro Tyr Glu Gly Ile Ala Val Phe Asp Gly Lys Lys Ile Thr Val
            115                 120                 125

Thr Gly Thr Leu Trp Asn Gly Asn Lys Ile Ile Asp Glu Arg Leu Ile
        130                 135                 140

Asn Pro Asp Gly Ser Leu Leu Phe Arg Val Thr Ile Asn Gly Val Thr
145                 150                 155                 160

Gly Trp Arg Leu Cys Glu Arg Ile Leu Ala
                165                 170

<210> SEQ ID NO 29
<211> LENGTH: 12
<212> TYPE: PRT
<213> ORGANISM: Unknown
<220> FEATURE:
<223> OTHER INFORMATION: Description of Unknown:
      Translated protein sequence

<400> SEQUENCE: 29

Ile Tyr Ala Leu Leu Thr Leu Pro Pro Leu Asn Asn
1               5                   10
```